United States Patent
Bathe et al.

(10) Patent No.: US 7,214,526 B2
(45) Date of Patent: May 8, 2007

(54) ALLELES OF THE MQO GENE FROM CORYNEFORM BACTERIA

(75) Inventors: Brigitte Bathe, Salzkotten (DE); Stephan Hans, Osnabruck (DE); Natalie Schischka, Bielefeld (DE); Georg Thierbach, Bielefeld (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 11/333,718

(22) Filed: Jan. 18, 2006

(65) Prior Publication Data

US 2006/0166338 A1 Jul. 27, 2006

Related U.S. Application Data

(60) Provisional application No. 60/645,588, filed on Jan. 24, 2005.

(30) Foreign Application Priority Data

Jan. 19, 2005 (DE) .................. 10 2005 002 489
Jul. 12, 2005 (DE) .................. 10 2005 032 429

(51) Int. Cl.
*C07H 21/04* (2006.01)
*C12P 13/22* (2006.01)
*C12P 13/04* (2006.01)
*C12N 1/21* (2006.01)

(52) U.S. Cl. .................. 435/252.3; 435/191; 435/108; 435/106; 435/471; 435/252.32; 435/320.1; 435/252.33; 536/23.2

(58) Field of Classification Search .................. None
See application file for complete search history.

(56) References Cited

U.S. PATENT DOCUMENTS

2004/0180408 A1    9/2004   Pompejus et al. ......... 435/69.1

FOREIGN PATENT DOCUMENTS

CA        2301407         9/2000
WO    WO 02/086137     10/2002

OTHER PUBLICATIONS

Molenaar, et al., *Eur. J. Biochem.* 254:395-403 (1998).
Pfefferle, et al., *Adv. Biochem Eng. Biotech.* 79:59-112 (2003).

*Primary Examiner*—Rebecca E. Prouty
*Assistant Examiner*—Mohammad Meah
(74) *Attorney, Agent, or Firm*—Michael A. Sanzo; Law Office of Michael A. Sanzo, LLC

(57) ABSTRACT

The invention relates to mutants and alleles of the coryneform bacterium mqo gene which encodes malate quinone oxidoreductases which contain any amino acid apart from L-serine at position 111, or a comparable position, in the amino acid sequence, and to processes for fermentatively preparing amino acids, preferably L-lysine, L-tryptophan and L-proline, using bacteria which comprise these alleles.

12 Claims, 1 Drawing Sheet

Figure 1: Map of the plasmid pK18mobsacB_mqoS111F
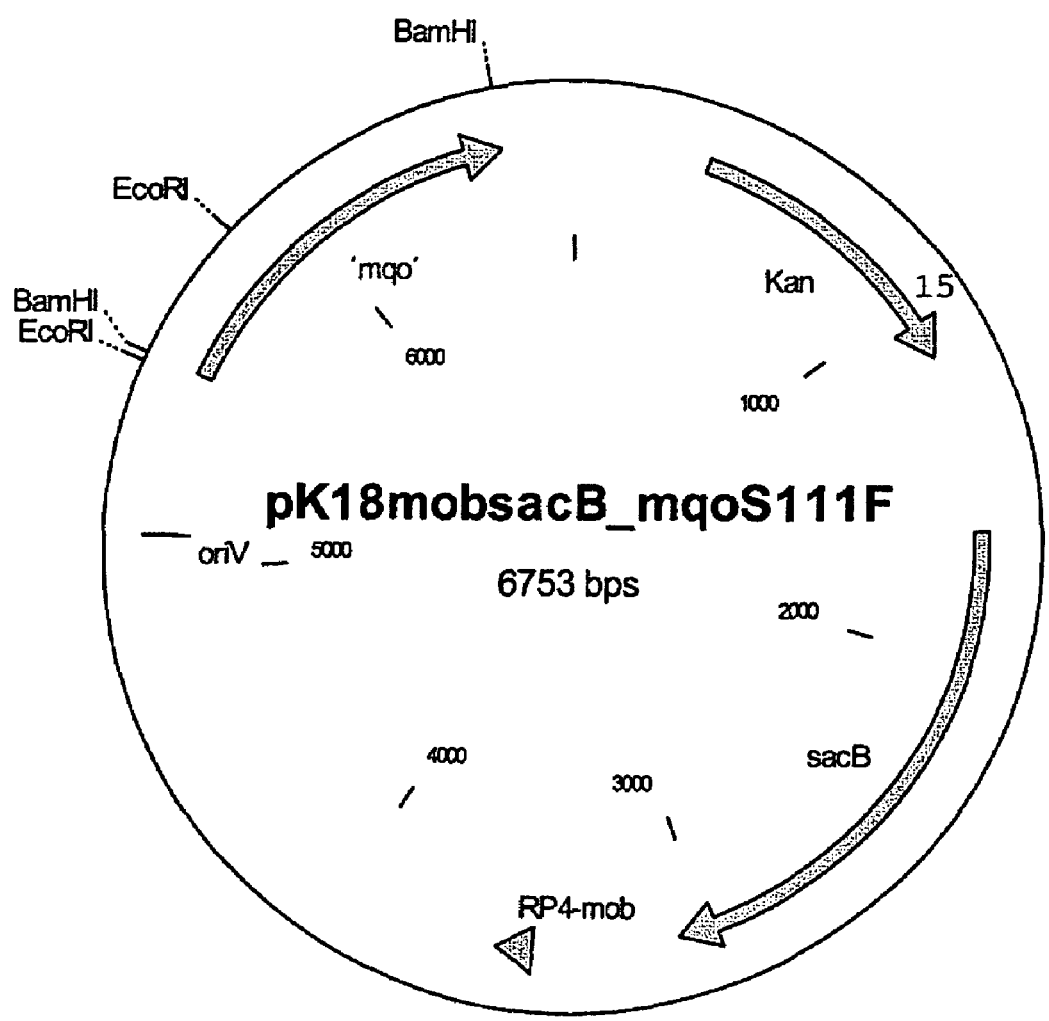

ALLELES OF THE MQO GENE FROM CORYNEFORM BACTERIA

CROSS REFERENCE TO RELATED APPLICATIONS

The present application claims priority to German application nos. 10 2005 002 489.0, filed on Jan. 19, 2005, and 10 2005 032 429.0, filed on Jul. 12, 2005. This application also claims priority to, and the benefit of, U.S. provisional application 60/645,588, filed on Jan. 24, 2005. The contents of these prior applications are hereby incorporated by reference in their entirety.

FIELD OF THE INVENTION

The invention relates to mutants and alleles of the coryneform bacterium mqo gene which encode malate quinone oxidoreductase (EC: 1.1.99.16) variants and to processes for preparing amino acids, in particular L-lysine, tryptophan and L-proline, using bacteria which comprise these alleles.

BACKGROUND OF THE INVENTION

Amino acids are used in human medicine, in the pharmaceutical industry, in the foodstuffs industry and, very particularly, in animal nutrition.

It is known that amino acids are prepared by fermenting strains of coryneform bacteria, in particular *Corynebacterium glutamicum*. Because of their great importance, efforts are continuously being made to improve the preparation methods. Methodological improvements can concern measures relating to fermentation, such as stirring and supplying with oxygen, or the composition of the nutrient media, such as the sugar concentration during the fermentation, or the workup to the product form by means of ion exchange chromatography, for example, or the intrinsic performance properties of the microorganism itself.

Methods of mutagenesis, selection and mutant choice are used for improving the performance properties of these microorganisms. This results in strains which are resistant to antimetabolites or auxotrophic for metabolites of regulatory importance and which produce amino acids. A known antimetabolite is the lysine analog S-(2-aminoethyl)-L-cysteine (AEC).

For some years now, methods of recombinant DNA technology have also been used for improving L-amino acid-producing strains of *corynebacterium* by amplifying individual amino acid biosynthesis genes and investigating the consequences of this for amino acid production. A review of a wide variety of aspects of the genetics, the metabolism and the biotechnology of *Corynebacterium glutamicum* can be found in Pü hler (chief ed.), Journal of Biotechnology 104 (1–3), 1–338, 2003.

The nucleotide sequence of the *Corynebacterium glutamicum* malate quinone oxidoreductase-encoding gene was determined by Molenaar et al. (European Journal of Biochemistry 254: 395–403 (1998)) and is available to the public in the database of the National Center for Biotechnology Information (NCBI) at the National Library of Medicine (Bethesda, Md., USA) under the accession number AJ224946.

It is furthermore to be found in patent application WO 01/00844 as sequence No. 569 and sequence No. 571 as well as in patent application EP-A-1108790 as sequence No. 3478, sequence No. 7065 and sequence No. 7066.

EP1038969 describes an improvement in the fermentative production of L-amino acids by coryneform bacteria which results from amplifying the mqo gene.

On the other hand, WO 02086137 describes the beneficial effect on L-amino acid production by coryneform bacteria which is achieved by attenuating the mqo gene. A mutation of the mqo gene which is described in the application and which is designated "allele 672" carries the nucleotide adenine in place of the nucleotide guanine at position 672 in the DNA sequence of the mqo gene, with this resulting in the formation of a stop codon at position 224 in the amino acid sequence of the *Corynebacterium glutamicum* malate quinone oxidoreductase. The "allele 1230", which, in addition to the mutation in allele 672, also contains a cytosine to thymine transition at position 1230 in the nucleotide sequence of the mqo gene, is also described. The application furthermore describes the elimination of the mqo gene as a result of gene interruption brought about by integration mutagenesis, with this leading to an increase in the production of L-lysine by the corresponding strain.

The microbial biosynthesis of L-amino acids in coryneform bacteria is a system which is complex and multilayered, being interlinked with a variety of other metabolic pathways in the cell. It is therefore not possible to make any prediction as to whether complete elimination of, or a reduction in, the catalytic activity of the malate quinone oxidoreductase will improve the production of L-amino acids at different steps. It is therefore desirable to also have available malate quinone oxidoreductase variants which differ in the degree of their activity.

For the sake of greater clarity, the nucleotide sequence of the *Corynebacterium glutamicum* malate quinone oxidoreductase-encoding mqo gene (wild-type gene) in accordance with the information supplied by the NCBI database is depicted in SEQ ID NO: 1 while the ensuing amino acid sequence of the encoded malate quinone oxidoreductase is depicted in SEQ ID NO: 2 and 4. Nucleotide sequences which are located upstream and downstream are also given in SEQ ID NO: 3.

OBJECT OF THE INVENTION

The inventors have set themselves the object of providing novel measures for improving the preparation of amino acids, in particular L-lysine, L-tryptophan and L-proline.

BRIEF DESCRIPTION OF THE DRAWINGS

FIG. 1: Map of the plasmid pK18mobsacB_mqoS111F

DESCRIPTION OF THE INVENTION

The invention relates to mutants of coryneform bacteria which are generated or isolated, which preferably secrete amino acids and which comprise a gene or allele which encodes a polypeptide possessing malate quinone oxidoreductase activity, characterized in that the polypeptide comprises an amino acid sequence which contains, at position 111 or a corresponding or comparable position in the amino acid sequence, any proteinogenic amino acid apart from L-serine. The replacement of L-serine with L-phenylalanine or L-alanine is preferred.

Of the coryneform bacteria, preference is given to the genus *Corynebacterium*. Particular preference is given to amino acid-secreting strains which are based on the following species:

*Corynebacterium efficiens*, for example the strain DSM44549,
*Corynebacterium glutamicum*, for example the strain ATCC13032,
*Corynebacterium thermoaminogenes*, for example the strain FERM BP-1539, and
*Corynebacterium ammoniagenes*, for example the strain ATCC6871, with the species *Corynebacterium glutamicum* being very particularly preferred.

Some representatives of the species *Corynebacterium glutamicum* are also known in the prior art under other species designations. These representatives include, for example:

*Corynebacterium acetoacidophilum* ATCC13870
*Corynebacterium lilium* DSM20137
*Corynebacterium melassecola* ATCC17965
*Brevibacterium flavum* ATCC14067
*Brevibacterium lactofermentum* ATCC13869 and
*Brevibacterium divaricatum* ATCC14020

Examples of known representatives of amino acid-secreting strains of coryneform bacteria are the L-lysine-producing strains

*Corynebacterium glutamicum* DM58-1/pDM6 (=DSM4697) described in EP 0 358 940
*Corynebacterium glutamicum* MH20 (=DSM5714) described in EP 0 435 132
*Corynebacterium glutamicum* AHP-3 (=FermBP-7382) described in EP 1 108 790
*Corynebacterium thermoaminogenes* AJ12521 (=FERM BP-3304) described in U.S. Pat. No. 5,250,423 or the L-tryptophan-producing strains

*Corynebacterium glutamicum* K76 (=FermBP-1847) described in U.S. Pat. No. 5,563,052
*Corynebacterium glutamicum* BPS13 (=FermBP-1777) described in U.S. Pat. No. 5,605,818
*Corynebacterium glutamicum* FermBP-3055 described in U.S. Pat. No. 5,235,940

Information with regard to the taxonomic classification of strains of this group of bacteria can be found, inter alia, in Seiler (Journal of General Microbiology 129, 1433–1477 (1983), Kämpfer and Kroppenstedt (Canadian Journal of Microbiology 42, 989–1005 (1996)), Liebl et al (International Journal of Systematic Bacteriology 41, 255–260 (1991) and in U.S. Pat. No. 5,250,434.

Strains having the designation "ATCC" can be obtained from the American Type Culture Collection (Manassas, Va., USA). Strains having the designation "DSM" can be obtained from the Deutsche Sammlung von Mikroorganismen und Zellkulturen [German Collection of Microorganisms and Cell Cultures] (DSMZ, Brunswick, Germany). Strains having the designation "FERM" can be obtained from the National Institute of Advanced Industrial Science and Technology (AIST Tsukuba Central 6, 1-1-1 Higashi, Tsukuba Ibaraki, Japan). The abovementioned strains of *Corynebacterium thermoaminogenes* (FERM BP-1539, FERM BP-1540, FERM BP-1541 and FERM BP-1542) are described in U.S. Pat. No. 5,250,434.

"Proteinogenic amino acids" are understood as being the amino acids which occur in natural proteins, that is in proteins derived from microorganisms, plants, animals and humans. These amino acids include, in particular, L-amino acids selected from the group L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine.

The mutants according to the invention preferably secrete the abovementioned proteinogenic amino acids, in particular L-lysine. The term amino acids also encompasses their salts such as lysine monohydrochloride or lysine sulfate in the case of the amino acid L-lysine.

The invention furthermore relates to mutants of coryneform bacteria which comprise an mqo allele which encodes a polypeptide which possesses malate quinone oxidoreductase enzyme activity and which comprises the amino acid sequence of SEQ ID NO: 2 in which any proteinogenic amino acid apart from L-serine is present at position 111. The replacement of L-serine with L-phenylalanine or L-alanine is preferred. Where appropriate, the amino acid sequence of the polypeptide additionally contains a replacement of the amino acid L-alanine with another proteinogenic amino acid, preferably L-serine, at position 201.

The invention furthermore relates to mutants of coryneform bacteria which comprise an mqo allele which encodes a polypeptide which possesses malate quinone oxidoreductase enzyme activity and which contains any proteinogenic amino acid apart from L-serine, preferably L-phenylalanine or L-alanine, at the position corresponding to position 111 in the amino acid sequence depicted in SEQ ID NO: 2, with the gene comprising a nucleotide sequence which is identical to the nucleotide sequence of a polynucleotide which can be obtained by means of a polymerase chain reaction (PCR) using a primer pair whose nucleotide sequences in each case comprise at least 15 consecutive nucleotides which are selected from the nucleotide sequence between position 1 and 349 of SEQ ID NO: 3 and from the complementary nucleotide sequence between position 2002 and 1850 of SEQ ID NO: 3. Examples of suitable primer pairs are depicted in SEQ ID NO: 11 and SEQ ID NO: 12 and in SEQ ID NO: 13 and SEQ ID NO: 14. Preference is given to the starting material (template DNA) being coryneform bacterium chromosomal DNA which has been treated, in particular, with a mutagen. Particular preference is given to the chromosomal DNA of the genus *Corynebacterium* and very particular preference is given to that of the species *Corynebacterium glutamicum*.

The invention furthermore relates to mutants of coryneform bacteria which comprise an mqo allele which encodes a polypeptide which possess malate quinone oxidoreductase enzyme activity and which comprises an amino acid sequence having a length corresponding to 500 L-amino acids, with any proteinogenic amino acid apart from L-serine, preferably L-phenylalanine or L-alanine, being present at position 111. Where appropriate, the amino acid sequence of the polypeptide additionally contains a replacement of the amino acid L-alanine with another proteinogenic amino acid, preferably L-serine, at position 201.

The invention furthermore relates to mutants of coryneform bacteria which comprise an mqo allele which encodes a polypeptide which possesses malate quinone oxidoreductase enzyme activity and which contains, at position 106 to 116 of the amino acid sequence, the amino acid sequence corresponding to position 106 to 116 in SEQ ID NO: 6 or 8. The amino acid sequence of the encoded polypeptide preferably contains an amino acid sequence corresponding to position 96 to 126 in SEQ ID NO: 6 or 8 or position 81 to 141 in SEQ ID NO: 6 or 8 or position 66 to 156 in SEQ ID NO: 6 or 8 or position 51 to 181 in SEQ ID NO: 6 or 8 or position 21 to 201 in SEQ ID NO: 6, 8 or 10 or position 2 to 301 in SEQ ID NO: 6, 8 or 10 or position 2 to 401 in SEQ ID NO: 6, 8 or 10 or position 2 to 499 in SEQ ID NO: 6, 8 or 10 or position 2 to 500 in SEQ ID NO: 6, 8 or 10. Very particularly preferably, the encoded protein is 500 amino acids in length.

The invention furthermore relates to mutants of coryneform bacteria which comprise an mqo allele which encodes a polypeptide which possesses malate quinone oxidoreductase enzyme activity and which contains any amino acid apart from L-serine at position 111 or at the corresponding position of the amino acid sequence, with preference being given to replacement with L-phenylalanine or L-alanine and with its amino acid sequence additionally being at least 90%, preferably at least 92% or at least 94% or at least 96%, and very particularly preferably at least 97% or at least 98% or at least 99%, identical to the amino acid sequence depicted in SEQ ID NO: 6 or 8. An example of an amino acid sequence which possesses at least 99% identity with the amino acid sequence depicted in SEQ ID NO: 6 or 8 is shown in SEQ ID NO: 10. The polypeptide of this malate quinone oxidoreductase possesses the amino acid replacement of L-alanine with L-serine at position 201 in addition to the amino acid replacement at position 111.

The invention furthermore relates to mutants of coryneform bacteria which comprise an mqo allele which encodes a polypeptide which possesses malate quinone oxidoreductase enzyme activity and which contains any amino acid, apart from L-serine, at position 111 or at the corresponding position of the amino acid sequence, with preference being given to replacement with L-phenylalanine or L-alanine and with its nucleotide sequence additionally being at least 90%, preferably at least 92% or at least 94% or at least 96%, and very particularly preferably at least 97% or at least 98% or at least 99%, identical to the nucleotide sequence depicted in SEQ ID NO: 5 or 7. An example of a nucleotide sequence of an mqo allele which possesses at least 99% identity with the nucleotide sequence depicted in SEQ ID NO: 5 or 7 is shown in SEQ ID NO: 9. The nucleotide sequence of this mqo allele possesses the nucleotide replacement of guanine with thymine at position 601 in addition to the nucleotide replacement of thymine with guanine at position 331 (see SEQ ID NO: 9).

It is known that conservative amino acid substitutions only alter the enzyme activity to a trivial extent. Accordingly, the mqo allele which is present in the mutants according to the invention, and which encodes a polypeptide possessing malate quinone oxidoreductase enzyme activity, can contain one (1) or more conservative amino acid substitution(s) in addition to the amino acid sequence shown in SEQ ID NO: 6, SEQ ID NO: 8 or SEQ ID NO: 10. The polypeptide preferably contains at most two (2), at most three (3), at most four (4) or at most five (5) conservative amino acid substitutions.

In the case of the aromatic amino acids, substitutions are said to be conservative when phenylalanine, tryptophan and tyrosine replace each other. In the case of hydrophobic amino acids, substitutions are said to be conservative when leucine, isoleucine and valine replace each other. In the case of the polar amino acids, substitutions are said to be conservative when glutamine and asparagine replace each other. In the case of the basic amino acids, substitutions are said to be conservative when arginine, lysine and histidine replace each other. In the case of the acidic amino acids, substitutions are said to be conservative when aspartic acid and glutamic acid replace each other. In the case of the hydroxyl group-containing amino acids, substitutions are said to be conservative when serine and threonine replace each other.

During the work on the present invention, it was observed, by comparing amino acid sequences using the Clustal program (Thompson et al., Nucleic Acids Research 22, 4637–4680 (1994)), that the amino acid sequences of the malate quinone oxidoreductases of different bacteria, such as *Escherichia coli, Corynebacterium glutamicum, Corynebacterium efficiens, Corynebacterium diphtheriae, Mycobacterium tuberculosis, Bacillus cereus* and *Bacillus halodurans*, contain a sequence motif consisting of the sequence Trp-Asn-Asn-Ala-Gly-Thr-Gly-His-Sal-Ala-Leu and also a sequence motif consisting of the sequence Bra-Leu-Gly-Ali-Ser-Pro-Gly-Ala-Ser. The term "Bra" stands for the amino acid Ile or Leu, while the term "Sal" stands for the amino acids Ser or Ala and the term "Ali" stands for the amino acid Ala or Gly.

Accordingly, preference is given to those mutants of coryneform bacteria which comprise an mqo allele which encodes a polypeptide which possesses malate quinone oxidoreductase enzyme activity, which comprises at least one amino acid sequence selected from the group Trp-Asn-Asn-Ala-Gly-Thr-Gly-His-Sal-Ala-Leu and Bra-Leu-Gly-Ali-Ser-Pro-Gly-Ala-Ser and which contains any amino acid apart from L-serine, preferably L-phenylalanine or L-alanine, at position 111 or the corresponding or comparable position in the amino acid sequence. Where appropriate, the amino acid sequence additionally contains a replacement of the amino acid L-alanine with another proteinogenic amino acid, preferably L-serine, at position 201 in accordance with SEQ ID NO: 2.

The amino acid sequence motif Trp-Asn-Asn-Ala-Gly-Thr-Gly-His-Sal-Ala-Leu is, for example, present from position 59 to 69 in SEQ ID NO: 6, 8 or 10. The amino acid sequence motif Bra-Leu-Gly-Ali-Ser-Pro-Gly-Ala-Ser is, for example, present from position 433 to 441 in SEQ ID NO: 6, 8 or 10.

The invention finally relates to mutants of coryneform bacteria which comprise an mqo allele which encodes a polypeptide which possesses malate quinone oxidoreductase enzyme activity and which comprises the amino acid sequence depicted in SEQ ID NO: 6, SEQ ID NO: 8 or SEQ ID NO: 10.

It is known that enzymes which are intrinsic to the host, i.e. what are termed aminopeptidases, remove the terminal methionine during protein synthesis.

The expression "a position which corresponds to position 111 in the amino acid sequence" or "a position which is comparable to position 111 in the amino acid sequence" is understood as meaning the fact that, by inserting or deleting a codon which encodes an amino acid in the N-terminal region (based on position 111 in SEQ ID NO: 6, 8 or 10) of the encoded polypeptide, the position specification and length specification are formally increased by one unit, in the case of an insertion, or reduced by one unit in the case of a deletion. For example, as a result of deleting the TCA codon, which encodes the amino acid L-serine, at position 2 in SEQ ID NO: 5, 7 or 8, the L-phenylalanine or L-alanine moves from position 111 to position 110. The length specification would then be: 499 amino acids. In the same way, the length specification is formally increased by one unit, in the case of an insertion, or reduced by one unit, in the case of a deletion, as a result of inserting or deleting a codon encoding an amino acid in the C-terminal region (based on the position 111) of the encoded polypeptide. Comparable positions of this nature can readily be identified by comparing the amino acid sequences in the form of an alignment, for example using the Clustal program. The enzymic activity is not significantly affected by such insertions and deletions. "Not significantly affected" means that the enzymic activity of said variants differs by at most 10%, at most 7.5%, at most 5%, at most 2.5% or at most 1% from the activity of the polypeptide having the amino acid sequence depicted in SEQ ID NO: 6 or 8 or, where appropriate, 10.

Accordingly, the invention also relates to mqo alleles which encode polypeptide variants of SEQ ID NO: 6, 8 or 10 which contain one or more insertion(s) or deletion(s). The polypeptide preferably contains at most 5, at most 4, at most 3 or at most 2 insertions or deletions of amino acids.

The sequence motifs Trp-Asn-Asn-Ala-Gly-Thr-Gly-His-Sal-Ala-Leu and Bra-Leu-Gly-Ali-Ser-Pro-Gly-Ala-Ser are preferably not disrupted by these insertions/deletions.

It is possible to use classical in-vitro mutagenesis methods to prepare the mutants according to the invention, employing populations of coryneform bacterial cells and mutagenic substances such as N-methyl-N'-nitro-N-nitrosoguanidine (MNNG) or ultraviolet light. Methods of mutagenesis are described, for example, in Manual of Methods for General Bacteriology (Gerhard et al. (Eds.), American Society for Microbiology, Washington, D.C., USA, 1981) or in Tosaka et al. (Agricultural and Biological Chemistry 42(4), 745–752 (1978)) or in Konicek et al (Folia Microbiologica 33, 337–343 (1988)). Typical mutageneses using MNNG involve concentrations of from 50 to 500 mg/l, or else higher concentrations of up to at most 1 g/l, and an incubation time of from 1 to 30 minutes at a pH of from 5.5 to 7.5. Under these conditions, the number of viable cells is reduced by a proportion of from approximately 50% to 90% or approximately 50% to 99% or approximately 50% to 99.9% or more.

Mutants or cells are removed from the mutagenized cell population and replicated. In a further step, the cells are disrupted, for example with the aid of a Ribolyser (Hybaid, Heidelberg, Germany), and the intracellular malate quinone oxidoreductase activity is determined, for example using the method of Molenaar et al. (European Journal of Biochemistry 254: 395–403 (1998)). This makes it possible to identify mutants whose intracellular malate quinone oxidoreductase activity is reduced by at least 30%, preferably at least 35% and very particularly preferably by at least 40% as compared with the unmutagenized starting strain. Subsequently, the ability of the mutants to secrete amino acids, preferably L-lysine, L-tryptophan or L-proline, is investigated in a batch culture using a suitable nutrient medium. Suitable nutrient media and test conditions are described, inter alia, in U.S. Pat. No. 6,221,636, U.S. Pat. No. 5,840,551, U.S. Pat. No. 5,770,409, U.S. Pat. No. 5,605,818, U.S. Pat. No. 5,275,940 and U.S. Pat. No. 4,224,409. It is possible to investigate a large number of mutants in a short time when using suitable robot units as described, for example, in Zimmermann et al. (VDI reports No. 1841, VDI-Verlag, Düsseldorf, Germany 2004, 439–443) or Zimmermann (Chemie Ingenenieur Technik 77 (4), 426–428 (2005)). In this way, it is possible to identify mutants which possess a reduced malate quinone oxidoreductase activity and which secrete amino acids into the nutrient medium to an increased extent as compared with the parental strain or the unmutagenized starting strain. These mutants include, for example, those whose amino acid secretion is increased by at least 0.5%.

Subsequently, DNA is provided or isolated from the mutants and the corresponding polynucleotide is synthesized by means of the polymerase chain reaction using primer pairs which enable the mqo gene, or the mqo allele according to the invention, or the mutation according to the invention at position 111 of the amino acid sequence, to be amplified. The DNA is preferably isolated from those mutants which secrete amino acids to an increased extent.

It is possible to select any primer pairs from the nucleotide sequence located upstream and downstream of the mutation according to the invention, and from the nucleotide sequence which is complementary to it, for this purpose. In this connection, a primer belonging to a primer pair preferably comprises at least 15, at least 18, at least 20, at least 21 or at least 24 consecutive nucleotides selected from the nucleotide sequence between position 1 and 679 of SEQ ID NO: 3. The appurtenant second primer belonging to a primer pair comprises at least 15, at least 18, at least 20, at least 21 or at least 24 consecutive nucleotides selected from the complementary nucleotide sequence of position 2002 and 953 of SEQ ID NO: 3. If it is desired to amplify the coding region, the primer pair is then preferably selected from the nucleotide sequence between position 1 and 349 of SEQ ID NO: 3 and from the complementary nucleotide sequence between position 2002 and 1850 of SEQ ID NO: 3. If it is desired to amplify a part of the coding region, as depicted, for example, in SEQ ID NO: 15, 17 and 19, the primer pair is then preferably selected from the nucleotide sequence between position 351 and 679 of SEQ ID NO: 3 and from the complementary nucleotide sequence between position 1848 and 953 of SEQ ID NO: 3.

Examples of suitable primer pairs are the primer pair mqo-start and mqo-stop, depicted under SEQ ID NO: 11 and SEQ ID NO: 12, or the primer pair mqo-A1 and mqo-E1, depicted under SEQ ID NO: 13 and SEQ ID NO: 14.

The primer can, in addition, be provided with recognition sites for restriction enzymes, with a biotin group or other accessories as described in the prior art. The total length of primer is generally at most 30, 40, 50 or 60 nucleotides.

In general, thermostable DNA polymerases are used for preparing polynucleotides by using PCR to amplify selected sequences, such as the mqo allele according to the invention, from, for example, chromosomal DNA which is initially present. Examples of these DNA polymerases are the *Thermus aquaticus* Taq polymerase, which is marketed, inter alia, by the Qiagen company (Hilden, Germany), the *Thermococcus litoralis* Vent polymerase, which is marketed, inter alia, by the New England Biolabs company (Frankfurt, Germany), or the *Pyrococcus furiosus* Pfu polymerase, which is marketed, inter alia, by the Stratagene company (La Jolla, USA). Preference is given to polymerases which possess proof-reading activity. "Proof-reading" activity means that these polymerases are able to recognize nucleotides which have been incorporated erroneously and to remedy the error by renewed polymerization (Lottspeich and Zorbas, Bioanalytik [Bioanalysis], Spektrum Akademischer Verlag, Heidelberg, Germany (1998)). Examples of polymerases which possess proof-reading activity are the Vent polymerase and the Pfu polymerase.

The conditions in the reaction mixture are set in accordance with the manufacturer's instructions. The polymerases are supplied by the manufacturer, in general together with the customary buffer, which is usually at concentrations of 10–100 mM Tris/HCl and 6–55 mM KCl at pH 7.5–9.3. Magnesium chloride is added at a concentration of 0.5–10 mM if it is not present in the buffer supplied by the manufacturer. In addition, deoxynucleoside triphosphates are added to the reaction mixture at a concentration of 0.1–16.6 mM. The primers are introduced into the reaction medium at a final concentration of 0.1–3 μM and the template DNA is optimally present at from $10^2$ to $10^5$ copies. From $10^6$ to $10^7$ copies may also be used. The appropriate polymerase is added to the reaction mixture in a quantity of 2–5 units. The volume of a typical reaction mixture is 20–100 μl.

As further supplements, bovine serum albumin, Tween-20, gelatin, glycerol, formamide or DMSO can be added to the reaction (Dieffenbach and Dveksler, PCR Primer—A Laboratory Manual, Cold Spring Harbor Laboratory Press, USA 1995).

The typical course of a PCR consists of three different temperature steps which are repeated consecutively. First of all, the reaction is started by increasing the temperature to 92° C.–98° C. for from 4 to 10 minutes in order to denature the DNA which is present. This is then followed, in a reiterating manner, firstly by a step of 10–60 seconds at approximately 92–98° C., for denaturing the DNA, then a step of 10–60 seconds at a specific temperature (annealing temperature), which depends on the primers but has been found by experience to be from 50° C. to 60° C. and can be calculated individually for each primer pair, for binding the primers to the DNA. The skilled person can find precise information in this regard in Rychlik et al. (Nucleic Acids Research 18 (21): 6409–6412). This is then finally followed by a synthesis step for extending the primers (extension) at the activity optimum which is in each case specified for the polymerase, usually in a range from 73° C. to 67° C., preferably from 72° C. to 68° C., depending on the polymerase. The duration of this extension step depends on the efficiency of the polymerase and the length of the PCR product to be amplified. In a typical PCR, this step lasts 0.5–8 minutes, preferably 2–4 minutes. These three steps are repeated from 30 to 35 times, where appropriate up to 50 times. A concluding extension step of 4–10 minutes brings the reaction to an end. The polynucleotides which are prepared in this way are also referred to as amplificates; the terms nucleic acid fragment and nucleic acid molecule are also in common use.

The skilled person can find further instructions and information with regard to the PCR method for example in the manual "PCR Strategies" (Innis, Felfand and Sninsky, Academic Press, Inc., 1995), in the manual from Diefenbach and Dveksler "PCR Primer—a laboratory manual" (Cold Spring Harbor Laboratory Press, 1995), in the manual by Gait "Oligonucleotide synthesis: A Practical Approach" (IRL Press, Oxford, UK, 1984) and in Newton and Graham "PCR" (Spektrum Akademischer Verlag, Heidelberg, Germany, 1994).

The nucleotide sequence is subsequently determined, for example using the chain termination method developed by Sanger et al. (Proceedings of the National Academies of Sciences, USA, 74, 5463–5467 (1977)) together with the modifications specified by Zimmermann et al. (Nucleic Acids Research 18, 1067 pp (1990)) and the polypeptide encoded by this nucleotide sequence is analyzed, in particular with regard to its amino acid sequence. To do this, the nucleotide sequence is fed into a program for translating a DNA sequence into an amino acid sequence. The examples of suitable programs are the "Patentin" program, which can be obtained from patent offices, for example the US Patent Office (USPTO), or the program "Translate Tool", which is available on the ExPASy Proteomics server in the World Wide Web (Gasteiger et al., Nucleic Acids Research 31, 3784–3788 (2003)).

In this way, it is possible to identify mutants whose mqo alleles encode polypeptides which possess malate quinone oxidoreductase enzyme activity and which contain any proteinogenic amino acid apart from L-serine at position 111 or at the corresponding or comparable position. Preference is given to the replacement being with L-phenylalanine or L-alanine. Where appropriate, the amino acid sequence additionally contains a replacement of the amino acid L-alanine with another proteinogenic amino acid, preferably L-serine, at position 201 or at the corresponding or comparable position.

The invention accordingly relates to a mutant of a coryneform bacterium, characterized in that the mutant can be obtained by means of the following steps:

a) treating a coryneform bacterium, which possesses the ability to secrete amino acids, with a mutagenic agent,
b) isolating and propagating the mutant produced in a),
c) preferably determining the ability of the mutant to secrete in a medium, or concentrate in the interior of the cell, at least 0.5% more amino acid than the coryneform bacterium employed in a),
d) preparing nucleic acid from the mutant obtained in b),
e) preparing a nucleic acid molecule using the polymerase chain reaction, the nucleic acid from d) and a primer pair which is composed of a first primer comprising at least 15 consecutive nucleotides selected from the nucleotide sequence between position 1 and 394 of SEQ ID NO: 3 and a second primer comprising at least 15 consecutive nucleotides selected from the complementary nucleotide sequence between position 2002 and 1850 of SEQ ID NO: 3.
f) determining the nucleotide sequence of the nucleic acid molecule obtained in e) and determining the encoded amino acid sequence,
g) where appropriate, comparing the amino acid sequence determined in f) with SEQ ID NO: 6, 8 or 10 or SEQ ID NO: 15, 17 or 19, and
h) identifying a mutant which contains a polynucleotide which encodes a polypeptide which contains any proteinogenic amino acid apart from L-serine, preferably L-phenylalanine or L-alanine, at position 111 or at a comparable position, and, where appropriate, contains any proteinogenic amino acid apart from L-alanine, preferably L-serine, at position 201 or a comparable position.

The mutants produced in this way typically contain one (1) copy of the gnd allele described.

The coding regions of mqo alleles in mutants according to the invention are depicted, by way of example, in SEQ ID NO: 5, 7 and 9. The coding region of the wild-type gene is depicted as SEQ ID NO: 1. SEQ ID NO: 1 contains the nucleobase cytosine at position 332, the nucleobase thymine at position 331 and the nucleobase guanine at position 601. SEQ ID NO: 1 contains the TCT codon, encoding the amino acid L-serine, at position 331 to 333, and contains the GCT codon, encoding the amino acid L-alanine, at position 601 to 603. SEQ ID NO: 5 contains the nucleobase thymine at position 332. As a result of this cytosine to thymine transition, the codon TTT, encoding the amino acid L-phenylalanine, is formed at position 331 to 333. SEQ ID NO: 7 contains the nucleobase guanine at position 331. As a result of this thymine to guanine transversion, the codon GCT, encoding the amino acid L-alanine, is formed at position 331 to 333. In addition to the mutation at position 331, SEQ ID NO: 9 contains the nucleobase thymine at position 601. As a result of this guanine to thiamine transversion, the codon TCT, encoding the amino acid L-serine, is formed at position 601 to 603. In addition to this, the nucleotide sequences depicted in SEQ ID NO: 5, 7 and 9 can contain additional base substitutions which have resulted from the mutagenesis treatment but which are not expressed in any change to the amino acid sequence. In the scientific community, such mutations are also termed silent or neutral mutations. These silent mutations may likewise already be present in the coryneform bacterium which is used for mutagenesis treatment.

The coryneform bacteria which are used for the mutagenesis preferably already possess the ability to secrete the desired amino acid into the nutrient medium or fermentation broth surrounding them or to concentrate it in the interior of the cell.

L-Lysine-producing coryneform bacteria typically possess a feedback-resistant or desensitized aspartate kinase. Feedback-resistant aspartate kinases are understood as being aspartate kinases which exhibit less sensitivity, as compared with the wild form, to inhibition by mixtures of lysine and threonine or mixtures of AEC (aminoethylcysteine) and threonine or lysine on its own or AEC on its own. The genes or alleles encoding these desensitized aspartate kinases are also termed lysC$^{FBR}$ alleles. A large number of lysC$^{FBR}$ alleles which encode aspartate kinase variants, which possess amino acid substitutions as compared with the wild-type protein, are described in the prior art (Table 1). The coding region of the wild-type lysC gene in *Corynebacterium glutamicum*, corresponding to Accession Number AX756575 in the NCBI database, is depicted in SEQ ID NO: 21 while the protein encoded by this gene is depicted in SEQ ID NO: 22.

TABLE 1 lysC$^{FBR}$ alleles encoding feedback-resistant aspartate kinases

| Allele designation | Additional information | Reference | Accession number |
|---|---|---|---|
| lysC$^{FBR}$-E05108 | | JP 1993184366-A (sequence 1) | E05108 |
| lysC$^{FBR}$-E06825 | lysC A279T | JP 1994062866-A (sequence 1) | E06825 |
| lysC$^{FBR}$-E06826 | lysC A279T | JP 1994062866-A (sequence 2) | E06826 |
| lysC$^{FBR}$-E06827 | | JP 1994062866-A (sequence 3) | E06827 |
| lysC$^{FBR}$-E08177 | | JP 1994261766-A (sequence 1) | E08177 |
| lysC$^{FBR}$-E08178 | lysC A279T | JP 1994261766-A (sequence 2) | E08178 |
| lysC$^{FBR}$-E08179 | lysC A279V | JP 1994261766-A (sequence 3) | E08179 |
| lysC$^{FBR}$-E08180 | lysC S301F | JP 1994261766-A (sequence 4) | E08180 |
| lysC$^{FBR}$-E08181 | lysC T308I | JP 1994261766-A (sequence 5) | E08181 |
| lysC$^{FBR}$-E08182 | | JP 1994261766-A (sequence 6) | E08182 |
| lysC$^{FBR}$-E12770 | | JP 1997070291-A (sequence 13) | E12770 |
| lysC$^{FBR}$-E14514 | | JP 1997322774-A (sequence 9) | E14514 |
| lysC$^{FBR}$-E16352 | | JP 1998165180-A (sequence 3) | E16352 |
| lysC$^{FBR}$-E16745 | | JP 1998215883-A (sequence 3) | E16745 |
| lysC$^{FBR}$-E16746 | | JP 1998215883-A (sequence 4) | E16746 |
| lysC$^{FBR}$-I74588 | | US 5688671-A (sequence 1) | I74588 |
| lysC$^{FBR}$-I74589 | lysC A279T | US 5688671-A (sequence 2) | I74589 |
| lysC$^{FBR}$-I74590 | | US 5688671-A (sequence 7) | I74590 |
| lysC$^{FBR}$-I74591 | lysC A279T | US 5688671-A (sequence 8) | I74591 |
| lysC$^{FBR}$-I74592 | | US 5688671-A (sequence 9) | I74592 |
| lysC$^{FBR}$-I74593 | lysC A279T | US 5688671-A (Sequence 10) | I74593 |
| lysC$^{FBR}$-I74594 | | US 5688671-A (Sequence 11) | I74594 |
| lysC$^{FBR}$-I74595 | lysC A279T | US 5688671-A (Sequence 12) | I74595 |
| lysC$^{FBR}$-I74596 | | US 5688671-A (Sequence 13) | I74596 |
| lysC$^{FBR}$-I74597 | lysC A279T | US 5688671-A (Sequence 14) | I74597 |
| lysC$^{FBR}$-X57226 | lysC S301Y | EP0387527 Kalinowski et al., Molecular and General Genetics 224: 317–324 (1990) | X57226 |
| lysC$^{FBR}$-L16848 | lysC G345D | Follettie and Sinskey NCBI Nucleotide Database (1990) | L16848 |
| lysC$^{FBR}$-L27125 | lysC R320G lysC G345D | Jetten et al., Applied Microbiology Biotechnology 43: 76–82 (1995) | L27125 |
| lysC$^{FBR}$ | lysC T311I | WO0063388 (Sequence 17) | |
| lysC$^{FBR}$ | lysC S301F | US3732144 | |
| lysC$^{FBR}$ | lysC S381F | EP0435132 | |
| lysC$^{FBR}$ | lysC S317A | US5688671 (Sequence 1) | |
| lysC$^{FBR}$ | lysC T380I | WO 01/49854 | |

L-Lysine-secreting coryneform bacteria typically+− possess one or more of the amino acid substitutions listed in Table 1.

Preference is given to the following lysC$_{FBR}$ alleles: lysC A279T (replacement of alanine at position 279 in the encoded aspartate kinase protein as depicted in SEQ ID NO: 22 with threonine), lysC A279V (replacement of alanine at position 279 in the encoded aspartate kinase protein as depicted in SEQ ID NO: 22 with valine), lysC S301F (replacement of serine at position 301 in the encoded aspartate kinase protein as depicted in SEQ ID NO: 22 with phenylalanine), lysC T308I (replacement of threonine at position 308 of the encoded aspartate kinase protein as depicted in SEQ ID NO: 22 with isoleucine), lysC S301Y (replacement of serine at position 308 in the encoded aspartate kinase protein as depicted in SEQ ID NO: 22 with tyrosine), lysC G345D (replacement of glycine at position 345 in the encoded aspartate kinase protein as depicted in SEQ ID NO: 22 with aspartic acid), lysC R320G (replacement of arginine at position 320 in the encoded aspartate kinase protein as depicted in SEQ ID NO: 22 with glycine), lysC T311I (replacement of threonine at position 311 in the encoded aspartate kinase protein as depicted in SEQ ID NO: 22 with isoleucine), lysC S381F (replacement of serine at position 381 in the encoded aspartate kinase protein as depicted in SEQ ID NO: 22 with phenylalanine), lysC S317A (replacement of serine at position 317 in the encoded aspartate kinase protein as depicted in SEQ ID NO: 22 with alanine) and lysC T380I (replacement of threonine at position 380 in the encoded aspartate kinase protein as depicted in SEQ ID NO: 22 with isoleucine).

Particular preference is given to the lysC$^{FBR}$ allele lysC T311I (replacement of threonine at position 311 in the encoded aspartate kinase protein as depicted in SEQ ID NO: 22 with isoleucine) and a lysC$^{FBR}$ allele containing at least one substitution selected from the group A279T (replacement of alanine at position 279 in the encoded aspartate kinase protein as depicted in SEQ ID NO: 22 with threonine) and S317A (replacement of serine at position 317 in the encoded aspartate kinase protein as depicted in SEQ ID NO: 22 with alanine).

The lysC$^{FBR}$ allele lysC T311I is present in the strain DM1797, which is deposited in the DSMZ. DM1797 is a mutant of *Corynebacterium glutamicum* ATCC13032.

A mutant designated DM1808, which comprises an mqo allele which encodes a polypeptide in which L-phenylalanine is present at position 111 in the amino acid sequence, was isolated from strain DM1797 in the manner described above. The nucleotide sequence of the mqo allele in mutant DM1808 is depicted as SEQ ID NO: 5 while the amino acid sequence of the encoded polypeptide is depicted as SEQ ID NO: 6.

A mutant which comprises an mqo allele which encodes a polypeptide in which L-alanine is present at position 111 in the amino acid sequence and L-serine is present at position 201 in the amino acid sequence was found in the same way. The nucleotide sequence of the mqo allele in this mutant is depicted as SEQ ID NO: 9 while the amino acid sequence of the encoded polypeptide is depicted as SEQ ID NO: 10.

In addition to this, it is possible to use L-lysine-secreting coryneform bacteria which exhibit an attenuated homoserine dehydrogenase or homoserine kinase, or possess other properties as are known from the prior art.

L-Tryptophan-producing coryneform bacteria typically possess a feedback-resistant to desensitized anthranilate synthase. Feedback-resistant anthranilate synthases are understood as being anthranilate synthases which exhibit less sensitivity, as compared with the wild form, to inhibition (from 5 to 10%, from 10% to 15% or from 10% to 20%) by tryptophan or 5-fluorotryptophan (Matsui et al., Journal of Bacteriology 169 (11): 5330–5332 (1987)) or similar analogs. The genes or alleles encoding these desensitized anthranilate synthases are also termed trpE$^{FBR}$ alleles. Examples of these mutants or alleles are described, for example, in U.S. Pat. No. 6,180,373 and EP0338474.

As compared with the starting strain or parental strain employed, the resulting mutants exhibit an increased secretion or production of the desired amino acid in a fermentation process.

The invention likewise relates to an isolated polynucleotide which encodes a polypeptide which possesses malate quinone oxidoreductase enzyme activity and which contains any proteinogenic amino acid apart from L-serine at position 111 or at a corresponding or comparable position, with replacement with L-phenylalanine or L-alanine being preferred.

The polynucleotide according to the invention can be isolated from a mutant according to the invention.

It is furthermore possible to employ in-vitro methods for mutagenizing the mqo gene. When in-vitro methods are used, isolated polynucleotides which contain a coryneform bacterium gene, preferably the *Cornebacterium glutamicum* wild-type gene described in the prior art, are subjected to a mutagenic treatment.

The isolated polynucleotides can, for example, be isolated total DNA or chromsomal DNA or else amplificates of the mqo gene which are prepared using the polymerase chain reaction (PCR). Such amplificates are also termed PCR products; the terms nucleic acid molecule and nucleic acid fragment are likewise in common use. The skilled person can, inter alia, find instructions for using the polymerase chain reaction to amplify DNA sequences in the manual by Gait: Oligonucleotide Synthesis: A Practical Approach (IRL Press, Oxford, UK, 1984) and in Newton and Graham: PCR (Spektrum Akademischer Verlag, Heidelberg, Germany, 1994). It is likewise possible to first of all incorporate the mqo gene to be mutagenized into a vector, for example a bacteriophage or a plasmid.

Suitable methods for in-vitro mutagenesis include treatment with hydroxylamine as described by Miller (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992), the use of mutagenic oligonucleotides (T. A. Brown: Gentechnologie für Einsteiger [Recombinant DNA Technology for those entering the field], Spektrum Akademischer Verlag, Heidelberg, 1993 and R. M. Horton: PCR-Mediated Recombination and Mutagenesis, Molecular Biotechnology 3, 93–99 (1995)) and the use of a polymerase chain reaction while employing a DNA polymerase which exhibits a high error rate. An example of such a DNA polymerase is the Mutazyme DNA polymerase (GeneMorph PCR mutagenesis kit, No. 600550) supplied by Stratagene (La Jolla, Calif., USA).

Further instructions and reviews with regard to generating mutations in vivo or in vitro can be found in the prior art and known textbooks of genetics and molecular biology, such as the textbook by Knippers ("Molekulare Genetik [Molecular Genetics]", 6$^{th}$ edition, Georg Thieme Verlag, Stuttgart, Germany, 1995), that by Winnacker ("Gene und Klone [Genes and Clones]", VCH Verlagsgesellschaft, Weinheim, Germany, 1990) or that by Hagemann ("Allgemeine Genetik [General Genetics]", Gustav Fischer Verlag, Stuttgart, 1986).

The invention furthermore relates to an isolated polynucleotide which encodes a polypeptide which possesses malate quinone oxidoreductase enzyme activity and which comprises the amino acid sequence depicted in SEQ ID NO: 2, with any proteinogenic amino acid apart from L-serine being present at position 111 in the amino acid sequence. Preference is given to the replacement being with L-phenylalanine or L-alanine. Where appropriate, the amino acid sequence of the polypeptide additionally contains a replacement of the amino acid L-alanine with another amino acid, preferably L-serine, at position 201.

The invention furthermore relates to an isolated polynucleotide which encodes a polypeptide which possesses malate quinone oxidoreductase enzyme activity and which comprises an amino acid sequence whose length is 500 amino acids, with any proteinogenic L-amino acid apart from L-serine, preferably L-phenylalanine or L-alanine, being present at position 111.

The invention furthermore relates to an isolated polynucleotide which encodes a polypeptide which possesses malate quinone oxidoreductase enzyme activity and which contains, from position 106 to 116 in its amino acid sequence, the amino acid sequence corresponding to position 106 to 116 in SEQ ID NO: 6 or 8. The amino acid sequence of the encoded polypeptide preferably contains an amino acid sequence corresponding to position 96 to 126 in SEQ ID NO: 6 or 8 or position 81 to 141 in SEQ ID NO: 6 or 8 or position 66 to 156 in SEQ ID NO: 6 or 8 or position 51 to 181 in SEQ ID NO: 6 or 8 or position 21 to 201 in SEQ ID NO: 6, 8 or 10 or position 2 to 301 in SEQ ID NO: 6, 8 or 10 or position 2 to 401 in SEQ ID NO: 6, 8 or 10 or position 2 to 499 in SEQ ID NO: 6, 8 or 10 or position 2 to 500 in SEQ ID NO: 6, 8 or 10. Very particular preference is given to the length of the encoded polypeptide being 500 amino acids.

The invention furthermore relates to an isolated polynucleotide which encodes a polypeptide which possesses malate quinone oxidoreductase enzyme activity and which contains any proteinogenic amino acid apart from L-serine, preferably L-phenylalanine or L-alanine, at position 111 in the amino acid sequence or at a corresponding or comparable position, and which comprises a nucleotide sequence which is identical to the nucleotide sequence of a polynucleotide which can be obtained by a polymerase chain reaction (PCR) using the primer pair whose nucleotide sequences in each case comprise at least 15 consecutive nucleotides which are selected from the nucleotide sequence between position 1 and 349 of SEQ ID NO: 3 and from the complementary nucleotide sequence between position 2002 and 1850 of SEQ ID NO: 3. Two examples of suitable primer pairs are depicted in SEQ ID NO: 11 and SEQ ID NO: 12 and in SEQ ID NO: 13 and SEQ ID NO: 14. The starting material (template) employed is chromosomal DNA from coryneform bacteria which have preferably been subjected to a mutagenic treatment. Particular preference is given to the chromosomal DNA of the genus *Corynebacterium* and very particular preference is given to that of the species *Corynebacterium glutamicum*.

The invention furthermore relates to an isolated polynucleotide which hybridizes, under stringent conditions, with a nucleotide sequence which is complementary to SEQ ID NO: 5, 7 or 9 and encodes a polypeptide which possesses malate quinone oxidoreductase enzyme activity and which contains any proteinogenic amino acid apart from L-serine, preferably L-phenylalanine or L-alanine, at position 111 in the amino acid sequence or at a corresponding or comparable position and, where appropriate, contains any proteinogenic amino acid apart from L-alanine, preferably L-serine, at a position corresponding to position 201.

The skilled person can, inter alia, find instructions for hybridizing nucleic acids or polynucleotides in the manual "The DIG System Users Guide for Filter Hybridization" published by Boehringer Manheim GmbH (Mannheim, Germany, 1993) and in Liebl et al. (International Journal of Systematic Bacteriology 41: 255–260 (1991)). The hybridization takes place under stringent conditions, i.e. the only hybrids which are formed are those in which the probe, i.e. a polynucleotide comprising the nucleotide sequence which is complementary to SEQ ID NO: 5, 7 or 9, and the target sequence, i.e. the polynucleotides treated with a probe, are at least 90% identical. It is known that the stringency of the hybridization, including the washing steps, is influenced or determined by varying the buffer composition, the temperature and the salt concentration. The hybridization reaction is generally carried out at a stringency which is low as compared with the washing steps (Hybaid Hybridisation Guide, Hybaid Limited, Teddington, UK, 1996).

It is possible, for example, to use a buffer corresponding to 5×SSC buffer, at a temperature of approx. 50° C.–68° C., for the hybridization reaction. In this reaction, probes can also hybridize with polynucleotides which exhibit less than 90% identity to the nucleotide sequence of the probe employed. These hybrids are less stable and are removed by washing under stringent conditions. This can be achieved, for example, by lowering the salt concentration down to 2×SSC and, where appropriate, subsequently down to 0.5× SSC (The DIG System User's Guide for Filter Hybridisation, Boehringer Manheim GmbH (Mannheim, Germany, 1995), with the temperature being set at approx. 50° C.–68° C., approx. 52° C.–68° C., approx. 54° C.–68° C., approx. 56° C.–68° C., approx. 58° C.–68° C., approx. 60° C.–68° C., approx. 62° C.–68° C., approx. 64° C.–68° C. or approx. 66° C.–68° C. Temperature ranges of approx. 64° C.–68° C. or approx. 66° C.–68° C. are preferred. It is possible, where appropriate, to lower the salt concentration down to a concentration corresponding to 0.2×SSC or 0.1×SSC. Where appropriate, the SSC buffer contains sodium dodecyl sulfate (SDS) at a concentration of 0.1%. By increasing the hybridization temperature stepwise from 50° C. to 68° C., in steps of approx. 1–2° C., it is possible to isolate polynucleotide fragments which possess at least 90% or at least 91%, preferably at least 92% or at least 93%, or at least 94%, or at least 95%, or at least 96%, and very particularly preferably at least 97%, or at least 98%, or at least 99%, identity to the sequence, or the complementary sequence, of the probe employed and encode a polypeptide which possesses malate quinone oxidoreductase enzyme activity and contains the amino acid substitution according to the invention. The nucleotide sequence of the polynucleotide which is obtained in this way is determined using known methods. Further instructions with regard to hybridization can be obtained in the form of kits (e.g. DIG Easy Hyb supplied by Roche Diagnostics GmbH, Mannheim, Germany, catalog No. 1603558). The nucleotide sequences which are thus obtained encode polypeptides which possess malate quinone oxidoreductase enzyme activity, which are at least 90%, preferably at least 92%, or at least 94%, or at least 96%, and very particularly preferably at least 97%, or at least 98%, or at least 99%, identical to the amino acid sequence in SEQ ID NO: 6 or SEQ ID NO: 8, and contain the amino acid substitution according to the invention.

The invention furthermore relates to an isolated polynucleotide which encodes a polypeptide which possesses malate quinone oxidoreductase enzyme activity, which contains any amino acid apart from L-serine at position 111 or a corresponding or comparable position in the amino acid sequence, with preference being given to replacement with L-phenylalanine or L-alanine, and which comprises an amino acid sequence which is also at least 90%, preferably at least 92%, or at least 94%, or at least 96%, and very particularly preferably at least 97%, or at least 98%, or at least 99%, identical to the amino acid sequence in SEQ ID NO: 6 or 8. An example of a polypeptide which possesses malate quinone oxidoreductase enzyme activity and which comprises an amino acid sequence which is at least 99% identical to that in SEQ ID NO: 8 is shown in SEQ ID NO: 10.

The invention furthermore relates to an isolated polynucleotide which encodes a polypeptide which possesses malate quinone oxidoreductase enzyme activity and which contains any amino acid apart from L-serine at position 11 or a corresponding or comparable position in the amino acid sequence, with preference being given to replacement with L-phenylalanine or L-alanine, and which comprises a nucleotide sequence which is also at least 90%, preferably at least 92%, or at least 94%, or at least 96%, and very particularly preferably at least 97%, or at least 98%, or at least 99%, identical to the nucleotide sequence in SEQ ID NO: 5 or 7. An example of a polynucleotide which encodes a polypeptide according to the invention possessing malate quinone oxidoreductase enzyme activity and which possesses a nucleotide sequence which is at least 99% identical to that in SEQ ID NO: 7 is shown in SEQ ID NO: 9.

In addition to this, preference is given to isolated polynucleotides which encode the polypeptide which possesses malate quinone oxidoreductase enzyme activity, which contains any amino acid apart from L-serine, preferably L-phenylalanine or L-alanine, at position 111 of the amino acid sequence or at a corresponding or comparable position and which comprises at least one sequence motif or one amino acid sequence selected from the group Trp-Asn-Asn-Ala-Gly-Thr-Gly-His-Sal-Ala-Leu and Bra-Leu-Gly-Ali-Ser-Pro-Gly-Ala-Ser. The designation "Bra" stands for the amino acids Ile or Leu, while the designation "Sal" stands for the amino acids Ser or Ala and the designation "Ali" stands for the amino acids Ala or Gly.

The invention furthermore relates to an isolated polynucleotide which encodes a polypeptide which possesses malate quinone oxidoreductase enzyme activity and which comprises the amino acid sequence in SEQ ID NO: 6, 8 or 10. Where appropriate, the encoded polypeptide contains one (1) or more conservative amino acids substitution(s). Preference is given to the polypeptide containing at most two (2), at most three (3), at most four (4) or at most five (5) conservative amino acid substitutions.

The invention furthermore relates to an isolated polynucleotide which encodes the polypeptide which possesses malate quinone oxidoreductase enzyme activity and which comprises the amino acid sequence depicted in SEQ ID NO: 6, 8 or 10 including an extension at the N terminus or C terminus by at least one (1) amino acid. This extension consists of not more than 50, 40, 30, 20, 10, 5, 3 or 2 amino acids or amino acid residues.

The invention finally also relates to mqo alleles which encode polypeptide variants of SEQ ID NO: 6, 8 or 10 which contain one or more insertions or deletions. These variants contain at most 5, at most 4, at most 3 or at most 2 insertions or deletions of amino acids. The sequence motifs Trp-Asn-Asn-Ala-Gly-Thr-Gly-His-Sal-Ala-Leu and Bra-Leu-Gly-Ali-Ser-Pro-Gly-Ala-Ser are preferably not disrupted by these insertions/deletions.

The invention furthermore relates to an isolated polynucleotide which comprises the nucleotide sequence as depicted in SEQ ID NO: 5, 7 or 9.

The invention finally relates to an isolated polynucleotide which comprises the mqo allele of the mutant DM1808.

The invention also relates to an isolated polynucleotide which comprises a part of the coding region of an mqo allele according to the invention, with the isolated polynucleotide in every case comprising the part of the coding region which contains the amino acid substituted at position 111 in the amino acid sequence of the encoded polypeptide.

In particular, the polynucleotide comprises a nucleic acid molecule or DNA fragment which encodes at least one amino acid sequence corresponding to position 95 to 127 in SEQ ID NO: 2 or which encodes at least one amino acid sequence corresponding to position 79 to 144 in SEQ ID NO: 2, or which encodes at least one amino acid sequence corresponding to position 62 to 160 in SEQ ID NO: 2, or which encodes at least one amino acid sequence corresponding to position 45 to 177 in SEQ ID NO: 2, or which encodes at least one amino acid sequence corresponding to position 27 to 194 in SEQ ID NO: 2, or which encodes at least one amino acid sequence corresponding to position 11 to 211 in SEQ ID NO: 2, or which encodes at least one amino acid sequence corresponding to position 2 to 250 in SEQ ID NO: 2, or which encodes at least one amino acid sequence corresponding to position 2 to 375 in SEQ ID NO: 2, or which encodes at least one amino acid sequence corresponding to position 2 to 495 in SEQ ID NO: 2, or comprises a corresponding reading frame, with any proteinogenic amino acid apart from L-serine, preferably L-phenylalanine or L-alanine, being present at the position corresponding to 111 in SEQ ID NO: 2, and with, where appropriate, any proteinogenic amino acid apart from L-alanine, preferably L-serine, being present at the position corresponding to 201.

An example of a reading frame according to the invention, which comprises a polynucleotide which encodes at least the amino acid sequence from position 95 to 127 in accordance with SEQ ID NO: 2, with any proteinogenic amino acid apart from L-serine being present at the position corresponding to 111 in the amino acid sequence, is that which follows:

```
cag gtt tcc cgt cag ttc tgg tct cac ctc gtt gaa gag gga gtg ctg nnn
Gln Val Ser Arg Gln Phe Trp Ser His Leu Val Glu Glu Gly Val Leu Xaa
95              100             105             110 gat cct aag gaa ttc atc aac cct gtt cct cac gta tct ttc ggc cag
Asp Pro Lys Glu Phe Ile Asn Pro Val Pro His Val Ser Phe Gly Gln
            115             120             125
```

It is also depicted as SEQ ID NO: 15. The amino acid sequence encoded by this reading frame is depicted as SEQ ID NO: 16.

Preference is given to nucleic acid molecules which encode at least one amino acid sequence corresponding to position 95 to 127 in SEQ ID NO: 6, 8 or 10, or at least corresponding to position 79 to 144 in SEQ ID NO: 6, 8 or 10, or at least corresponding to position 62 to 160 in SEQ ID NO: 6, 8 or 10, or at least corresponding to position 45 to 177 in SEQ ID NO: 6, 8 or 10, or at least corresponding to position 27 to 194 in SEQ ID NO: 6, 8 or 10, or at least corresponding to position 11 to 211 in SEQ ID NO: 6, 8 or 10, or at least corresponding to position 2 to 250 in SEQ ID NO: 6, 8 or 10, or at least corresponding to position 2 to 375 in SEQ ID NO: 6, 8 or 10, or at least corresponding to position 2 to 495 in SEQ ID NO: 6, 8 or 10.

An example of a reading frame according to the invention which comprises a polynucleotide which encodes at least the amino acid sequence corresponding to position 95 to 127 in SEQ ID NO: 6 is that which follows:

```
cag gtt tcc cgt cag ttc tgg tct cac ctc gtt gaa gag gga gtg ctg ttt
Gln Val Ser Arg Gln Phe Trp Ser His Leu Val Glu Glu Gly Val Leu Phe
95              100             105             110 gat cct aag gaa ttc atc aac cct gtt cct cac gta tct ttc ggc cag
Asp Pro Lys Glu Phe Ile Asn Pro Val Pro His Val Ser Phe Gly Gln
            115             120             125
```

The reading frame is likewise depicted as SEQ ID NO: 17. SEQ ID NO: 18 shows the amino acid sequence which is encoded by this reading frame.

An example of a reading frame according to the invention which comprises a polynucleotide which encodes at least the amino acid sequence corresponding to position 95 to 127 in SEQ ID NO: 8 or 10 is that which follows:

```
cag gtt tcc cgt cag ttc tgg tct cac ctc gtt gaa gag gga gtg ctg gct
Gln Val Ser Arg Gln Phe Trp Ser His Leu Val Glu Glu Gly Val Leu Ala
95              100                 105             110 gat cct aag gaa ttc atc aac cct gtt cct cac gta tct ttc ggc cag
Asp Pro Lys Glu Phe Ile Asn Pro Val Pro His Val Ser Phe Gly Gln
            115             120             125
```

The reading frame is likewise depicted as SEQ ID NO: 19. SEQ ID NO: 20 shows the amino acid sequence which is encoded by this reading frame.

Very particular preference is given to nucleic acid molecules which comprise at least one nucleotide sequence corresponding to position 283 to 381 in SEQ ID NO: 5, 7 or 9, or at least one nucleotide sequence corresponding to position 235 to 432 in SEQ ID NO: 5, 7 or 9, or at least one nucleotide sequence corresponding to position 184 to 480 in SEQ ID NO: 5, 7 or 9, or at least one nucleotide sequence corresponding to position 133 to 531 in SEQ ID NO: 5, 7 or 9, or at least one nucleotide sequence corresponding to position 85 to 582 in SEQ ID NO: 5, 7 or 9, or at least one nucleotide sequence corresponding to position 28 to 630 in SEQ ID NO: 5, 7 or 9, or at least one nucleotide sequence corresponding to position 4 to 753 in SEQ ID NO: 5, 7 or 9, or at least one nucleotide sequence corresponding to position 4 to 1125 in SEQ ID NO: 5, 7 or 9, or at least one nucleotide sequence corresponding to position 4 to 1485 in SEQ ID NO: 5, 7 or 9.

In addition to this, the reading frames according to the invention, as are shown, by way of example, as nucleotide sequences in SEQ ID NO: 15, 17 and 19 and in the form of the encoded amino acid sequences in SEQ ID NO: 16, 18 and SEQ ID NO: 20, can contain one or more mutations which lead(s) to one or more conservative amino acid substitutions. Preference is given to the mutations leading to at most 4%, to at most 2% or to at most 1% conservative amino acid substitutions. In addition, the reading frames according to the invention can contain one or more silent mutations. Preference is given to the reading frames according to the invention containing at most 4%, and particularly preferably at most 2% to at most 1%, silent mutations.

The isolated polynucleotides according to the invention can be used for preparing recombinant strains of microorganisms which release amino acids into the medium surrounding them, or accumulate amino acids in the interior of the cell, in a manner which is superior to that of the starting or parental strain.

A widespread method for incorporating mutations into genes of coryneform bacteria is that of allele substitution, which is also known under the name "gene replacement". In this method, a DNA fragment which contains the mutation of interest is transferred into the desired strain of a coryneform bacterium and the mutation is incorporated into the chromosome of the desired strain by means of at least two recombination events or "cross-over" events, or a gene sequence which is present in the strain in question is replaced with the mutated sequence.

Schwarzer and Pühler (Bio/Technology 9, 84–87 (1991) used this method to incorporate a lysA allele which carried a deletion, and to incorporate a lysA allele which carried an insertion, into the C. glutamicum chromosome in place of the wild-type gene. Schäfer et al. (Gene 145, 69–73 (1994)) used this method to incorporate a deletion into the C. glutamicum hom-thrB operon. Nakagawa et al. (EP 1108790) used this method to incorporate a variety of mutations, based on the isolated alleles, into the C. glutamicum chromosome. In this way, Nakagawa et al. succeeded in incorporating a mutation designated Val59Ala into the homoserine dehydrogenase gene (hom), a mutation designated Thr311Ile into the aspartate kinase gene (lysC or ask), a mutation designated Pro458Ser into the pyruvate carboxylase gene (pyc) and a mutation designated Ala213Thr into the glucose 6-phosphate dehydrogenase gene (zwf), in C. glutamicum strains.

A polynucleotide according to the invention which comprises the entire coding region, as shown, for example, in SEQ ID NO: 5, 7 or 9, or which comprises a part of the coding region, as for example the nucleotide sequence which encodes at least the amino acid sequence corresponding to position 95 to 127 in SEQ ID NO: 6, 8 or 10 and which is depicted as SEQ ID NO: 15, 17 or 19, can be used for a method according to the invention. The part of the coding region according to SEQ ID NO: 15, 17 and 19 is 99 nucleobases in length. Preference is given to those parts of the coding region whose length is ≧195 nucleobases, such as nucleic acid molecules which encode at least one amino acid sequence corresponding to position 79 to 144 in SEQ ID NO: 6, 8 or 10. Very particular preference is given to those parts of the coding region whose length is ≧295 nucleobases, such as nucleic acid molecules which encode at least one amino acid sequence corresponding to position 62 to 160 in SEQ ID NO: 6, 8 or 10.

In this method, the DNA fragment containing the mutation of interest is typically present in a vector, in particular in a plasmid, which is preferably not replicated, or only replicated to a limited extent, by the strain which is to be provided with the mutation. In general, a bacterium of the genus Escherichia, preferably of the species Escherichia coli, is used as an auxiliary or intermediate host in which the vector can be replicated.

Examples of these plasmid vectors are the pK*mob and pK*mobsacB vectors, such as pK18mobsacB, described by Schäfer et al. (Gene 145, 69–73 (1994)) and the vectors described in WO 02/070685 and WO 03/014362. These vectors can replicate in Escherichia coli but not in coryneform bacteria. Vectors which contain a gene which acts in a conditionally negatively dominant manner, such as the sacB gene (levan sucrase gene) in, for example, Bacillus, or the galK (galactose kinase) gene in, for example, Escherichia coli, are particularly suitable. (A gene which acts in a conditionally negatively dominant manner is understood as being a gene which, under particular conditions, is disadvantageous, for example toxic, for the host but which, under other conditions, does not have any negative effects on the host which is carrying the gene.) These vectors make it possible to select for recombination events in which the vector is eliminated from the chromosome. Furthermore, Nakamura et al. (U.S. Pat. No. 6,303,383) have described, for coryneform bacteria, a temperature-sensitive plasmid which is only able to replicate at temperatures below 31° C.

The vector is subsequently transferred into the coryneform bacterium by conjugation, for example in accordance with the method of Schäfer (Journal of Bacteriology 172, 1663–1666 (1990)) or transformation, for example in accordance with the method of Dunican and Shivnan (Bio/Technology 7, 1067–1070 (1989)) or the method of Thierbach et al. (Applied Microbiology and Biotechnology 29, 356–362 (1988)). Where appropriate, the DNA can also be transferred by means of particle bombardment.

Following homologous recombination, by means of a first cross-over event which brings about integration, and a suitable second cross-over event which brings about an excision, in the target gene or in the target sequence, the mutation is incorporated and a recombinant bacterium is obtained.

It is possible, inter alia, to use the method of Southern blotting hybridization, of polymerase chain reaction or of sequence determination, or the fluorescence resonance energy transfer (FRET) method (Lay et al. Clinical Chemistry 43, 2262–2267 (1997)) or methods of enzymology, to identify and characterize the resulting strains.

Accordingly, the invention also relates to a process for preparing a coryneform bacterium, in which process
a) a polynucleotide according to the invention is transferred into a coryneform bacterium,
b) the malate quinone oxidoreductase gene which is present in the chromosome of the coryneform bacterium, and which encodes an amino acid sequence containing L-serine at position 111 or a comparable position in the amino acid sequence, is replaced with the polynucleotide from a), which polynucleotide encodes an amino acid sequence which possesses another L-amino acid, preferably L-phenylalanine or L-alanine, at position 111 or a comparable position in the amino acid sequence, and, where appropriate, possesses any proteinogenic amino acid apart from L-alanine, preferably the amino acid L-serine, at position 201, and
c) the coryneform bacterium which is obtained in accordance with step a) and b) is propagated.

This thereby results in recombinant coryneform bacterium which comprises an mqo allele according to the invention in place of the wild-type mqo gene.

Another process according to the invention for preparing a microorganism comprises
a) transferring a polynucleotide according to the invention, which encodes a polypeptide possessing malate quinone oxidoreductase enzyme activity, into a microorganism,
b) replicating the polynucleotide in the microorganism, and
c) propagating the microorganism which is obtained in accordance with step a) and b).

This thereby results in a recombinant microorganism which comprises at least one (1) copy, or several copies, of a polynucleotide according to the invention which encodes a malate quinone oxidoreductase which contains any proteinogenic amino acid apart from L-serine, with replacement with L-phenylalanine with L-alanine being preferred, at position 111 or a comparable position in the amino acid sequence of the encoded polypeptide. Where appropriate, the polypeptide contains any proteinogenic amino acid apart from L-alanine, preferably the amino acid L-serine, at position 201 or a comparable position.

Accordingly, the invention also relates to hosts or host cells, preferably microorganisms, particularly preferably coryneform bacteria and bacteria of the genus *Escherichia*, which comprise the polynucleotides according to the invention. The invention likewise relates to microorganisms which are prepared using the isolated polynucleotide. These microorganisms or bacteria are also termed recombinant microorganisms or recombinant bacteria. In the same way, the invention relates to vectors which contain the polynucleotides according to the invention. Finally, the invention also relates to hosts which comprise these vectors. Where appropriate, the isolated polynucleotides according to the invention can be used for achieving overexpression of the proteins/polypeptides which they encode.

"Overexpression" is understood generally as meaning an increase in the intracellular concentration or activity of a ribonucleic acid, of a protein or of an enzyme. In the case of the present invention, mqo alleles or polynucleotides which encode malate quinone oxidoreductases which contain any proteinogenic amino acid apart from L-serine at position 111 in the amino acid sequence of the encoded polypeptide, with replacement with L-phenylalanine or L-alanine being preferred, are overexpressed. Where appropriate, the encoded protein also contains a replacement of L-alanine with another proteinogenic amino acid, preferably L-serine, at position 201 in the amino acid sequence.

It is known that N-terminal amino acids, in particular the N-terminal methionine, can be cleaved off the formed polypeptide by enzymes, i.e. what are termed aminopeptidases, which are intrinsic to the host.

The abovementioned increase in the concentration or activity of a gene product can be achieved, for example, by increasing the copy number of the corresponding polynucleotides by at least one copy.

A widespread method for increasing the copy number consists in incorporating the corresponding gene or allele into a vector, preferably a plasmid, which is replicated by a coryneform bacterium. Examples of suitable plasmid vectors are pZ1 (Menkel et al., Applied and Environmental Microbiology (1989) 64: 549–554) or the pSELF vectors described by Tauch et al. (Journal of Biotechnology 99, 79–91 (2002)). A review article on the topic of plasmids in *Corynebacterium glutamicum* can be found in Tauch et al. (Journal of Biotechnology 104, 27–40 (2003)).

Another widespread method for achieving overexpression is the chromosomal gene amplification method. In this method, at least one additional copy of the gene or allele of interest is inserted into the chromosome of a coryneform bacterium.

In one embodiment, as described, for example, in Reinscheid et al. (Applied and Environmental Microbiology 60, 126–132) in the case of the hom-thrB operon, a plasmid which does not replicate in *C. glutamicum*, and which contains the gene of interest, is transferred into a coryneform bacterium. Following homologous recombination by means of a cross-over event, the resulting strain comprises at least two copies of the gene or allele concerned.

In another embodiment, which is described in WO 03/040373 and US-2003-0219881-A1, one or more copy (ies) of the gene of interest is/are inserted into a desired site in the *C. glutamicum* chromosome by means of at least two recombination events. In this way, a copy of a lysC allele encoding an L-lysine-insensitive aspartate kinase was, for example, incorporated into the *C. glutamicum* gluB gene.

In another embodiment, which is described in WO 03/014330 and US-2004-0043458-A1, at least one additional copy of the gene of interest is incorporated at the natural site, preferably in tandem formation in relation to the gene or allele which is already present, by means of at least two recombination events. In this way, a tandem duplication of a lysC$^{FBR}$ allele was, for example, achieved at the natural lysC gene locus.

Another method for achieving overexpression consists in functionally (operably) linking the corresponding gene or allele to a promoter or an expression cassette. Suitable promoters for *Corynebacterium glutamicum* are described, for example, in the review article by Patek et al. (Journal of Biotechnology 104(1–3), 311–323 (2003). It is furthermore possible to use promoters T3, T7, SP6, M13, lac, tac and trc, which are sufficiently well known and are described by Amann et al. (Gene 69(2), 301–315 (1988)) and Amann and Brosius (Gene 40(2–3), 183–190 (1985)). Such a promoter can, for example, be inserted upstream, typically at a distance of approximately 1–500 nucleotides from the start codon, of the mqo allele of a recombinant coryneform bacterium which contains another proteinogenic amino acid in place of the amino acid L-serine which is naturally present at position 111. Such a promoter can, of course, likewise be inserted upstream of the mqo allele of a mutant according to the invention. It is furthermore possible to link an isolated polynucleotide according to the invention, which encodes a malate quinone oxidoreductase variant according to the invention, to a promoter and to incorporate the resulting expression unit into an extrachromosomally replicating plasmid or into the chromosome of a coryneform bacterium.

In addition to this, the promoter and regulatory region or the ribosome binding site which is located upstream of the structural gene can be mutated. Expression is also improved by measures taken to extend the lifetime of the mRNA. In addition, the activity of the enzyme is augmented by preventing the enzyme protein from being broken down. As an alternative, overexpression of the gene or allele concerned can also be achieved by altering the composition of the medium and the way in which the culture is conducted.

In general, the measures taken to achieve overexpression increase the activity or concentration of the corresponding protein/polypeptide by at least 10%, 25%, 50%, 75%, 100%, 150%, 200%, 300%, 400% or 500%, or at most up to 1000% or 2000%, based on the activity or concentration of the protein in the starting microorganism or parental strain. A starting microorganism or parental strain is understood as being a microorganism on which the measures of the invention are carried out.

A method for determining the enzymic activity of malate quinone oxidoreductase is described in Molenaar et al. (Journal of Bacteriology 182(24), 6884–6891 (2000)).

The concentration of the protein can be determined by means of 1-dimensional or 2-dimensional protein gel fractionation and subsequent optical identification of the protein concentration in the gel using appropriate analytical software. A customary method for preparing protein gels in the case of coryneform bacteria, and for identifying the proteins, is the procedure described by Hermann et al. (Electrophoresis, 22:1712–23 (2001)). The protein concentration can also be determined by means of Western blot hybrization using an antibody which is specific for the protein to be detected (Sambrook et al., Molecular cloning: a laboratory manual. 2$^{nd}$ Ed. Cold Spring Harbor Laboratory Press, Cold Spring Harbor, N.Y., 1989), with this being followed by optical analysis using appropriate software for the purpose of determining the concentration (Lohaus and Meyer (1998) Biospektrum [Biospectrum] 5:32–39; Lottspeich, Angewandte Chemie [Applied Chemistry] 111: 2630–2647 (1999)).

Accordingly, the invention relates to a process for overexpressing the malate quinone oxidoreductases according to the invention. A process according to the invention for overexpressing consists, inter alia, in increasing the copy number of a polynucleotide according to the invention, which encodes a malate quinone oxidoreductase variant in which any proteinogenic amino acid apart from L-serine is present at position 111 or a corresponding position in the encoded amino acid sequence, by at least one (1) or more copies. Another process according to the invention consists in functionally linking a promoter to the polynucleotide.

The invention furthermore relates to microorganisms which exhibit an elevated concentration or activity of the malate quinone oxidoreductase variants according to the invention in the interior of their cells.

In addition, it can be advantageous, for improving the production of L-amino acids, to overexpress one or more enzymes of the relevant biosynthetic pathway, of glycolysis, of anaplerosis, of the citric acid cycle, of the pentose phosphate cycle or of amino acid export, and, where appropriate, regulatory proteins, in the mutants or recombinant strains according to the invention. In general, preference is given to using endogenous genes.

"Endogenous genes" or "endogenous nucleotide sequences" are understood as meaning the genes or nucleotide sequences or alleles which are present in the population of a species.

Thus, for the purpose of preparing L-lysine, it is possible to overexpress one or more of the genes selected from the group a dapA gene encoding a dihydropicolinate synthase, as, for example, the *Corynebacterium glutamicum* wild-type dapA gene described in EP 0 197 335, a zwf gene encoding a glucose 6-phosphate dehydrogenase, as, for example, the *Corynebacterium glutamicum* wild-type zwf gene described in JP-A-09224661 and EP-A-1108790, the *Corynebacterium glutamicum* zwf alleles which are described in US-2003-0175911-A1 and which encode a protein in which, for example, the L-alanine at position 243 in the amino acid sequence is replaced with L-threonine or in which the L-aspartic acid at position 245 is replaced with L-serine, a pyc gene encoding a pyruvate carboxylase, as, for example, the *Corynebacterium glutamicum* wild-type pyc gene described in DE-A-198 31 609 and EP 1108790, the *Corynebacterium glutamicum* pyc allele which is described in EP 1 108 790 and which encodes a protein in which L-proline at position 458 in the amino acid sequence is replaced with L-serine, the *Corynebacterium glutamicum* pyc alleles which are described in WO 02/31158 and which encode proteins which, according to claim 1, carry one or more of the amino acid substitutions selected from the group L-glutamic acid at position 153 replaced with L-aspartic acid, L-alanine at position 182 replaced with L-serine, L-alanine at position 206 replaced with L-serine, L-histidine at position 227 replaced with L-arginine, L-arginine at position 452 replaced with glycine and L-aspartic acid at position 1120 replaced with L-glutamic acid (FIG. 2A in WO 02/31158 specifies two different start positions for the pyruvate carboxylase, which positions differ by a length corresponding to 17 amino acids. Accordingly, position 153 in accordance with claim 1 in WO 02/31158 corresponds to position 170 in FIG. 2A in WO 02/31158, while position 182 in accordance with claim 1 corresponds to position 199 in FIG. 2A, position 206 in accordance with claim 1 corresponds to position 223 in FIG. 2A, position 227 in accordance with claim 1 corresponds to position 244 in FIG. 2A, position 452 in accordance with claim 1 corresponds to position 469 in FIG. 2A and position 1120 in accordance with claim 1 corresponds to position 1137 in FIG. 2B. FIG. 2A in WO 02/31158 furthermore specifies a replacement of the amino acid A (alanine) with G (glycine) at position 472. Position 472 in the protein having the N-terminal sequence MTA corresponds to position 455 in the protein having the N-terminal sequence MST as shown in FIG. 2A. FIG. 2B in WO 02/31158 also specifies a replacement of the amino acid D (aspartic acid) with E (glutamic acid) at position 1133 in the protein having the N-terminus MTA.), a lysC gene encoding an aspartic kinase, as, for example, that Corynebacterium glutamicum wild-type lysC gene which is described as SEQ ID NO: 281 in EP-A-1108790 (see also Accession Numbers AX120085 and 120365) and that which is described as SEQ ID NO: 25 in WO 01/00843 (see Accession Number AX063743), a lysC$^{FBR}$ allele, in particular in accordance with Table 1, which encodes a feedback-resistant aspartate kinase variant, a lysE gene which encodes a lysine export protein, as, for example, the Corynebacterium glutamicum wild-type lysE gene which is described in DE-A-195 48 222, the Corynebacterium glutamicum wild-type zwa1 gene encoding the Zwa1 protein (U.S. Pat. No. 6,632,644).

In addition to using the alleles of the mqo gene according to the invention, it can also be advantageous, for the purpose of producing L-lysine, to simultaneously attenuate or eliminate one or more of the endogenous genes selected from the group a pgi gene encoding glucose 6-phosphate isomerase, as, for example, the Corynebacterium glutamicum pgi gene which is described in U.S. Pat. Nos. 6,586,214 and US 6,465,238, a hom gene encoding homoserine dehydrogenase, as, for example, the Corynebacterium glutamicum hom gene described in EP-A-0131171, a thrB gene encoding homoserine kinase, as, for example, the Corynebacterium glutamicum thrB gene described by Peoples et al. (Molecular Microbiology 2 (1988): 63–72), and a pfkB gene encoding phosphofructokinase, as, for example, the Corynebacterium glutamicum pfkB gene described in WO 01/00844 (Sequence No. 57).

Where appropriate, the attenuation measures which are listed can be combined with the additional overexpression measures (overexpression of the dapA gene, of the zwf gene, etc.) which are listed.

In this connection, the term "attenuation" describes the reduction or elimination of the intracellular activity of one or more enzymes (proteins) which are encoded by the corresponding DNA in a microorganism which is achieved, for example, by using a weak promoter or using a gene or allele which encodes a corresponding enzyme having low activity, or inactivating the corresponding gene or enzyme (protein), and, where appropriate, combining these measures.

As a result of using the measures for achieving attenuation, the activity or concentration of the corresponding protein is generally lowered to from 0 to 75%, from 0 to 50%, from 0 to 25%, from 0 to 10%, or from 0 to 5%, of the activity or concentration of the wild-type protein or of the activity or concentration of the protein in the starting microorganism.

Mutations which come into consideration for generating an attenuation are transitions, tranversions, insertions and deletions of at least one (1) base pair or nucleotide. Depending on the effect which the amino acid substitution elicited by the mutation has on the enzyme activity, reference is made to missense mutations or nonsense mutations. A missense mutation leads to the replacement of a given amino acid in a protein with another amino acid, with the amino acid replacement constituting, in particular, a nonconservative amino acid substitution. This substitution impairs the efficiency or activity of the protein and reduces it down to a value of from 0 to 75%, from 0 to 50%, from 0 to 25%, from 0 to 10%, or from 0 to 5%. A nonsense mutation leads to a stop codon being located in the coding region of the gene and consequently to translation being terminated prematurely. Insertions or deletions of at least one base pair in a gene lead to frame shift mutations which result in incorrect amino acids being incorporated or in the translation being terminated prematurely. If a stop codon is formed in the coding region as a consequence of mutation, this then also leads to translation being terminated prematurely. Deletions of at least one (1) or more codons typically also lead to complete loss of the enzyme activity.

Directions for generating such mutations belong to the prior art and are contained in known textbooks of genetics and molecular biology such as the textbook by Knippers ("Molekulare Genetik [Molecular Genetics]", 6$^{th}$ edition, Georg Thieme Verlag, Stuttgart, Germany, 1995), that by Winnacker ("Gene und Klone [Genes and Clones]", VCH Verlagsgesellschaft, Weinheim, Germany, 1990) or that by Hagemann ("Allgemeine Genetik [General Genetics]", Gustav Fischer Verlag, Stuttgart, 1986). Further measures are described in the prior art.

The isolated coryneform bacteria which are obtained by the measures of the invention exhibit a secretion or production of the desired amino acid, in a fermentation process, which is increased as compared with that of the starting strain or parental strain which was initially employed.

"Isolated bacteria" are to be understood as being the mutants and recombinant bacteria, in particular coryneform bacteria, according to the invention which are isolated or generated and which comprise an mqo allele which encodes a malate quinone oxidoreductase which contains the described amino acid substitution at position 111 in the amino acid sequence and, where appropriate, a replacement of the amino acid L-alanine with another proteinogenic amino acid, preferably L-serine, at position 201.

The performance of the isolated bacteria, or of the fermentation process when using these bacteria, in regard to one or more of the parameters selected from the group comprising the product concentration (product per volume), the product yield (product formed per carbon source consumed) and the product formation (product formed per volume and time), or else of other process parameters and combinations, is improved by at least 0.5%, at least 1%, at least 1.5%, or at least 2%, based on the starting strain or parental strain or the fermentation process when using these strains.

The isolated coryneform bacteria according to the invention can be cultured continuously, as described, for example, in PCT/EP2004/008882, or discontinuously, in a batch process or a fed-batch process or a repeated fed-batch process, for the purpose of producing L-amino acids. A general summary of known culturing methods can be found in the textbook by Chmiel (Bioprozesstechnik 1. Einführung in die Bioverfahrenstechnik [Bioprocess Technology 1. Introduction to Bioprocess Technology] (Gustav Fischer Verlag, Stuttgart, 1991)) or in the textbook by Storhas (Bioreaktoren und periphere Einrichtungen [Bioreactors and Peripheral Equipment] (Vieweg Verlag, Brunswick/Wiesbaden, 1994)).

The culture medium or fermentation medium to be used must suitably satisfy the requirements of the given strains. Descriptions of media for culturing different microorganisms are given in the manual "Manual of Methods for General Bacteriology" published by the American Society for Bacteriology (Washington D.C., USA, 1981). The terms culture medium and fermentation medium or medium are mutually interchangeable.

The carbon source employed can be sugars and carbohydrates, such as glucose, sucrose, lactose, fructose, maltose, molasses, sucrose-containing solutions derived from sugar beet or sugar cane production, starch, starch hydrolysate and cellulose, oils and fats, such as soybean oil, sunflower oil, peanut oil and coconut oil, fatty acids, such as palmitic acid, stearic acid and linoleic acid, alcohols, such as glycerol, methanol and ethanol, and organic acids, such as acetic acid. These substances can be used individually or as mixtures.

The nitrogen source employed can be organic nitrogen-containing compounds, such as peptones, yeast extract, meat extract, malt extract, cornsteep liquor, soybean flour and urea, or inorganic compounds, such as ammonium sulfate, ammonium chloride, ammonium phosphate, ammonium carbonate and ammonium nitrate. The nitrogen sources can be used individually or as mixtures.

The phosphorus source employed can be phosphoric acid, potassium dihydrogen phosphate or dipotassium hydrogen phosphate or the corresponding sodium-containing salts.

The culture medium must furthermore contain salts, for example in the form of chlorides or sulfates of metals such as sodium, potassium, magnesium, calcium and iron, for example magnesium sulfate or iron sulfate, which are necessary for growth. Finally, essential growth substances, such as amino acids, for example homoserine, and vitamins, for example thiamine, biotin or pantothenic acid, can be used in addition to the abovementioned substances. In addition to this, suitable precursors of the respective amino acid can be added to the culture medium.

The abovementioned added substances can be added to the culture in the form of a once-only mixture or fed in in a suitable manner during the culture.

Basic compounds such as sodium hydroxide, potassium hydroxide, ammonia or ammonia water, or acidic compounds such as phosphoric acid or sulfuric acid, are employed in a suitable manner for controlling the pH of the culture. In general, the pH is adjusted to a value of from 6.0 to 9.0, preferably of from 6.5 to 8. It is possible to use antifoamants, such as fatty acid polyglycol esters, for controlling foam formation. Suitable substances which act selectively, such as antibiotics, can be added to the medium in order to maintain the stability of plasmids. In order to maintain aerobic conditions, oxygen or oxygen-containing gas mixtures, such as air, are passed into the culture. It is also possible to use liquids which are enriched with hydrogen peroxide. Where appropriate, the fermentation is conducted under positive pressure, for example under a pressure of 0.03 to 0.2 MPa. The temperature of the culture is normally from 20° C. to 45° C., and preferably from 25° C. to 40° C. In the case of batch processes, the culture is continued until a maximum of the desired amino acid has been formed. This objective is normally achieved within from 10 hours to 160 hours. Longer culturing times are possible in the case of continuous processes.

Suitable fermentation media are described, inter alia, in U.S. Pat. Nos. 6,221,635, US 5,840,551, US 5,770,409, US 5,605,818, US 5,275,940 and US 4,224,409.

Methods for determining L-amino acids are disclosed in the prior art. The analysis can, for example, take place by means of anion exchange chromatography, followed by ninhydrin derivatization, as described in Spackman et al. (Analytical Chemistry, 30 (1958), 1190), or it can take place by reversed phase HPLC, as described in Lindroth et al. (Analytical Chemistry (1979) 51: 1167–1174).

The invention accordingly relates to a process for preparing an L-amino acid, in which process
a) an isolated coryneform bacterium is fermented in a suitable medium, with the bacterium comprising a gene which encodes a polypeptide which possesses malate quinone oxidoreductase enzyme activity, with the L-serine at position 111, or the corresponding position, in the amino acid sequences of the polypeptide being replaced with another proteinogenic amino acid, and with, where appropriate, the L-alanine at position 201 or the corresponding position being replaced with another proteinogenic amino acid, preferably L-serine, and
b) the L-amino acid being enriched in the fermentation broth or in the cells of the isolated coryneform bacterium.

The fermentation broth which has been prepared in this way is then subjected to further processing into a solid or liquid product.

A fermentation broth is understood as being a fermentation medium in which a microorganism is cultured for a certain time and at a certain temperature. The fermentation medium, or the mediums employed during the fermentation, contains/contain all the substances or components which ensure propagation of the microorganism and the formation of the desired amino acid.

At the conclusion of the fermentation, the resulting fermentation broth accordingly contains a) the biomass of the microorganism which has been formed as a consequence of the replication of the cells of the microorganism, b) the desired amino acid which has been formed during the fermentation, c) the organic by-products which have been formed during the fermentation, and d) the constituents of the fermentation medium/fermentation media employed, or the added substances, for example vitamins, such as biotin, amino acids, such as homoserine, or salts, such as magnesium sulfate, which were not consumed by the fermentation.

The organic by-products include substances which are produced by the microorganisms employed in the fermentation, where appropriate in addition to the given desired L-amino acid, and are secreted, where appropriate. These by-products include L-amino acids which amount to less than 30%, 20% or 10% of the desired amino acid. They also include organic acids which carry from 1 to 3 carboxyl groups, such as acetic acid, lactic acid, citric acid, malic acid or fumaric acid. Finally, they also include sugars, such as trehalose.

Typical fermentation broths which are suitable for industrial purposes have an amino acid content of from 40 g/kg to 180 g/kg or of from 50 g/kg to 150 g/kg. In general, the content of biomass (as dry biomass) is from 20 to 50 g/kg.

In the case of the amino acid L-lysine, essentially four different product forms have been disclosed in the prior art.

One group of L-lysine-containing products comprises concentrated, aqueous, alkaline solutions of purified L-lysine (EP-B-0534865). Another group, as described, for example, in U.S. Pat. Nos. 6,340,486 and US 6,465,025, comprises aqueous, acidic, biomass-containing concentrates of L-lysine-containing fermentation broths. The most well known group of solid products comprises pulverulent or crystalline forms of purified or pure L-lysine, which is typically present in the form of a salt such as L-lysine monohydrochloride. Another group of solid product forms is described, for example, in EP-B-0533039. The product form which is described in this document contains, in addition to L-lysine, the major portion of the added substances which were used during the fermentative preparation, and which were not consumed, and, where appropriate, from >0% to 100% of the biomass of the microorganism employed.

In correspondence with the different product forms, a very wide variety of methods are known for collecting, isolating or purifying the L-amino acid from the fermentation broth for the purpose of preparing the L-amino acid-containing product or the purified L-amino acid.

It is essentially ion exchange chromatography methods, where appropriate using active charcoal, and crystallization methods which are used for preparing solid, pure L-amino acids. In the case of lysine, this results in the corresponding base or a corresponding salt such as the monohydrochloride (Lys-HCl) or the lysine sulfate (Lys$_2$-H$_2$SO$_4$).

As far as lysine is concerned, EP-B-0534865 describes a method for preparing aqueous, basic L-lysine-containing solutions from fermentation broth. In this document, the biomass is separated off from the fermentation broth and discarded. A base such as sodium hydroxide, potassium hydroxide or ammonium hydroxide is used to adjust the pH to between 9 and 11. Following concentration and cooling, the mineral constituents (inorganic salts) are separated off from the broth by crystallization and either used as fertilizer or discarded.

In the case of processes for preparing lysine using the bacteria according to the invention, preference is given to those processes which result in products which contain constituents of the fermentation broth. These products are, in particular, used as animal feed additives.

Depending on the requirement, the biomass can be entirely or partially removed from the fermentation broth by means of separation methods such as centrifugation, filtration or decanting, or a combination of these methods, or all the biomass can be left in the fermentation broth. Where appropriate, the biomass, or the biomass-containing fermentation broth, is inactivated during a suitable process step, for example by means of thermal treatment (heating) or by means of adding acid.

The chemical constituents of the biomass are, inter alia, the cell envelope, for example the peptidoglycan and the arabinogalactan, the protein or polypeptide, for example the malate quinone oxidoreductase polypeptide, lipids and phospholipids and nucleic acids (DNA and RNA), for example polynucleotides containing the mutation according to the invention. As a consequence of the inactivation measures and/or the other procedural steps (for example acidification, spraydrying, granulation, etc.), nucleic acids are typically present as fragments having a length of, inter alia, $\geq$40–60 bp, >60–80 bp, >80–100 bp, >100–200 bp, >200–300 bp, >300–400 bp, >400–500 bp, >500–750 bp, >750–1000 bp, >1000–1250 bp, >1250–1500 bp, >1500–1750 bp, >1750–2000 bp, >2000–2500 bp, >2500–3000 bp, >3000–4000 bp, >4000–5000 bp.

In one approach, the biomass is completely or virtually completely removed, such that no (0%) or at most 30%, at most 20%, at most 10%, at most 5%, at most 1% or at most 0.1%, of the biomass remains in the prepared product. In another approach, the biomass is not removed, or only removed in trivial amounts, such that all (100%) or more than 70%, 80%, 90%, 95%, 99% or 99.9% of the biomass remains in the prepared product. In one process according to the invention, the biomass is accordingly removed in proportions of from $\geq$0% to $\leq$100%.

Finally, the fermentation broth which is obtained after the fermentation can be adjusted, before or after the biomass has been completely or partially removed, to an acid pH using an inorganic acid, such as hydrochloric acid, sulfuric acid or phosphoric acid, or an organic acid, such as propionic acid (GB 1,439,728 or EP 1 331 220). It is likewise possible to acidify the fermentation broth when it contains the entire biomass. Finally, the broth can also be stabilized by adding sodium bisulfite (NaHSO$_3$, GB 1,439,728) or another salt, for example an ammonium, alkali metal or alkaline earth metal salt of sulfurous acid.

Organic or inorganic solids which may be present in the fermentation broth are partially or entirely removed when the biomass is separated off. At least some (>0%), preferably at least 25%, particularly preferably at least 50%, and very particularly preferably at least 75%, of the organic by-products which are dissolved in the fermentation broth and the constituents of the fermentation medium (added substances), which are dissolved and not consumed remain in the product. Where appropriate, these by-products and constituents also remain completely (100%) or virtually completely, that is >95% or >98%, in the product. In this sense, the term "fermentation broth basis" means that a product comprises at least a part of the constituents of the fermentation broth.

Subsequently, water is extracted from the broth, or the broth is thickened or concentrated, using known methods, for example using a rotary evaporator, a thin-film evaporator or a falling-film evaporator, or by means of reverse osmosis or nanofiltration. This concentrated fermentation broth can then be worked up into flowable products, in particular into a finely divided powder or, preferably, a coarse-grained granulate, using methods of freeze drying, of spray drying or of spray granulation, or using other methods, for example in a circulating fluidized bed as described in PCT/EP2004/ 006655. Where appropriate, a desired product is isolated from the resulting granulate by means of screening or dust separation.

It is likewise possible to dry the fermentation broth directly, i.e. by spray drying or spray granulation without any prior concentration.

"Flowable" is understood as meaning powders which discharge unhindered from a series of glass discharge vessels having discharge apertures of different sizes, i.e. which discharge unhindered at least from a vessel having a 5 mm (millimeter) aperture (Klein: Seifen, Öle, Fette, Wachse [Soaps, Oils, Fats and Waxes] 94, 12 (1968)).

"Finely divided" means a powder the majority (>50%) of which has a particle size which is from 20 to 200 μm in diameter.

"Coarse-grained" means a product the majority (>50%) of which has a particle size of from 200 to 2000 μm in diameter.

The particle size can be determined using methods of laser diffraction spectrometry. The corresponding methods are described in the textbook "Teilchengrößenmessung in der Laborpraxis [Particle Size Measurement in Laboratory Practice]" by R. H. Müller and R. Schuhmann, Wissenschaftliche Verlagsgesellschaft Stuttgart (1996) or in the textbook "Introduction to Particle Technology" by M. Rhodes, Wiley & Sons (1998).

The flowable, finely divided powder can in turn be converted, by means of suitable compacting or granulating methods, into a coarse-grained, readily flowable, storable, and to a large extent dust-free, product.

The term "dust-free" means that the product only contains small proportions (<5%) of particle sizes of less than 100 μm in diameter.

Within the meaning of this invention, "storable" means a product which can be stored for at least one (1) year or longer, preferably at least 1.5 years or longer, particularly preferably two (2) years or longer, in a dry and cool environment without there being any significant loss (<5%) of the given amino acid.

The invention accordingly also relates to a process for preparing an L-amino acid-, preferably L-lysine- or L-tryptophan-, containing product, preferably an animal feed additive, from fermentation broth, which process is characterized by the steps of a) culturing and fermenting an L-amino acid-secreting coryneform bacterium, which comprises at least one mqo allele which encodes a polypeptide which possesses malate quinone oxidoreductase enzyme activity and which comprises an amino acid sequence in which any proteinogenic amino acid apart from L-serine is present at position 111 or the comparable position, with, where appropriate, any proteinogenic amino acid, preferably L-serine, being present at position 201 or the comparable position, in a fermentation medium, b) removing from 0 to 100% by weight of the biomass which is formed during the fermentation, and c) drying the fermentation broth which is obtained in accordance with a) and/or b) in order to obtain the product in the desired powder form or granulate form, with, where appropriate, an acid selected from the group sulfuric acid, phosphoric acid or hydrochloric acid being added prior to step b) or c).

Preference is given to water being removed (concentration) from the L-amino acid-containing fermentation broth after step a) or b).

It is advantageous to use customary organic or inorganic auxiliary substances, or carrier substances such as starch, gelatin, cellulose derivatives or similar substances, as are customarily used as binders, gelatinizers or thickeners in foodstuff or feedstuff processing, or other substances, such as silicic acids, silicates (EP0743016A) or stearates, in connection with the granulation or compacting.

It is furthermore advantageous to provide the surface of the resulting granulates with oils, as described in WO 04/054381. The oils which can be used are mineral oils, vegetable oils or mixtures of vegetable oils. Examples of these oils are soybean oil, olive oil and soybean oil/lecithin mixtures. In the same way, silicone oils, polyethylene glycols or hydroxyethyl celulose are also suitable. Treating the surfaces with said oils increases the abrasion resistance of the product and reduces the dust content. The content of oil in the product is from 0.02 to 2.0% by weight, preferably from 0.02 to 1.0% by weight, and very particularly preferably from 0.2 to 1.0% by weight, based on the total quantity of the feedstuff additives.

Preference is given to products having a content of ≧97% by weight of a particle size of from 100 to 1800 μm, or a content of ≧95% by weight of a particle size of from 300 to 1800 μm, in diameter. The content of dust, i.e. particles having a particle size of <100 μm, is preferably from >0 to 1% by weight, particularly preferably at most 0.5% by weight.

Alternatively, however, the product can also be absorbed onto an organic or inorganic carrier substance which is known and customary in feedstuff processing, for example silicic acids, silicates, grists, brans, meals, starches, sugars etc., and/or be mixed and stabilized with customary thickeners or binders. Application examples and methods in this regard are described in the literature (Die Mühle+Mischfuttertechnik [The Grinding Mill+Mixed Feed Technology] 132 (1995) 49, page 817).

Finally, the product can also be brought, by means of coating methods using film formers such as metal carbonates, silicic acids, silicates, alginates, stearates, starches, rubbers and cellulose ethers, as described in DE-C-4100920, into a state in which it is stable towards digestion by animal stomachs, in particular the ruminant stomach.

In order to set a desired amino acid concentration in the product, the appropriate amino acid can, depending on the requirement, be added during the process in the form of a concentrate or, where appropriate, of a largely pure substance or its salt in liquid or solid form. The latter can be added individually, or as mixtures, to the resulting fermentation broth, or to the concentrated fermentation broth, or else added during the drying process or granulation process.

In the case of lysine, the ratio of the ions is adjusted during the preparation of lysine-containing products such that the ion ratio in accordance with the following formula

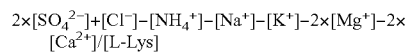

$$2\times[SO_4^{2-}]+[Cl^-]-[NH_4^+]-[Na^+]-[K^+]-2\times[Mg^+]-2\times[Ca^{2+}]/[L\text{-}Lys]$$

has a value of from 0.68 to 0.95, preferably of from 0.68 to 0.90, as described by Kushiki et al. in US 20030152633.

In the case of lysine, the solid fermentation broth-based product which has been prepared in this way has a lysine content (as lysine base) of from 10% by weight to 70% by weight or of from 20% by weight to 70% by weight, preferably of from 30% by weight to 70% by weight and very particularly preferably of from 40% by weight to 70% by weight, based on the dry mass of the product. It is also possible to achieve maximum contents of lysine base of 71% by weight, 72% by weight or 73% by weight.

In the case of an electrically neutral amino acid such as L-tryptophan, the solid fermentation broth-based product which has been prepared in this way has an amino acid content of at least 5% by weight, 10% by weight, 20% by weight or 30% by weight and maximally 50% by weight, 60% by weight, 70% by weight, 80% by weight, 90% by weight or up to 95% by weight.

The water content of the solid product is up to 5% by weight, preferably up to 4% by weight, and particularly preferably less than 3% by weight.

The invention therefore also relates to an L-lysine-containing, fermentation broth-based feed additive which exhibits the following features a) a lysine content (as base) of at least 10% by weight to at most 73% by weight, b) a water content of at most 5% by weight, and c) a biomass content corresponding to at least 0.1% of the biomass contained in the fermentation broth, with the biomass, which is inactivated where appropriate, being formed from coryneform bacteria according to the invention.

The invention furthermore also relates to an L-tryptophan-containing, fermentation broth-based feed additive which exhibits the following features a) a tryptophan content of at least 5% by weight to at most 95% by weight, b) a water content of at most 5% by weight, and c) a biomass content corresponding to at least 0.1% of the biomass contained in the fermentation broth, with the biomass, which is inactivated where appropriate, being formed from coryneform bacteria according to the invention.

A mutant of *Corynebacterium glutamicum* which is designated DM1797 and which comprises the amino acid substitution lysC T311I in its aspartate kinase was deposited on Oct. 28, 2004 in the Deutsche Sammlung für Mikroorganismen und Zellkulturen [German Collection of Microorganisms and Cell Cultures] (DSMZ, Brunswick, Germany) as DSM 16833.

The *Corynebacterium glutamicum* mutant DM1808 according to the invention, which comprises L-phenylalanine at position 111 in the amino acid sequence of the mqo polypeptide, was deposited on Nov. 24, 2004 in the Deutsche Sammlung für Mikroorganismen und Zellkulturen [German Collection of Microorganisms and Cell Cultures] (DSMZ, Brunswick, Germany) as DSM16937.

EXAMPLES

Example 1

Mutagenesis of the L-lysine-Producing Strain DM1797

The *Corynebacterium glutamicum* strain DM1797 was used as the starting strain for the mutagenesis using N-methyl-N'-nitro-N-nitrosoguanidine (MNNG). The strain DM1797 is an aminoethylcysteine-resistant mutant of *Corynebacterium glutamicum* ATCC13032 and is deposited in the Deutsche Sammlung für Mikroorganismen und Zellkulturen [German Collection of Microorganisms and Cell Cultures] (DSMZ, Brunswick, Germany) under the designation DSM16833.

The strain DM1797 was cultured in 10 ml of LB broth (Merck, Darmstadt, Germany), which were contained in a 100 ml Erlenmeyer flask, at 33° C. at 200 rpm for 24 hours on a rotary shaker of the Certomat BS-1 type (B. Braun Biotech International, Melsungen, Germany). The culture was then centrifuged and the sediment was resuspended in 10 ml of 0.9% NaCl solution; the resulting suspension was centrifuged once again and the sediment which was obtained was taken up in 10 ml of 0.9% NaCl solution. 5 ml of this cell suspension were treated with 400 µg of MNNG/ml for 15 minutes at 30° C. and 200 rpm on a shaker (see above). The mutagenesis mixture was then centrifuged and the sediment was taken up in 10 ml of 2% Na thiosulfate in 0.9% NaCl buffer (pH=6.0). The cell suspension was then diluted with 0.9% NaCl solution in ratios of 1:1000, 1:10 000 and 1:100 000, and aliquots were plated out on brain-heart agar (Merck, Darmstadt, Germany). Approximately 2500 mutants were isolated in this way.

Example 2

Test of the Performance of the Strain DM1797 Mutants

The mutants obtained in Example 1 were cultured in a nutrient medium suitable for producing lysine, and the lysine content in the culture supernatant was determined.

For this, the clones were first of all propagated at 33° C. for 24 hours on brain-heart agar plates (Merck, Darmstadt, Germany). These agar plate cultures were then used for in each case inoculating one preliminary culture (10 ml of medium in a 100 ml Erlenmeyer flask). The medium used for the preliminary culture was MM medium. The preliminary culture was incubated at 33° C. and 240 rpm for 24 hours on a shaker. This preliminary culture was used to inoculate a main culture such that the initial OD (660 nm) of the main culture was 0.1 OD. The MM medium was also used for the main culture.

| MM medium | |
|---|---|
| CSL | 5 g/l |
| MOPS | 20 g/l |
| Glucose (autoclaved separately) | 50 g/l |
| Salts: | |
| $(NH_4)_2SO_4)$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterilized by filtration) | 0.3 mg/l |
| Thiamin * HCl (sterilized by filtration) | 0.2 mg/l |
| $CaCO_3$ | 25 g/l |

CSL (corn steep liquor), MOPS (morpholinopropanesulfonic acid) and the salt solution were adjusted to pH 7 with ammonia water and autoclaved. The sterile substrate and vitamin solutions, as well as the $CaCO_3$, which was autoclaved in the dry state, were then added.

The culture was effected in 10 ml volumes which were contained in 100 ml Erlenmeyer flasks possessing baffles. The temperature was 33° C., the rotational speed was 250 rpm and the atmospheric humidity was 80%.

After 48 hours, the optical density (OD) was determined at a measurement wavelength of 660 nm using a Biomek 1000 (Beckmann Instruments GmbH, Munich). The quantity of lysine formed was determined, by means of ion exchange chromatography and post-column derivatization with ninhydrin detection, using an Eppendorf-BioTronik amino acid analyzer (Hamburg, Germany). A mutant which was distinguished by an elevated formation of lysine was designated DM1808.

TABLE 1

| Strain | OD (660) | Lysine-HCl (g/l) |
|---|---|---|
| DM1797 | 12.1 | 4.9 |
| DM1808 | 12.0 | 5.3 |

Example 3

Sequencing the mqo Gene of the Mutant DM1808

The method of Eikmanns et al. (Microbiology 140: 1817–1828 (1994)) was used to isolate chromosomal DNA from the DM1808 clone. The polymerase chain reaction was used to amplify a DNA segment carrying the mqo gene. The following oligonucleotides were used as primers for this purpose:

```
mqo-A1 (SEQ ID NO: 13):
5' ggtgaaacttccgcgatact 3' mqo-E1 (SEQ ID NO: 14):
5' gtgtcgccta aatcacactg 3'
```

The depicted primers were synthesized by MWG Biotech (Ebersberg, Germany). They enable a DNA segment which is approx. 2 kb in length and which carries the mqo gene to be amplified. The primer mqo-A1 binds to the region corresponding to position 22 to 41 in the strand which is complementary to SEQ ID NO: 3. The primer mqo-E1 binds to the region corresponding to position 2002 to 1983 in the strand depicted in SEQ ID NO: 3.

The PCR reaction was carried out using Phusion High Fidelity DNA polymerase (New England Biolabs, Frankfurt, Germany). The reaction mixture was prepared in accordance with the manufacturer's instructions and contained, at a total volume of 50 µl, 10 µl of the 5× Phusion HF buffer which was also supplied, deoxynucleoside triphosphates at a concentration of in each case 200 µM, primers at a concentration of 0.5 µM, approximately 50 ng of template DNA and 2 units of Phusion polymerase. The volume was adjusted to 50 µl by adding $H_2O$.

The PCR mixture was first of all subjected to an introductory denaturation at 98° C. for 30 seconds. There then followed, with this being repeated 35×, a denaturation step at 98° C. for 20 seconds, a step for binding the primers to the introduced DNA at 60° C. for 20 seconds, and the extension step for extending the primers at 72° C. for 60 seconds. After the concluding extension step, for 5 minutes at 72° C., the PCR mixture was subjected to an agarose gel electrophoresis (0.8% agarose). A DNA fragment which is approx. 2 kb in length was identified, isolated from the gel and purified using the QIAquick gel extraction kit from Qiagen (Hilden, Germany).

The nucleotide sequence of the amplified DNA fragment or PCR product was determined by Agowa (Berlin, Germany). The resulting sequence of the coding region of the mqo allele is depicted in SEQ ID NO: 5. The amino acid sequence of the protein which is obtained when using the Patentin program is depicted in SEQ ID NO: 6.

The nucleotide sequence of the coding region of the mqo allele in mutant DM1808 contains the nucleobase thymin at position 332 (see SEQ ID NO: 5). The wild-type gene (see SEQ ID NO: 1) contains the nucleobase cytosine at this position. This cytosine-thymine transition leads to the replacement of the amino acid serine by phenylalanine at position 111 of the resulting amino acid sequence. This mutation is designated as mqoS111F in that which follows.

Example 4

Construction of the Replacement Vector pK18omobsacB_mqoS111F

The polymerase chain reaction was used to amplify a part of the coding region, that is an internal fragment or internal region, of the mqo allele which carries the mqoS111F mutation. The chromosomal DNA which was isolated in Example 3 was used as the template. The following oligonucleotides were selected as primers for the PCR:

```
mqo-int1-bam (SEQ ID NO: 27):
5' ctag-ggatcc-ccgaagaacgcaccgaggat 3' mqo-int2-bam (SEQ ID NO: 28):
5' ctag-ggatcc-ggcggatggacttgaacagg 3'
```

They were synthesized by MWG Biotech (Ebersberg, Germany) and make it possible to amplify a DNA segment of the coding region which is approx. 1.05 kb in length. Nucleotides 11 to 30 of the mqo-int1-bam primer bind to the region corresponding to position 362 to 381 in the strand which is complementary to SEQ ID NO: 3. Positions 362 and 381 of SEQ ID NO: 3 correspond to positions 13 and 32 in SEQ ID NO: 1. Nucleotides 11 to 30 of the mqo-int2-bam primer bind to the region corresponding to position 1385 to 1366 in the strand depicted in SEQ ID NO: 3. Positions 1385 and 1366 in SEQ ID NO: 3 correspond to positions 1036 and 1017 in SEQ ID NO: 1. In addition, the primers contain the sequences for cleavage sites for restriction endonuclease BamHI, which sites are underlined in the above nucleotide sequence.

The PCR reaction was carried out using Phusion High-Fidelity DNA polymerase (New England Biolabs, Frankfurt, Germany). The reaction mixture had the composition as described above. The PCR was carried out as described above but with one exception: the 72° C. extension step in the cycle which was repeated 35 times was in each case only carried out for 30 seconds.

The amplificate, which was approx. 1.05 kb in length, was treated with the restriction endonuclease BamHI and identified by electrophoresis in an 0.8% agarose gel. It was then isolated from the gel and purified using the QIAquick gel extraction kit from Qiagen.

The DNA fragment which was purified in this way contains the described mqoS111F mutation and possesses BamHI-compatible ends (mqoS111F fragment or 'mqo' in FIG. 1). It was then incorporated into the mobilizable vector pK18mobsacB, described by Schäfer et al. (Gene, 145, 69–73 (1994)) in order to make it possible to achieve an allele or mutation replacement. For this, pK18mobsacB was digested with the restriction enzyme BamHI and the ends were dephosphorylated with alkaline phosphatase (Boehringer Mannheim, Germany). The vector which had been prepared in this way was mixed with the mqoS111F fragment and the mixture was treated with the Ready-To-Go T4 DNA ligase kit (Amersham-Pharmacia, Freiburg, Germany).

The E. coli strain S17-1 (Simon et al., Bio/Technologie 1: 784–791, 1993) was then transformed with the ligation mixture (Hanahan, In. DNA cloning. A practical approach. Vol. 1. ILR-Press, Cold Spring Harbor, N.Y., 1989). The selection for plasmid-harboring cells was effected by plating out the transformation mixture on LB agar (Sambrook et al., Molecular Cloning: a laboratory manual. $2^{nd}$ Ed. Cold Spring Harbor, N.Y., 1989), which was supplemented with 25 mg/l of kanamycin/l.

Plasmid DNA was isolated from a transformant using the Qiagen QIAprep Spin Miniprep kit and checked by restriction-cleaving once with the enzyme BamHI and once with the enzyme EcoRI and then performing agarose gel electrophoresis. The plasmid was named pK18mobsacB_mqoS111F and is depicted in FIG. 1.

Example 5

Incorporation of the Mutation mqoS111F into Strain DM1797

The vector pK18mobsacB_mqoS111F, as described in Example 4, was transferred by conjugation into the C. glutamicum strain DM1797 using the protocol of Schäfer et al. (Journal of Microbiology 172: 1663–1666 (1990)). The vector cannot replicate independently in DM1797 and is only preserved in the cell when it has been integrated into the chromosome as a consequence of a recombination event. Transconjugants, i.e. clones containing integrated pK18mobsacB_mqoS111F, were selected by plating out the conjugation mixture on LB agar which had been supplemented with 25 mg of kanamycin/l and 50 mg of nalidixic acid/l. Kanamycin-resistant transconjugants were then streaked out on LB agar plates supplemented with kanamycin (25 mg/l) and the plates were incubated at 33° C. for 24 hours. In order to select mutants in which the plasmid had been excised as a consequence of a second recombination event, the clones were cultured nonselectively in LB liquid medium for 30 hours and then streaked out on LB agar which had been supplemented with 10% sucrose; the plates were then incubated at 33° C. for 24 hours.

In addition to the kanamycin resistance gene, the plasmid pK18mobsacB_mqoS111F, just like the starting plasmid pK18mobsacB, contains a copy of the sacB gene, which encodes *Bacillus subtilis* levan sucrase. The sucrose-inducible expression of the sacB gene leads to the formation of levan sucrase, which catalyzes the synthesis of the product levan, which is toxic for *C. glutamicum*. The only clones which grow on sucrose-supplemented LB agar are therefore those in which the integrated pK18mobsacB_mqoS111F has excised as a consequence of a second recombination event. When the excision occurs, either replacement of the allele, or incorporation of the mutation, takes place or the original copy remains in the chromosome of the host, depending on the location of the second recombination event in relation to the mutation site.

A clone was then sought in which the desired replacement, i.e. the incorporation of the mutation mqoS111F, had taken place. For this, the sequence of the mqo gene was determined in 10 clones which exhibited the "growth in the presence of sucrose" and "no growth in the presence of kanamycin" phenotype. This resulted in the identification of a clone which carries the mutation mqoS111F. This strain was designated *C. glutamicum* DM1797_mqoS111F.

Example 6

Comparison of the Performance of the Strain DM1797_mqoS111F with that of the Starting Strain DM1797

The performance test was carried out as described in Example 2. The strain DM1797_mqoS111F exhibited, like DM1808, a lysine secretion which was markedly higher than that of DM1797 (see Table 1).

The abbreviations and designations employed have the following meanings. The base pair numbers which are given are approximate values which are obtained within the limits of the reproducibility of measurements.

Kan: Kanamycin resistance gene
BamHI: Cleavage site for the restriction enzyme EcoRI
EcoRI: Cleavage site for the restriction enzyme EcoRI
'mqo': Cloned DNA fragment containing an internal region of the mqoS111F allele
sacB: sacB gene
RP4-mob: mob region containing the transfer origin of replication (oriT)
oriV: Origin of replication V All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. An isolated coryneform bacterium mutant which comprises a gene encoding a polypeptide with the amino acid sequence of SEQ ID NO:2, and wherein
   a) any proteinogenic amino acid except L-serine is present at position 111; and
   b) said polypeptide has malate quinone oxidoreductase enzymatic activity.

2. The coryneform bacterium mutant of claim 1, wherein said coryneform bacterium mutant is of a species selected from the group consisting of: *Corynebacterium efficiens; Corynebacterium glutamicum; Corynebacterium thermoaminogenes;* and *Corynebacterium aminogenes.*

3. The coryneform bacterium mutant of claim 2, wherein said coryneform bacterium mutant is of the species *Corynebacterium glutamicum.*

4. The coryneform bacterium mutant of claim 1, wherein the encoded polypeptide contains either L-phenylalanine or L-alanine at position 111.

5. An isolated polynucleotide which encodes a polypeptide comprising an amino acid sequence having at least 96% sequence identity with the amino acid sequence of SEQ ID NO: 6 or 8 and wherein
   a) any proteinogenic amino acid except L-serine is present at position 111; and
   b) said polypeptide has malate quinone oxidoreductase enzymatic activity.

6. The isolated polynucleotide of claim 5, wherein said polynucleotide encodes a protein comprising the amino acid sequence of SEQ ID NO:2.

7. The isolated polynucleotide of claim 5 wherein said proteinogenic amino acid at position 111 is L-phenylalanine or L-alanine.

8. The isolated polynucleotide of claim 5, wherein the encoded polypeptide comprises an amino acid sequence having a length of 500 amino acids.

9. The isolated polynucleotide of claim 5, wherein said isolated polynucleotide hybridizes under stringent conditions comprising washing at 0.1×SSC, 0.1% SDS at 68° C. with a nucleotide sequence which is complementary to: SEQ ID NO:5; SEQ ID NO:7; or SEQ ID NO:9.

10. A vector comprising the isolated polynucleotide of claim 5.

11. A recombinant microorganism which has been transformed with the vector of claim 10.

12. The recombinant microorganism of claim 11, wherein said recombinant microorganism is a coryneform bacterium or a bacterium of the genus *Escherichia.*

* * * * *

SEQUENCE LISTING

<160> NUMBER OF SEQ ID NOS: 28

<210> SEQ ID NO 1
<211> LENGTH: 1503
<212> TYPE: DNA
<213> ORGANISM: Corynebacterium glutamicum
<220> FEATURE:
<221> NAME/KEY: CDS
<222> LOCATION: (1)..(1500)
<223> OTHER INFORMATION: mqo wild-type gene

<400> SEQUENCE: 1

```
atg tca gat tcc ccg aag aac gca ccg agg att acc gat gag gca gat      48
Met Ser Asp Ser Pro Lys Asn Ala Pro Arg Ile Thr Asp Glu Ala Asp
1               5                  10                  15 gta gtt ctc att ggt gcc ggt atc atg agc tcc acg ctg ggt gca atg      96
Val Val Leu Ile Gly Ala Gly Ile Met Ser Ser Thr Leu Gly Ala Met
                20                  25                  30 ctg cgt cag ctg gag cca agc tgg act cag atc gtc ttc gag cgt ttg     144
Leu Arg Gln Leu Glu Pro Ser Trp Thr Gln Ile Val Phe Glu Arg Leu
            35                  40                  45 gat gga ccg gca caa gag tcg tcc tcc ccg tgg aac aat gca gga acc     192
Asp Gly Pro Ala Gln Glu Ser Ser Ser Pro Trp Asn Asn Ala Gly Thr
        50                  55                  60 ggc cac tct gct cta tgc gag ctg aac tac acc cca gag gtt aag ggc     240
Gly His Ser Ala Leu Cys Glu Leu Asn Tyr Thr Pro Glu Val Lys Gly
65                  70                  75                  80 aag gtt gaa att gcc aag gct gta gga atc aac gag aag ttc cag gtt     288
Lys Val Glu Ile Ala Lys Ala Val Gly Ile Asn Glu Lys Phe Gln Val
                85                  90                  95 tcc cgt cag ttc tgg tct cac ctc gtt gaa gag gga gtg ctg tct gat     336
Ser Arg Gln Phe Trp Ser His Leu Val Glu Glu Gly Val Leu Ser Asp
                100                 105                 110
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| cct | aag | gaa | ttc | atc | aac | cct | gtt | cct | cac | gta | tct | ttc | ggc | cag | ggc | 384 |
| Pro | Lys | Glu | Phe | Ile | Asn | Pro | Val | Pro | His | Val | Ser | Phe | Gly | Gln | Gly |     |
|     |     | 115 |     |     |     |     | 120 |     |     |     |     | 125 |     |     |     |     |
| gca | gat | cag | gtt | gca | tac | atc | aag | gct | cgc | tac | gaa | gct | ttg | aag | gat | 432 |
| Ala | Asp | Gln | Val | Ala | Tyr | Ile | Lys | Ala | Arg | Tyr | Glu | Ala | Leu | Lys | Asp |     |
|     | 130 |     |     |     |     | 135 |     |     |     |     | 140 |     |     |     |     |     |
| cac | cca | ctc | ttc | cag | ggc | atg | acc | tac | gct | gac | gat | gaa | gct | acc | ttc | 480 |
| His | Pro | Leu | Phe | Gln | Gly | Met | Thr | Tyr | Ala | Asp | Asp | Glu | Ala | Thr | Phe |     |
| 145 |     |     |     |     | 150 |     |     |     |     | 155 |     |     |     |     | 160 |     |
| acc | gag | aag | ctg | cct | ttg | atg | gca | aag | ggc | cgt | gac | ttc | tct | gat | cca | 528 |
| Thr | Glu | Lys | Leu | Pro | Leu | Met | Ala | Lys | Gly | Arg | Asp | Phe | Ser | Asp | Pro |     |
|     |     |     |     | 165 |     |     |     |     | 170 |     |     |     |     | 175 |     |     |
| gta | gca | atc | tct | tgg | atc | gat | gaa | ggc | acc | gac | atc | aac | tac | ggt | gct | 576 |
| Val | Ala | Ile | Ser | Trp | Ile | Asp | Glu | Gly | Thr | Asp | Ile | Asn | Tyr | Gly | Ala |     |
|     |     |     | 180 |     |     |     |     | 185 |     |     |     |     | 190 |     |     |     |
| cag | acc | aag | cag | tac | ctg | gat | gca | gct | gaa | gtt | gaa | ggc | act | gaa | atc | 624 |
| Gln | Thr | Lys | Gln | Tyr | Leu | Asp | Ala | Ala | Glu | Val | Glu | Gly | Thr | Glu | Ile |     |
|     |     | 195 |     |     |     |     | 200 |     |     |     |     | 205 |     |     |     |     |
| cgc | tat | ggc | cac | gaa | gtc | aag | agc | atc | aag | gct | gat | ggc | gca | aag | tgg | 672 |
| Arg | Tyr | Gly | His | Glu | Val | Lys | Ser | Ile | Lys | Ala | Asp | Gly | Ala | Lys | Trp |     |
|     | 210 |     |     |     |     | 215 |     |     |     |     | 220 |     |     |     |     |     |
| atc | gtg | acc | gtc | aag | aac | gta | cac | act | ggc | gac | acc | aag | acc | atc | aag | 720 |
| Ile | Val | Thr | Val | Lys | Asn | Val | His | Thr | Gly | Asp | Thr | Lys | Thr | Ile | Lys |     |
| 225 |     |     |     |     | 230 |     |     |     |     | 235 |     |     |     |     | 240 |     |
| gca | aac | ttc | gtg | ttc | gtc | ggc | gca | ggc | gga | tac | gca | ctg | gat | ctg | ctt | 768 |
| Ala | Asn | Phe | Val | Phe | Val | Gly | Ala | Gly | Gly | Tyr | Ala | Leu | Asp | Leu | Leu |     |
|     |     |     |     | 245 |     |     |     |     | 250 |     |     |     |     | 255 |     |     |
| cgc | agc | gca | ggc | atc | cca | cag | gtc | aag | ggc | ttc | gct | gga | ttc | cca | gta | 816 |
| Arg | Ser | Ala | Gly | Ile | Pro | Gln | Val | Lys | Gly | Phe | Ala | Gly | Phe | Pro | Val |     |
|     |     | 260 |     |     |     |     | 265 |     |     |     |     | 270 |     |     |     |     |
| tcc | ggc | ctg | tgg | ctt | cgt | tgc | acc | aac | gag | gaa | ctg | atc | gag | cag | cac | 864 |
| Ser | Gly | Leu | Trp | Leu | Arg | Cys | Thr | Asn | Glu | Glu | Leu | Ile | Glu | Gln | His |     |
|     | 275 |     |     |     |     | 280 |     |     |     |     | 285 |     |     |     |     |     |
| gca | gcc | aag | gta | tat | ggc | aag | gca | tct | gtt | ggc | gct | cct | cca | atg | tct | 912 |
| Ala | Ala | Lys | Val | Tyr | Gly | Lys | Ala | Ser | Val | Gly | Ala | Pro | Pro | Met | Ser |     |
| 290 |     |     |     |     | 295 |     |     |     |     | 300 |     |     |     |     |     |     |
| gtt | cct | cac | ctt | gac | acc | cgc | gtt | atc | gag | ggt | gaa | aag | ggt | ctg | ctc | 960 |
| Val | Pro | His | Leu | Asp | Thr | Arg | Val | Ile | Glu | Gly | Glu | Lys | Gly | Leu | Leu |     |
| 305 |     |     |     |     | 310 |     |     |     |     | 315 |     |     |     |     | 320 |     |
| ttt | gga | cct | tac | ggt | ggc | tgg | acc | cct | aag | ttc | ttg | aag | gaa | ggc | tcc | 1008 |
| Phe | Gly | Pro | Tyr | Gly | Gly | Trp | Thr | Pro | Lys | Phe | Leu | Lys | Glu | Gly | Ser |     |
|     |     |     |     | 325 |     |     |     |     | 330 |     |     |     |     | 335 |     |     |
| tac | ctg | gac | ctg | ttc | aag | tcc | atc | cgc | cca | gac | aac | att | cct | tcc | tac | 1056 |
| Tyr | Leu | Asp | Leu | Phe | Lys | Ser | Ile | Arg | Pro | Asp | Asn | Ile | Pro | Ser | Tyr |     |
|     |     |     | 340 |     |     |     |     | 345 |     |     |     |     | 350 |     |     |     |
| ctt | ggc | gtt | gct | gct | cag | gaa | ttt | gat | ctg | acc | aag | tac | ctt | gtc | act | 1104 |
| Leu | Gly | Val | Ala | Ala | Gln | Glu | Phe | Asp | Leu | Thr | Lys | Tyr | Leu | Val | Thr |     |
|     |     | 355 |     |     |     |     | 360 |     |     |     |     | 365 |     |     |     |     |
| gaa | gtt | ctc | aag | gac | cag | gac | aag | cgt | atg | gat | gct | ctt | cgc | gag | tac | 1152 |
| Glu | Val | Leu | Lys | Asp | Gln | Asp | Lys | Arg | Met | Asp | Ala | Leu | Arg | Glu | Tyr |     |
|     | 370 |     |     |     |     | 375 |     |     |     |     | 380 |     |     |     |     |     |
| atg | cca | gag | gca | caa | aac | ggc | gat | tgg | gag | acc | atc | gtt | gcc | gga | cag | 1200 |
| Met | Pro | Glu | Ala | Gln | Asn | Gly | Asp | Trp | Glu | Thr | Ile | Val | Ala | Gly | Gln |     |
| 385 |     |     |     |     | 390 |     |     |     |     | 395 |     |     |     |     | 400 |     |
| cgt | gtt | cag | gtt | att | aag | cct | gca | gga | ttc | cct | aag | ttc | ggt | tcc | ctg | 1248 |
| Arg | Val | Gln | Val | Ile | Lys | Pro | Ala | Gly | Phe | Pro | Lys | Phe | Gly | Ser | Leu |     |
|     |     |     |     | 405 |     |     |     |     | 410 |     |     |     |     | 415 |     |     |
| gaa | ttc | ggc | acc | acc | ttg | atc | aac | aac | tcc | gaa | ggc | acc | atc | gcc | gga | 1296 |
| Glu | Phe | Gly | Thr | Thr | Leu | Ile | Asn | Asn | Ser | Glu | Gly | Thr | Ile | Ala | Gly |     |
|     |     |     | 420 |     |     |     |     | 425 |     |     |     |     | 430 |     |     |     |

-continued

```
ttg ctc ggt gct tcc cct gga gca tcc atc gca cct tcc gca atg atc    1344
Leu Leu Gly Ala Ser Pro Gly Ala Ser Ile Ala Pro Ser Ala Met Ile
        435                 440                 445 gag ctg ctt gag cgt tgc ttc ggt gac cgc atg atc gag tgg ggc gac    1392
Glu Leu Leu Glu Arg Cys Phe Gly Asp Arg Met Ile Glu Trp Gly Asp
    450                 455                 460 aag ctg aag gac atg atc cct tcc tac ggc aag aag ctt gct tcc gag    1440
Lys Leu Lys Asp Met Ile Pro Ser Tyr Gly Lys Lys Leu Ala Ser Glu
465                 470                 475                 480 cca gca ctg ttt gag cag cag tgg gca cgc acc cag aag acc ctg aag    1488
Pro Ala Leu Phe Glu Gln Gln Trp Ala Arg Thr Gln Lys Thr Leu Lys
                485                 490                 495 ctt gag gaa gcc taa                                                1503
Leu Glu Glu Ala
    500

<210> SEQ ID NO 2
<211> LENGTH: 500
<212> TYPE: PRT
<213> ORGANISM: Corynebacterium glutamicum

<400> SEQUENCE: 2

Met Ser Asp Ser Pro Lys Asn Ala Pro Arg Ile Thr Asp Glu Ala Asp
1               5                   10                  15

Val Val Leu Ile Gly Ala Gly Ile Met Ser Ser Thr Leu Gly Ala Met
                20                  25                  30

Leu Arg Gln Leu Glu Pro Ser Trp Thr Gln Ile Val Phe Glu Arg Leu
            35                  40                  45

Asp Gly Pro Ala Gln Glu Ser Ser Pro Trp Asn Asn Ala Gly Thr
        50                  55                  60

Gly His Ser Ala Leu Cys Glu Leu Asn Tyr Thr Pro Glu Val Lys Gly
65              70                  75                  80

Lys Val Glu Ile Ala Lys Ala Val Gly Ile Asn Glu Lys Phe Gln Val
                85                  90                  95

Ser Arg Gln Phe Trp Ser His Leu Val Glu Glu Gly Val Leu Ser Asp
            100                 105                 110

Pro Lys Glu Phe Ile Asn Pro Val Pro His Val Ser Phe Gly Gln Gly
        115                 120                 125

Ala Asp Gln Val Ala Tyr Ile Lys Ala Arg Tyr Glu Ala Leu Lys Asp
    130                 135                 140

His Pro Leu Phe Gln Gly Met Thr Tyr Ala Asp Asp Glu Ala Thr Phe
145                 150                 155                 160

Thr Glu Lys Leu Pro Leu Met Ala Lys Gly Arg Asp Phe Ser Asp Pro
                165                 170                 175

Val Ala Ile Ser Trp Ile Asp Glu Gly Thr Asp Ile Asn Tyr Gly Ala
            180                 185                 190

Gln Thr Lys Gln Tyr Leu Asp Ala Ala Glu Val Glu Gly Thr Glu Ile
        195                 200                 205

Arg Tyr Gly His Glu Val Lys Ser Ile Lys Ala Asp Gly Ala Lys Trp
    210                 215                 220

Ile Val Thr Val Lys Asn Val His Thr Gly Asp Thr Lys Thr Ile Lys
225                 230                 235                 240

Ala Asn Phe Val Phe Val Gly Ala Gly Tyr Ala Leu Asp Leu Leu
                245                 250                 255

Arg Ser Ala Gly Ile Pro Gln Val Lys Gly Phe Ala Gly Phe Pro Val
            260                 265                 270
```

-continued

Ser Gly Leu Trp Leu Arg Cys Thr Asn Glu Glu Leu Ile Glu Gln His
        275                 280                 285

Ala Ala Lys Val Tyr Gly Lys Ala Ser Val Gly Ala Pro Pro Met Ser
    290                 295                 300

Val Pro His Leu Asp Thr Arg Val Ile Glu Gly Lys Gly Leu Leu
305                 310                 315                 320

Phe Gly Pro Tyr Gly Gly Trp Thr Pro Lys Phe Leu Lys Glu Gly Ser
                325                 330                 335

Tyr Leu Asp Leu Phe Lys Ser Ile Arg Pro Asp Asn Ile Pro Ser Tyr
            340                 345                 350

Leu Gly Val Ala Ala Gln Glu Phe Asp Leu Thr Lys Tyr Leu Val Thr
        355                 360                 365

Glu Val Leu Lys Asp Gln Asp Lys Arg Met Asp Ala Leu Arg Glu Tyr
    370                 375                 380

Met Pro Glu Ala Gln Asn Gly Asp Trp Glu Thr Ile Val Ala Gly Gln
385                 390                 395                 400

Arg Val Gln Val Ile Lys Pro Ala Gly Phe Pro Lys Phe Gly Ser Leu
                405                 410                 415

Glu Phe Gly Thr Thr Leu Ile Asn Asn Ser Glu Gly Thr Ile Ala Gly
            420                 425                 430

Leu Leu Gly Ala Ser Pro Gly Ala Ser Ile Ala Pro Ser Ala Met Ile
        435                 440                 445

Glu Leu Leu Glu Arg Cys Phe Gly Asp Arg Met Ile Glu Trp Gly Asp
    450                 455                 460

Lys Leu Lys Asp Met Ile Pro Ser Tyr Gly Lys Lys Leu Ala Ser Glu
465                 470                 475                 480

Pro Ala Leu Phe Glu Gln Gln Trp Ala Arg Thr Gln Lys Thr Leu Lys
                485                 490                 495

Leu Glu Glu Ala
        500

<210> SEQ ID NO 3
<211> LENGTH: 2002
<212> TYPE: DNA
<213> ORGANISM: Corynebacterium glutamicum
<220> FEATURE:
<221> NAME/KEY: CDS
<222> LOCATION: (350)..(1849)
<223> OTHER INFORMATION: mqo wild-type gene

<400> SEQUENCE: 3
agtcgactga aatgttcacg tggtgaaact tccgcgatac tactcatgtt tgcgaattgc      60
acatttacta actttgcaaa ttgggggagg gggtagcgcg ggggaggaat tcgcatgaga     120 aagggaata tcccgtgctt gtttattcag ctcgaggtgg caggcgtaca ctctatattc      180
acggacaatg tgtacccacg ctttcttgta agaaacaaga agggtaacgc cccacgcgtc     240
agtcaaaaat atggccaaca cttgcattcg ggtgctggcg atcatttatg agatgacgcc     300
ttgtgttggt gttcggcaga gaactcgcgg agataaaagg aagttgaac atg tca gat    358
                                                      Met Ser Asp
                                                        1 tcc ccg aag aac gca ccg agg att acc gat gag gca gat gta gtt ctc      406
Ser Pro Lys Asn Ala Pro Arg Ile Thr Asp Glu Ala Asp Val Val Leu
    5                  10                  15 att ggt gcc ggt atc atg agc tcc acg ctg ggt gca atg ctg cgt cag      454
Ile Gly Ala Gly Ile Met Ser Ser Thr Leu Gly Ala Met Leu Arg Gln
20                  25                  30                  35

-continued

| | |
|---|---|
| ctg gag cca agc tgg act cag atc gtc ttc gag cgt ttg gat gga ccg<br>Leu Glu Pro Ser Trp Thr Gln Ile Val Phe Glu Arg Leu Asp Gly Pro<br>                40                  45                50 | 502 |
| gca caa gag tcg tcc tcc ccg tgg aac aat gca gga acc ggc cac tct<br>Ala Gln Glu Ser Ser Ser Pro Trp Asn Asn Ala Gly Thr Gly His Ser<br>            55                  60                  65 | 550 |
| gct cta tgc gag ctg aac tac acc cca gag gtt aag ggc aag gtt gaa<br>Ala Leu Cys Glu Leu Asn Tyr Thr Pro Glu Val Lys Gly Lys Val Glu<br>     70                  75                  80 | 598 |
| att gcc aag gct gta gga atc aac gag aag ttc cag gtt tcc cgt cag<br>Ile Ala Lys Ala Val Gly Ile Asn Glu Lys Phe Gln Val Ser Arg Gln<br>85                  90                  95 | 646 |
| ttc tgg tct cac ctc gtt gaa gag gga gtg ctg tct gat cct aag gaa<br>Phe Trp Ser His Leu Val Glu Glu Gly Val Leu Ser Asp Pro Lys Glu<br>100                 105              110             115 | 694 |
| ttc atc aac cct gtt cct cac gta tct ttc ggc cag ggc gca gat cag<br>Phe Ile Asn Pro Val Pro His Val Ser Phe Gly Gln Gly Ala Asp Gln<br>               120                  125             130 | 742 |
| gtt gca tac atc aag gct cgc tac gaa gct ttg aag gat cac cca ctc<br>Val Ala Tyr Ile Lys Ala Arg Tyr Glu Ala Leu Lys Asp His Pro Leu<br>          135                  140             145 | 790 |
| ttc cag ggc atg acc tac gct gac gat gaa gct acc ttc acc gag aag<br>Phe Gln Gly Met Thr Tyr Ala Asp Asp Glu Ala Thr Phe Thr Glu Lys<br>150                 155              160 | 838 |
| ctg cct ttg atg gca aag ggc cgt gac ttc tct gat cca gta gca atc<br>Leu Pro Leu Met Ala Lys Gly Arg Asp Phe Ser Asp Pro Val Ala Ile<br>     165                  170                  175 | 886 |
| tct tgg atc gat gaa ggc acc gac atc aac tac ggt gct cag acc aag<br>Ser Trp Ile Asp Glu Gly Thr Asp Ile Asn Tyr Gly Ala Gln Thr Lys<br>180               185              190             195 | 934 |
| cag tac ctg gat gca gct gaa gtt gaa ggc act gaa atc cgc tat ggc<br>Gln Tyr Leu Asp Ala Ala Glu Val Glu Gly Thr Glu Ile Arg Tyr Gly<br>               200                  205             210 | 982 |
| cac gaa gtc aag agc atc aag gct gat ggc gca aag tgg atc gtg acc<br>His Glu Val Lys Ser Ile Lys Ala Asp Gly Ala Lys Trp Ile Val Thr<br>          215                  220             225 | 1030 |
| gtc aag aac gta cac act ggc gac acc aag acc atc aag gca aac ttc<br>Val Lys Asn Val His Thr Gly Asp Thr Lys Thr Ile Lys Ala Asn Phe<br>230               235              240 | 1078 |
| gtg ttc gtc ggc gca ggc gga tac gca ctg gat ctg ctt cgc agc gca<br>Val Phe Val Gly Ala Gly Gly Tyr Ala Leu Asp Leu Leu Arg Ser Ala<br>     245                  250                  255 | 1126 |
| ggc atc cca cag gtc aag ggc ttc gct gga ttc cca gta tcc ggc ctg<br>Gly Ile Pro Gln Val Lys Gly Phe Ala Gly Phe Pro Val Ser Gly Leu<br>260               265              270             275 | 1174 |
| tgg ctt cgt tgc acc aac gag gaa ctg atc gag cag cac gca gcc aag<br>Trp Leu Arg Cys Thr Asn Glu Glu Leu Ile Glu Gln His Ala Ala Lys<br>               280                  285             290 | 1222 |
| gta tat ggc aag gca tct gtt ggc gct cct cca atg tct gtt cct cac<br>Val Tyr Gly Lys Ala Ser Val Gly Ala Pro Pro Met Ser Val Pro His<br>          295                  300             305 | 1270 |
| ctt gac acc cgc gtt atc gag ggt gaa aag ggt ctc ctc ttt gga cct<br>Leu Asp Thr Arg Val Ile Glu Gly Glu Lys Gly Leu Leu Phe Gly Pro<br>310               315              320 | 1318 |
| tac ggt ggc tgg acc cct aag ttc ttg aag gaa ggc tcc tac ctg gac<br>Tyr Gly Gly Trp Thr Pro Lys Phe Leu Lys Glu Gly Ser Tyr Leu Asp<br>     325                  330                  335 | 1366 |
| ctg ttc aag tcc atc cgc cca gac aac att cct tcc tac ctt ggc gtt<br>Leu Phe Lys Ser Ile Arg Pro Asp Asn Ile Pro Ser Tyr Leu Gly Val | 1414 |

-continued

```
            340             345             350             355
gct gct cag gaa ttt gat ctg acc aag tac ctt gtc act gaa gtt ctc    1462
Ala Ala Gln Glu Phe Asp Leu Thr Lys Tyr Leu Val Thr Glu Val Leu
                    360             365             370 aag gac cag gac aag cgt atg gat gct ctt cgc gag tac atg cca gag    1510
Lys Asp Gln Asp Lys Arg Met Asp Ala Leu Arg Glu Tyr Met Pro Glu
            375             380             385 gca caa aac ggc gat tgg gag acc atc gtt gcc gga cag cgt gtt cag    1558
Ala Gln Asn Gly Asp Trp Glu Thr Ile Val Ala Gly Gln Arg Val Gln
        390             395             400 gtt att aag cct gca gga ttc cct aag ttc ggt tcc ctg gaa ttc ggc    1606
Val Ile Lys Pro Ala Gly Phe Pro Lys Phe Gly Ser Leu Glu Phe Gly
    405             410             415 acc acc ttg atc aac aac tcc gaa ggc acc atc gcc gga ttg ctc ggt    1654
Thr Thr Leu Ile Asn Asn Ser Glu Gly Thr Ile Ala Gly Leu Leu Gly
420             425             430             435 gct tcc cct gga gca tcc atc gca cct tcc gca atg atc gag ctg ctt    1702
Ala Ser Pro Gly Ala Ser Ile Ala Pro Ser Ala Met Ile Glu Leu Leu
                440             445             450 gag cgt tgc ttc ggt gac cgc atg atc gag tgg ggc gac aag ctg aag    1750
Glu Arg Cys Phe Gly Asp Arg Met Ile Glu Trp Gly Asp Lys Leu Lys
            455             460             465 gac atg atc cct tcc tac ggc aag aag ctt gct tcc gag cca gca ctg    1798
Asp Met Ile Pro Ser Tyr Gly Lys Lys Leu Ala Ser Glu Pro Ala Leu
        470             475             480 ttt gag cag cag tgg gca cgc acc cag aag acc ctg aag ctt gag gaa    1846
Phe Glu Gln Gln Trp Ala Arg Thr Gln Lys Thr Leu Lys Leu Glu Glu
    485             490             495 gcc taaatcttct aactgctttc tttaaagcac ccgcacatgt ctgttgaggt         1899
Ala
500 ttcacctgcg agacaatct ccgccttcat gggttggaac tgacacagtt gaaggcatgt   1959 cgggtgcttt gcgtattctt tgccagtgtg atttaggcga cac                    2002
```

<210> SEQ ID NO 4
<211> LENGTH: 500
<212> TYPE: PRT
<213> ORGANISM: Corynebacterium glutamicum

<400> SEQUENCE: 4

```
Met Ser Asp Ser Pro Lys Asn Ala Pro Arg Ile Thr Asp Glu Ala Asp
1               5                   10                  15

Val Val Leu Ile Gly Ala Gly Ile Met Ser Ser Thr Leu Gly Ala Met
                20                  25                  30

Leu Arg Gln Leu Glu Pro Ser Trp Thr Gln Ile Val Phe Glu Arg Leu
            35                  40                  45

Asp Gly Pro Ala Gln Glu Ser Ser Pro Trp Asn Asn Ala Gly Thr
    50                  55                  60

Gly His Ser Ala Leu Cys Glu Leu Asn Tyr Thr Pro Glu Val Lys Gly
65                  70                  75                  80

Lys Val Glu Ile Ala Lys Ala Val Gly Ile Asn Glu Lys Phe Gln Val
                85                  90                  95

Ser Arg Gln Phe Trp Ser His Leu Val Glu Glu Gly Val Leu Ser Asp
            100                 105                 110

Pro Lys Glu Phe Ile Asn Pro Val Pro His Val Ser Phe Gly Gln Gly
        115                 120                 125

Ala Asp Gln Val Ala Tyr Ile Lys Ala Arg Tyr Glu Ala Leu Lys Asp
```

```
                130                 135                 140
His Pro Leu Phe Gln Gly Met Thr Tyr Ala Asp Asp Glu Ala Thr Phe
145                 150                 155                 160

Thr Glu Lys Leu Pro Leu Met Ala Lys Gly Arg Asp Phe Ser Asp Pro
                165                 170                 175

Val Ala Ile Ser Trp Ile Asp Glu Gly Thr Asp Ile Asn Tyr Gly Ala
                180                 185                 190

Gln Thr Lys Gln Tyr Leu Asp Ala Ala Glu Val Glu Gly Thr Glu Ile
                195                 200                 205

Arg Tyr Gly His Glu Val Lys Ser Ile Lys Ala Asp Gly Ala Lys Trp
210                 215                 220

Ile Val Thr Val Lys Asn Val His Thr Gly Asp Thr Lys Thr Ile Lys
225                 230                 235                 240

Ala Asn Phe Val Phe Val Gly Ala Gly Tyr Ala Leu Asp Leu Leu
                245                 250                 255

Arg Ser Ala Gly Ile Pro Gln Val Lys Gly Phe Ala Gly Phe Pro Val
                260                 265                 270

Ser Gly Leu Trp Leu Arg Cys Thr Asn Glu Glu Leu Ile Glu Gln His
                275                 280                 285

Ala Ala Lys Val Tyr Gly Lys Ala Ser Val Gly Ala Pro Pro Met Ser
                290                 295                 300

Val Pro His Leu Asp Thr Arg Val Ile Glu Gly Lys Gly Leu Leu
305                 310                 315                 320

Phe Gly Pro Tyr Gly Gly Trp Thr Pro Lys Phe Leu Lys Glu Gly Ser
                325                 330                 335

Tyr Leu Asp Leu Phe Lys Ser Ile Arg Pro Asp Asn Ile Pro Ser Tyr
                340                 345                 350

Leu Gly Val Ala Ala Gln Glu Phe Asp Leu Thr Lys Tyr Leu Val Thr
                355                 360                 365

Glu Val Leu Lys Asp Gln Asp Lys Arg Met Asp Ala Leu Arg Glu Tyr
                370                 375                 380

Met Pro Glu Ala Gln Asn Gly Asp Trp Glu Thr Ile Val Ala Gly Gln
385                 390                 395                 400

Arg Val Gln Val Ile Lys Pro Ala Gly Phe Pro Lys Phe Gly Ser Leu
                405                 410                 415

Glu Phe Gly Thr Thr Leu Ile Asn Asn Ser Glu Gly Thr Ile Ala Gly
                420                 425                 430

Leu Leu Gly Ala Ser Pro Gly Ala Ser Ile Ala Pro Ser Ala Met Ile
                435                 440                 445

Glu Leu Leu Glu Arg Cys Phe Gly Asp Arg Met Ile Glu Trp Gly Asp
                450                 455                 460

Lys Leu Lys Asp Met Ile Pro Ser Tyr Gly Lys Lys Leu Ala Ser Glu
465                 470                 475                 480

Pro Ala Leu Phe Glu Gln Gln Trp Ala Arg Thr Gln Lys Thr Leu Lys
                485                 490                 495

Leu Glu Glu Ala
                500

<210> SEQ ID NO 5
<211> LENGTH: 1503
<212> TYPE: DNA
<213> ORGANISM: Corynebacterium glutamicum
<220> FEATURE:
<221> NAME/KEY: CDS
<222> LOCATION: (1)..(1500)
```

<223> OTHER INFORMATION: mqo allele
<220> FEATURE:
<221> NAME/KEY: mutation
<222> LOCATION: (332)..(332)
<223> OTHER INFORMATION: Transition: replacement of cytosine with
       thymine

<400> SEQUENCE: 5

```
atg tca gat tcc ccg aag aac gca ccg agg att acc gat gag gca gat        48
Met Ser Asp Ser Pro Lys Asn Ala Pro Arg Ile Thr Asp Glu Ala Asp
1               5                  10                  15 gta gtt ctc att ggt gcc ggt atc atg agc tcc acg ctg ggt gca atg        96
Val Val Leu Ile Gly Ala Gly Ile Met Ser Ser Thr Leu Gly Ala Met
             20                  25                  30 ctg cgt cag ctg gag cca agc tgg act cag atc gtc ttc gag cgt ttg       144
Leu Arg Gln Leu Glu Pro Ser Trp Thr Gln Ile Val Phe Glu Arg Leu
         35                  40                  45 gat gga ccg gca caa gag tcg tcc tcc ccg tgg aac aat gca gga acc       192
Asp Gly Pro Ala Gln Glu Ser Ser Ser Pro Trp Asn Asn Ala Gly Thr
 50                  55                  60 ggc cac tct gct cta tgc gag ctg aac tac acc cca gag gtt aag ggc       240
Gly His Ser Ala Leu Cys Glu Leu Asn Tyr Thr Pro Glu Val Lys Gly
 65                  70                  75                  80 aag gtt gaa att gcc aag gct gta gga atc aac gag aag ttc cag gtt       288
Lys Val Glu Ile Ala Lys Ala Val Gly Ile Asn Glu Lys Phe Gln Val
                 85                  90                  95 tcc cgt cag ttc tgg tct cac ctc gtt gaa gag gga gtg ctg ttt gat       336
Ser Arg Gln Phe Trp Ser His Leu Val Glu Glu Gly Val Leu Phe Asp
            100                 105                 110 cct aag gaa ttc atc aac cct gtt cct cac gta tct ttc ggc cag ggc       384
Pro Lys Glu Phe Ile Asn Pro Val Pro His Val Ser Phe Gly Gln Gly
        115                 120                 125 gca gat cag gtt gca tac atc aag gct cgc tac gaa gct ttg aag gat       432
Ala Asp Gln Val Ala Tyr Ile Lys Ala Arg Tyr Glu Ala Leu Lys Asp
130                 135                 140 cac cca ctc ttc cag ggc atg acc tac gct gac gat gaa gct acc ttc       480
His Pro Leu Phe Gln Gly Met Thr Tyr Ala Asp Asp Glu Ala Thr Phe
145                 150                 155                 160 acc gag aag ctg cct ttg atg gca aag ggc cgt gac ttc tct gat cca       528
Thr Glu Lys Leu Pro Leu Met Ala Lys Gly Arg Asp Phe Ser Asp Pro
                165                 170                 175 gta gca atc tct tgg atc gat gaa ggc acc gac atc aac tac ggt gct       576
Val Ala Ile Ser Trp Ile Asp Glu Gly Thr Asp Ile Asn Tyr Gly Ala
            180                 185                 190 cag acc aag cag tac ctg gat gca gct gaa gtt gaa ggc act gaa atc       624
Gln Thr Lys Gln Tyr Leu Asp Ala Ala Glu Val Glu Gly Thr Glu Ile
        195                 200                 205 cgc tat ggc cac gaa gtc aag agc atc aag gct gat ggc gca aag tgg       672
Arg Tyr Gly His Glu Val Lys Ser Ile Lys Ala Asp Gly Ala Lys Trp
    210                 215                 220 atc gtg acc gtc aag aac gta cac act ggc gac acc aag acc atc aag       720
Ile Val Thr Val Lys Asn Val His Thr Gly Asp Thr Lys Thr Ile Lys
225                 230                 235                 240 gca aac ttc gtg ttc gtc ggc gca ggc gga tac gca ctg gat ctg ctt       768
Ala Asn Phe Val Phe Val Gly Ala Gly Gly Tyr Ala Leu Asp Leu Leu
                245                 250                 255 cgc agc gca ggc atc cca cag gtc aag ggc ttc gct gga ttc cca gta       816
Arg Ser Ala Gly Ile Pro Gln Val Lys Gly Phe Ala Gly Phe Pro Val
            260                 265                 270 tcc ggc ctg tgg ctt cgt tgc acc aac gag gaa ctg atc gag cag cac       864
Ser Gly Leu Trp Leu Arg Cys Thr Asn Glu Glu Leu Ile Glu Gln His
```

```
                   275                 280                 285
gca gcc aag gta tat ggc aag gca tct gtt ggc gct cct cca atg tct        912
Ala Ala Lys Val Tyr Gly Lys Ala Ser Val Gly Ala Pro Pro Met Ser
    290                 295                 300 gtt cct cac ctt gac acc cgc gtt atc gag ggt gaa aag ggt ctg ctc        960
Val Pro His Leu Asp Thr Arg Val Ile Glu Gly Glu Lys Gly Leu Leu
305                 310                 315                 320 ttt gga cct tac ggt ggc tgg acc cct aag ttc ttg aag gaa ggc tcc       1008
Phe Gly Pro Tyr Gly Gly Trp Thr Pro Lys Phe Leu Lys Glu Gly Ser
                325                 330                 335 tac ctg gac ctg ttc aag tcc atc cgc cca gac aac att cct tcc tac       1056
Tyr Leu Asp Leu Phe Lys Ser Ile Arg Pro Asp Asn Ile Pro Ser Tyr
            340                 345                 350 ctt ggc gtt gct gct cag gaa ttt gat ctg acc aag tac ctt gtc act       1104
Leu Gly Val Ala Ala Gln Glu Phe Asp Leu Thr Lys Tyr Leu Val Thr
        355                 360                 365 gaa gtt ctc aag gac cag gac aag cgt atg gat gct ctt cgc gag tac       1152
Glu Val Leu Lys Asp Gln Asp Lys Arg Met Asp Ala Leu Arg Glu Tyr
    370                 375                 380 atg cca gag gca caa aac ggc gat tgg gag acc atc gtt gcc gga cag       1200
Met Pro Glu Ala Gln Asn Gly Asp Trp Glu Thr Ile Val Ala Gly Gln
385                 390                 395                 400 cgt gtt cag gtt att aag cct gca gga ttc cct aag ttc ggt tcc ctg       1248
Arg Val Gln Val Ile Lys Pro Ala Gly Phe Pro Lys Phe Gly Ser Leu
                405                 410                 415 gaa ttc ggc acc acc ttg atc aac aac tcc gaa ggc acc atc gcc gga       1296
Glu Phe Gly Thr Thr Leu Ile Asn Asn Ser Glu Gly Thr Ile Ala Gly
            420                 425                 430 ttg ctc ggt gct tcc cct gga gca tcc atc gca cct tcc gca atg atc       1344
Leu Leu Gly Ala Ser Pro Gly Ala Ser Ile Ala Pro Ser Ala Met Ile
        435                 440                 445 gag ctg ctt gag cgt tgc ttc ggt gac cgc atg atc gag tgg ggc gac       1392
Glu Leu Leu Glu Arg Cys Phe Gly Asp Arg Met Ile Glu Trp Gly Asp
    450                 455                 460 aag ctg aag gac atg atc cct tcc tac ggc aag aag ctt gct tcc gag       1440
Lys Leu Lys Asp Met Ile Pro Ser Tyr Gly Lys Lys Leu Ala Ser Glu
465                 470                 475                 480 cca gca ctg ttt gag cag cag tgg gca cgc acc cag aag acc ctg aag       1488
Pro Ala Leu Phe Glu Gln Gln Trp Ala Arg Thr Gln Lys Thr Leu Lys
                485                 490                 495 ctt gag gaa gcc taa                                                    1503
Leu Glu Glu Ala
            500

<210> SEQ ID NO 6
<211> LENGTH: 500
<212> TYPE: PRT
<213> ORGANISM: Corynebacterium glutamicum

<400> SEQUENCE: 6

Met Ser Asp Ser Pro Lys Asn Ala Pro Arg Ile Thr Asp Glu Ala Asp
1               5                   10                  15

Val Val Leu Ile Gly Ala Gly Ile Met Ser Ser Thr Leu Gly Ala Met
                20                  25                  30

Leu Arg Gln Leu Glu Pro Ser Trp Thr Gln Ile Val Phe Glu Arg Leu
            35                  40                  45

Asp Gly Pro Ala Gln Glu Ser Ser Pro Trp Asn Asn Ala Gly Thr
        50                  55                  60

Gly His Ser Ala Leu Cys Glu Leu Asn Tyr Thr Pro Glu Val Lys Gly
```

-continued

```
                65                  70                  75                  80
Lys Val Glu Ile Ala Lys Ala Val Gly Ile Asn Glu Lys Phe Gln Val
                    85                  90                  95
Ser Arg Gln Phe Trp Ser His Leu Val Glu Glu Gly Val Leu Phe Asp
                   100                 105                 110
Pro Lys Glu Phe Ile Asn Pro Val Pro His Val Ser Phe Gly Gln Gly
                   115                 120                 125
Ala Asp Gln Val Ala Tyr Ile Lys Ala Arg Tyr Glu Ala Leu Lys Asp
                   130                 135                 140
His Pro Leu Phe Gln Gly Met Thr Tyr Ala Asp Asp Glu Ala Thr Phe
145                150                 155                 160
Thr Glu Lys Leu Pro Leu Met Ala Lys Gly Arg Asp Phe Ser Asp Pro
                   165                 170                 175
Val Ala Ile Ser Trp Ile Asp Glu Gly Thr Asp Ile Asn Tyr Gly Ala
                   180                 185                 190
Gln Thr Lys Gln Tyr Leu Asp Ala Ala Glu Val Glu Gly Thr Glu Ile
                   195                 200                 205
Arg Tyr Gly His Glu Val Lys Ser Ile Lys Ala Asp Gly Ala Lys Trp
                   210                 215                 220
Ile Val Thr Val Lys Asn Val His Thr Gly Asp Thr Lys Thr Ile Lys
225                230                 235                 240
Ala Asn Phe Val Phe Val Gly Ala Gly Gly Tyr Ala Leu Asp Leu Leu
                   245                 250                 255
Arg Ser Ala Gly Ile Pro Gln Val Lys Gly Phe Ala Gly Phe Pro Val
                   260                 265                 270
Ser Gly Leu Trp Leu Arg Cys Thr Asn Glu Glu Leu Ile Glu Gln His
                   275                 280                 285
Ala Ala Lys Val Tyr Gly Lys Ala Ser Val Gly Ala Pro Pro Met Ser
                   290                 295                 300
Val Pro His Leu Asp Thr Arg Val Ile Glu Gly Glu Lys Gly Leu Leu
305                310                 315                 320
Phe Gly Pro Tyr Gly Gly Trp Thr Pro Lys Phe Leu Lys Glu Gly Ser
                   325                 330                 335
Tyr Leu Asp Leu Phe Lys Ser Ile Arg Pro Asp Asn Ile Pro Ser Tyr
                   340                 345                 350
Leu Gly Val Ala Ala Gln Glu Phe Asp Leu Thr Lys Tyr Leu Val Thr
                   355                 360                 365
Glu Val Leu Lys Asp Gln Asp Lys Arg Met Asp Ala Leu Arg Glu Tyr
                   370                 375                 380
Met Pro Glu Ala Gln Asn Gly Asp Trp Glu Thr Ile Val Ala Gly Gln
385                390                 395                 400
Arg Val Gln Val Ile Lys Pro Ala Gly Phe Pro Lys Phe Gly Ser Leu
                   405                 410                 415
Glu Phe Gly Thr Thr Leu Ile Asn Asn Ser Glu Gly Thr Ile Ala Gly
                   420                 425                 430
Leu Leu Gly Ala Ser Pro Gly Ala Ser Ile Ala Pro Ser Ala Met Ile
                   435                 440                 445
Glu Leu Leu Glu Arg Cys Phe Gly Asp Arg Met Ile Glu Trp Gly Asp
                   450                 455                 460
Lys Leu Lys Asp Met Ile Pro Ser Tyr Gly Lys Lys Leu Ala Ser Glu
465                470                 475                 480
Pro Ala Leu Phe Glu Gln Gln Trp Ala Arg Thr Gln Lys Thr Leu Lys
                   485                 490                 495
```

-continued

```
Leu Glu Glu Ala
        500

<210> SEQ ID NO 7
<211> LENGTH: 1503
<212> TYPE: DNA
<213> ORGANISM: Corynebacterium glutamicum
<220> FEATURE:
<221> NAME/KEY: CDS
<222> LOCATION: (1)..(1500)
<223> OTHER INFORMATION: mqo allele
<220> FEATURE:
<221> NAME/KEY: mutation
<222> LOCATION: (331)..(331)
<223> OTHER INFORMATION: Transversion: replacement of thymine with
      guanine

<400> SEQUENCE: 7 atg tca gat tcc ccg aag aac gca ccg agg att acc gat gag gca gat        48
Met Ser Asp Ser Pro Lys Asn Ala Pro Arg Ile Thr Asp Glu Ala Asp
1               5                   10                  15 gta gtt ctc att ggt gcc ggt atc atg agc tcc acg ctg ggt gca atg        96
Val Val Leu Ile Gly Ala Gly Ile Met Ser Ser Thr Leu Gly Ala Met
            20                  25                  30 ctg cgt cag ctg gag cca agc tgg act cag atc gtc ttc gag cgt ttg       144
Leu Arg Gln Leu Glu Pro Ser Trp Thr Gln Ile Val Phe Glu Arg Leu
        35                  40                  45 gat gga ccg gca caa gag tcg tcc tcc ccg tgg aac aat gca gga acc       192
Asp Gly Pro Ala Gln Glu Ser Ser Ser Pro Trp Asn Asn Ala Gly Thr
    50                  55                  60 ggc cac tct gct cta tgc gag ctg aac tac acc cca gag gtt aag ggc       240
Gly His Ser Ala Leu Cys Glu Leu Asn Tyr Thr Pro Glu Val Lys Gly
65                  70                  75                  80 aag gtt gaa att gcc aag gct gta gga atc aac gag aag ttc cag gtt       288
Lys Val Glu Ile Ala Lys Ala Val Gly Ile Asn Glu Lys Phe Gln Val
                85                  90                  95 tcc cgt cag ttc tgg tct cac ctc gtt gaa gag gga gtg ctg gct gat       336
Ser Arg Gln Phe Trp Ser His Leu Val Glu Glu Gly Val Leu Ala Asp
            100                 105                 110 cct aag gaa ttc atc aac cct gtt cct cac gta tct ttc ggc cag ggc       384
Pro Lys Glu Phe Ile Asn Pro Val Pro His Val Ser Phe Gly Gln Gly
        115                 120                 125 gca gat cag gtt gca tac atc aag gct cgc tac gaa gct ttg aag gat       432
Ala Asp Gln Val Ala Tyr Ile Lys Ala Arg Tyr Glu Ala Leu Lys Asp
    130                 135                 140 cac cca ctc ttc cag ggc atg acc tac gct gac gat gaa gct acc ttc       480
His Pro Leu Phe Gln Gly Met Thr Tyr Ala Asp Asp Glu Ala Thr Phe
145                 150                 155                 160 acc gag aag ctg cct ttg atg gca aag ggc cgt gac ttc tct gat cca       528
Thr Glu Lys Leu Pro Leu Met Ala Lys Gly Arg Asp Phe Ser Asp Pro
                165                 170                 175 gta gca atc tct tgg atc gat gaa ggc acc gac atc aac tac ggt gct       576
Val Ala Ile Ser Trp Ile Asp Glu Gly Thr Asp Ile Asn Tyr Gly Ala
            180                 185                 190 cag acc aag cag tac ctg gat gca gct gaa gtt gaa ggc act gaa atc       624
Gln Thr Lys Gln Tyr Leu Asp Ala Ala Glu Val Glu Gly Thr Glu Ile
        195                 200                 205 cgc tat ggc cac gaa gtc aag agc atc aag gct gat ggc gca aag tgg       672
Arg Tyr Gly His Glu Val Lys Ser Ile Lys Ala Asp Gly Ala Lys Trp
    210                 215                 220 atc gtg acc gtc aag aac gta cac act ggc gac acc aag acc atc aag       720
Ile Val Thr Val Lys Asn Val His Thr Gly Asp Thr Lys Thr Ile Lys
```

```
gca aac ttc gtg ttc gtc ggc gca ggc gga tac gca ctg gat ctg ctt    768
Ala Asn Phe Val Phe Val Gly Ala Gly Gly Tyr Ala Leu Asp Leu Leu
            245                 250                 255 cgc agc gca ggc atc cca cag gtc aag ggc ttc gct gga ttc cca gta    816
Arg Ser Ala Gly Ile Pro Gln Val Lys Gly Phe Ala Gly Phe Pro Val
        260                 265                 270 tcc ggc ctg tgg ctt cgt tgc acc aac gag gaa ctg atc gag cag cac    864
Ser Gly Leu Trp Leu Arg Cys Thr Asn Glu Glu Leu Ile Glu Gln His
            275                 280                 285 gca gcc aag gta tat ggc aag gca tct gtt ggc gct cct cca atg tct    912
Ala Ala Lys Val Tyr Gly Lys Ala Ser Val Gly Ala Pro Pro Met Ser
        290                 295                 300 gtt cct cac ctt gac acc cgc gtt atc gag ggt gaa aag ggt ctg ctc    960
Val Pro His Leu Asp Thr Arg Val Ile Glu Gly Glu Lys Gly Leu Leu
305                 310                 315                 320 ttt gga cct tac ggt ggc tgg acc cct aag ttc ttg aag gaa ggc tcc   1008
Phe Gly Pro Tyr Gly Gly Trp Thr Pro Lys Phe Leu Lys Glu Gly Ser
                325                 330                 335 tac ctg gac ctg ttc aag tcc atc cgc cca gac aac att cct tcc tac   1056
Tyr Leu Asp Leu Phe Lys Ser Ile Arg Pro Asp Asn Ile Pro Ser Tyr
            340                 345                 350 ctt ggc gtt gct gct cag gaa ttt gat ctg acc aag tac ctt gtc act   1104
Leu Gly Val Ala Ala Gln Glu Phe Asp Leu Thr Lys Tyr Leu Val Thr
        355                 360                 365 gaa gtt ctc aag gac cag gac aag cgt atg gat gct ctt cgc gag tac   1152
Glu Val Leu Lys Asp Gln Asp Lys Arg Met Asp Ala Leu Arg Glu Tyr
    370                 375                 380 atg cca gag gca caa aac ggc gat tgg gag acc atc gtt gcc gga cag   1200
Met Pro Glu Ala Gln Asn Gly Asp Trp Glu Thr Ile Val Ala Gly Gln
385                 390                 395                 400 cgt gtt cag gtt att aag cct gca gga ttc cct aag ttc ggt tcc ctg   1248
Arg Val Gln Val Ile Lys Pro Ala Gly Phe Pro Lys Phe Gly Ser Leu
                405                 410                 415 gaa ttc ggc acc acc ttg atc aac aac tcc gaa ggc acc atc gcc gga   1296
Glu Phe Gly Thr Thr Leu Ile Asn Asn Ser Glu Gly Thr Ile Ala Gly
            420                 425                 430 ttg ctc ggt gct tcc cct gga gca tcc atc gca cct tcc gca atg atc   1344
Leu Leu Gly Ala Ser Pro Gly Ala Ser Ile Ala Pro Ser Ala Met Ile
        435                 440                 445 gag ctg ctt gag cgt tgc ttc ggt gac cgc atg atc gag tgg ggc gac   1392
Glu Leu Leu Glu Arg Cys Phe Gly Asp Arg Met Ile Glu Trp Gly Asp
    450                 455                 460 aag ctg aag gac atg atc cct tcc tac ggc aag aag ctt gct tcc gag   1440
Lys Leu Lys Asp Met Ile Pro Ser Tyr Gly Lys Lys Leu Ala Ser Glu
465                 470                 475                 480 cca gca ctg ttt gag cag cag tgg gca cgc acc cag aag acc ctg aag   1488
Pro Ala Leu Phe Glu Gln Gln Trp Ala Arg Thr Gln Lys Thr Leu Lys
                485                 490                 495 ctt gag gaa gcc taa                                               1503
Leu Glu Glu Ala
        500
```

<210> SEQ ID NO 8
<211> LENGTH: 500
<212> TYPE: PRT
<213> ORGANISM: Corynebacterium glutamicum

<400> SEQUENCE: 8

Met Ser Asp Ser Pro Lys Asn Ala Pro Arg Ile Thr Asp Glu Ala Asp

```
       1               5                   10                  15
Val Val Leu Ile Gly Ala Gly Ile Met Ser Ser Thr Leu Gly Ala Met
                    20                  25                  30

Leu Arg Gln Leu Glu Pro Ser Trp Thr Gln Ile Val Phe Glu Arg Leu
                    35                  40                  45

Asp Gly Pro Ala Gln Glu Ser Ser Pro Trp Asn Asn Ala Gly Thr
 50                      55                  60

Gly His Ser Ala Leu Cys Glu Leu Asn Tyr Thr Pro Glu Val Lys Gly
 65                      70                  75                  80

Lys Val Glu Ile Ala Lys Ala Val Gly Ile Asn Glu Lys Phe Gln Val
                    85                  90                  95

Ser Arg Gln Phe Trp Ser His Leu Val Glu Glu Gly Val Leu Ala Asp
                    100                 105                 110

Pro Lys Glu Phe Ile Asn Pro Val Pro His Val Ser Phe Gly Gln Gly
                    115                 120                 125

Ala Asp Gln Val Ala Tyr Ile Lys Ala Arg Tyr Glu Ala Leu Lys Asp
 130                     135                 140

His Pro Leu Phe Gln Gly Met Thr Tyr Ala Asp Asp Glu Ala Thr Phe
145                      150                 155                 160

Thr Glu Lys Leu Pro Leu Met Ala Lys Gly Arg Asp Phe Ser Asp Pro
                    165                 170                 175

Val Ala Ile Ser Trp Ile Asp Glu Gly Thr Asp Ile Asn Tyr Gly Ala
                    180                 185                 190

Gln Thr Lys Gln Tyr Leu Asp Ala Ala Glu Val Glu Gly Thr Glu Ile
                    195                 200                 205

Arg Tyr Gly His Glu Val Lys Ser Ile Lys Ala Asp Gly Ala Lys Trp
 210                     215                 220

Ile Val Thr Val Lys Asn Val His Thr Gly Asp Thr Lys Thr Ile Lys
225                      230                 235                 240

Ala Asn Phe Val Phe Gly Ala Gly Tyr Ala Leu Asp Leu Leu
                    245                 250                 255

Arg Ser Ala Gly Ile Pro Gln Val Lys Gly Phe Ala Gly Phe Pro Val
                    260                 265                 270

Ser Gly Leu Trp Leu Arg Cys Thr Asn Glu Glu Leu Ile Glu Gln His
                    275                 280                 285

Ala Ala Lys Val Tyr Gly Lys Ala Ser Val Gly Ala Pro Pro Met Ser
                    290                 295                 300

Val Pro His Leu Asp Thr Arg Val Ile Glu Gly Lys Gly Leu Leu
305                      310                 315                 320

Phe Gly Pro Tyr Gly Gly Trp Thr Pro Lys Phe Leu Lys Glu Gly Ser
                    325                 330                 335

Tyr Leu Asp Leu Phe Lys Ser Ile Arg Pro Asp Asn Ile Pro Ser Tyr
                    340                 345                 350

Leu Gly Val Ala Ala Gln Glu Phe Asp Leu Thr Lys Tyr Leu Val Thr
                    355                 360                 365

Glu Val Leu Lys Asp Gln Asp Lys Arg Met Asp Ala Leu Arg Glu Tyr
 370                     375                 380

Met Pro Glu Ala Gln Asn Gly Asp Trp Glu Thr Ile Val Ala Gly Gln
385                      390                 395                 400

Arg Val Gln Val Ile Lys Pro Ala Gly Phe Pro Lys Phe Gly Ser Leu
                    405                 410                 415

Glu Phe Gly Thr Thr Leu Ile Asn Asn Ser Glu Gly Thr Ile Ala Gly
                    420                 425                 430
```

```
Leu Leu Gly Ala Ser Pro Gly Ala Ser Ile Ala Pro Ser Ala Met Ile
            435                 440                 445

Glu Leu Leu Glu Arg Cys Phe Gly Asp Arg Met Ile Glu Trp Gly Asp
    450                 455                 460

Lys Leu Lys Asp Met Ile Pro Ser Tyr Gly Lys Lys Leu Ala Ser Glu
465                 470                 475                 480

Pro Ala Leu Phe Glu Gln Gln Trp Ala Arg Thr Gln Lys Thr Leu Lys
                485                 490                 495

Leu Glu Glu Ala
            500

<210> SEQ ID NO 9
<211> LENGTH: 1503
<212> TYPE: DNA
<213> ORGANISM: Corynebacterium glutamicum
<220> FEATURE:
<221> NAME/KEY: CDS
<222> LOCATION: (1)..(1500)
<223> OTHER INFORMATION: mqo allele
<220> FEATURE:
<221> NAME/KEY: mutation
<222> LOCATION: (331)..(331)
<223> OTHER INFORMATION: Transversion: replacement of thymine with
      guanine
<220> FEATURE:
<221> NAME/KEY: mutation
<222> LOCATION: (601)..(601)
<223> OTHER INFORMATION: Transversion: replacement of guanine with
      thymine

<400> SEQUENCE: 9 atg tca gat tcc ccg aag aac gca ccg agg att acc gat gag gca gat      48
Met Ser Asp Ser Pro Lys Asn Ala Pro Arg Ile Thr Asp Glu Ala Asp
1               5                   10                  15 gta gtt ctc att ggt gcc ggt atc atg agc tcc acg ctg ggt gca atg      96
Val Val Leu Ile Gly Ala Gly Ile Met Ser Ser Thr Leu Gly Ala Met
                20                  25                  30 ctg cgt cag ctg gag cca agc tgg act cag atc gtc ttc gag cgt ttg     144
Leu Arg Gln Leu Glu Pro Ser Trp Thr Gln Ile Val Phe Glu Arg Leu
            35                  40                  45 gat gga ccg gca caa gag tcg tcc tcc ccg tgg aac aat gca gga acc     192
Asp Gly Pro Ala Gln Glu Ser Ser Ser Pro Trp Asn Asn Ala Gly Thr
        50                  55                  60 ggc cac tct gct cta tgc gag ctg aac tac acc cca gag gtt aag ggc     240
Gly His Ser Ala Leu Cys Glu Leu Asn Tyr Thr Pro Glu Val Lys Gly
65                  70                  75                  80 aag gtt gaa att gcc aag gct gta gga atc aac gag aag ttc cag gtt     288
Lys Val Glu Ile Ala Lys Ala Val Gly Ile Asn Glu Lys Phe Gln Val
                85                  90                  95 tcc cgt cag ttc tgg tct cac ctc gtt gaa gag gga gtg ctg gct gat     336
Ser Arg Gln Phe Trp Ser His Leu Val Glu Glu Gly Val Leu Ala Asp
            100                 105                 110 cct aag gaa ttc atc aac cct gtt cct cac gta tct ttc ggc cag ggc     384
Pro Lys Glu Phe Ile Asn Pro Val Pro His Val Ser Phe Gly Gln Gly
        115                 120                 125 gca gat cag gtt gca tac atc aag gct cgc tac gaa gct ttg aag gat     432
Ala Asp Gln Val Ala Tyr Ile Lys Ala Arg Tyr Glu Ala Leu Lys Asp
    130                 135                 140 cac cca ctc ttc cag ggc atg acc tac gct gac gat gaa gct acc ttc     480
His Pro Leu Phe Gln Gly Met Thr Tyr Ala Asp Asp Glu Ala Thr Phe
145                 150                 155                 160 acc gag aag ctg cct ttg atg gca aag ggc cgt gac ttc tct gat cca     528
```

```
Thr Glu Lys Leu Pro Leu Met Ala Lys Gly Arg Asp Phe Ser Asp Pro
            165                 170                 175 gta gca atc tct tgg atc gat gaa ggc acc gac atc aac tac ggt gct        576
Val Ala Ile Ser Trp Ile Asp Glu Gly Thr Asp Ile Asn Tyr Gly Ala
            180                 185                 190 cag acc aag cag tac ctg gat gca tct gaa gtt gaa ggc act gaa atc        624
Gln Thr Lys Gln Tyr Leu Asp Ala Ser Glu Val Glu Gly Thr Glu Ile
            195                 200                 205 cgc tat ggc cac gaa gtc aag agc atc aag gct gat ggc gca aag tgg        672
Arg Tyr Gly His Glu Val Lys Ser Ile Lys Ala Asp Gly Ala Lys Trp
    210                 215                 220 atc gtg acc gtc aag aac gta cac act ggc gac acc aag acc atc aag        720
Ile Val Thr Val Lys Asn Val His Thr Gly Asp Thr Lys Thr Ile Lys
225                 230                 235                 240 gca aac ttc gtg ttc gtc ggc gca ggc gga tac gca ctg gat ctg ctt        768
Ala Asn Phe Val Phe Val Gly Ala Gly Gly Tyr Ala Leu Asp Leu Leu
                245                 250                 255 cgc agc gca ggc atc cca cag gtc aag ggc ttc gct gga ttc cca gta        816
Arg Ser Ala Gly Ile Pro Gln Val Lys Gly Phe Ala Gly Phe Pro Val
            260                 265                 270 tcc ggc ctg tgg ctt cgt tgc acc aac gag gaa ctg atc gag cag cac        864
Ser Gly Leu Trp Leu Arg Cys Thr Asn Glu Glu Leu Ile Glu Gln His
            275                 280                 285 gca gcc aag gta tat ggc aag gca tct gtt ggc gct cct cca atg tct        912
Ala Ala Lys Val Tyr Gly Lys Ala Ser Val Gly Ala Pro Pro Met Ser
    290                 295                 300 gtt cct cac ctt gac acc cgc gtt atc gag ggt gaa aag ggt ctg ctc        960
Val Pro His Leu Asp Thr Arg Val Ile Glu Gly Glu Lys Gly Leu Leu
305                 310                 315                 320 ttt gga cct tac ggt ggc tgg acc cct aag ttc ttg aag gaa ggc tcc       1008
Phe Gly Pro Tyr Gly Gly Trp Thr Pro Lys Phe Leu Lys Glu Gly Ser
                325                 330                 335 tac ctg gac ctg ttc aag tcc atc cgc cca gac aac att cct tcc tac       1056
Tyr Leu Asp Leu Phe Lys Ser Ile Arg Pro Asp Asn Ile Pro Ser Tyr
            340                 345                 350 ctt ggc gtt gct gct cag gaa ttt gat ctg acc aag tac ctt gtc act       1104
Leu Gly Val Ala Ala Gln Glu Phe Asp Leu Thr Lys Tyr Leu Val Thr
            355                 360                 365 gaa gtt ctc aag gac cag gac aag cgt atg gat gct ctt cgc gag tac       1152
Glu Val Leu Lys Asp Gln Asp Lys Arg Met Asp Ala Leu Arg Glu Tyr
    370                 375                 380 atg cca gag gca caa aac ggc gat tgg gag acc atc gtt gcc gga cag       1200
Met Pro Glu Ala Gln Asn Gly Asp Trp Glu Thr Ile Val Ala Gly Gln
385                 390                 395                 400 cgt gtt cag gtt att aag cct gca gga ttc cct aag ttc ggt tcc ctg       1248
Arg Val Gln Val Ile Lys Pro Ala Gly Phe Pro Lys Phe Gly Ser Leu
                405                 410                 415 gaa ttc ggc acc acc ttg atc aac aac tcc gaa ggc acc atc gcc gga       1296
Glu Phe Gly Thr Thr Leu Ile Asn Asn Ser Glu Gly Thr Ile Ala Gly
            420                 425                 430 ttg ctc ggt gct tcc cct gga gca tcc atc gca cct tcc gca atg atc       1344
Leu Leu Gly Ala Ser Pro Gly Ala Ser Ile Ala Pro Ser Ala Met Ile
            435                 440                 445 gag ctg ctt gag cgt tgc ttc ggt gac cgc atg atc gag tgg ggc gac       1392
Glu Leu Leu Glu Arg Cys Phe Gly Asp Arg Met Ile Glu Trp Gly Asp
    450                 455                 460 aag ctg aag gac atg atc cct tcc tac ggc aag aag ctt gct tcc gag       1440
Lys Leu Lys Asp Met Ile Pro Ser Tyr Gly Lys Lys Leu Ala Ser Glu
465                 470                 475                 480
```

```
                              -continued cca gca ctg ttt gag cag cag tgg gca cgc acc cag aag acc ctg aag    1488
Pro Ala Leu Phe Glu Gln Gln Trp Ala Arg Thr Gln Lys Thr Leu Lys
                485                 490                 495 ctt gag gaa gcc taa                                                1503
Leu Glu Glu Ala
500
```

<210> SEQ ID NO 10
<211> LENGTH: 500
<212> TYPE: PRT
<213> ORGANISM: Corynebacterium glutamicum

<400> SEQUENCE: 10

```
Met Ser Asp Ser Pro Lys Asn Ala Pro Arg Ile Thr Asp Glu Ala Asp
1               5                   10                  15

Val Val Leu Ile Gly Ala Gly Ile Met Ser Ser Thr Leu Gly Ala Met
                20                  25                  30

Leu Arg Gln Leu Glu Pro Ser Trp Thr Gln Ile Val Phe Glu Arg Leu
            35                  40                  45

Asp Gly Pro Ala Gln Glu Ser Ser Pro Trp Asn Asn Ala Gly Thr
        50                  55                  60

Gly His Ser Ala Leu Cys Glu Leu Asn Tyr Thr Pro Glu Val Lys Gly
65                  70                  75                  80

Lys Val Glu Ile Ala Lys Ala Val Gly Ile Asn Glu Lys Phe Gln Val
                85                  90                  95

Ser Arg Gln Phe Trp Ser His Leu Val Glu Glu Gly Val Leu Ala Asp
            100                 105                 110

Pro Lys Glu Phe Ile Asn Pro Val Pro His Val Ser Phe Gly Gln Gly
        115                 120                 125

Ala Asp Gln Val Ala Tyr Ile Lys Ala Arg Tyr Glu Ala Leu Lys Asp
130                 135                 140

His Pro Leu Phe Gln Gly Met Thr Tyr Ala Asp Asp Glu Ala Thr Phe
145                 150                 155                 160

Thr Glu Lys Leu Pro Leu Met Ala Lys Gly Arg Asp Phe Ser Asp Pro
                165                 170                 175

Val Ala Ile Ser Trp Ile Asp Glu Gly Thr Asp Ile Asn Tyr Gly Ala
            180                 185                 190

Gln Thr Lys Gln Tyr Leu Asp Ala Ser Glu Val Glu Gly Thr Glu Ile
        195                 200                 205

Arg Tyr Gly His Glu Val Lys Ser Ile Lys Ala Asp Gly Ala Lys Trp
210                 215                 220

Ile Val Thr Val Lys Asn Val His Thr Gly Asp Thr Lys Thr Ile Lys
225                 230                 235                 240

Ala Asn Phe Val Phe Val Gly Ala Gly Gly Tyr Ala Leu Asp Leu Leu
                245                 250                 255

Arg Ser Ala Gly Ile Pro Gln Val Lys Gly Phe Ala Gly Phe Pro Val
            260                 265                 270

Ser Gly Leu Trp Leu Arg Cys Thr Asn Glu Glu Leu Ile Glu Gln His
        275                 280                 285

Ala Ala Lys Val Tyr Gly Lys Ala Ser Val Gly Ala Pro Pro Met Ser
290                 295                 300

Val Pro His Leu Asp Thr Arg Val Ile Glu Glu Lys Gly Leu Leu
305                 310                 315                 320

Phe Gly Pro Tyr Gly Gly Trp Thr Pro Lys Phe Leu Lys Glu Gly Ser
                325                 330                 335
```

```
Tyr Leu Asp Leu Phe Lys Ser Ile Arg Pro Asp Asn Ile Pro Ser Tyr
            340                 345                 350

Leu Gly Val Ala Ala Gln Glu Phe Asp Leu Thr Lys Tyr Leu Val Thr
            355                 360                 365

Glu Val Leu Lys Asp Gln Asp Lys Arg Met Asp Ala Leu Arg Glu Tyr
        370                 375                 380

Met Pro Glu Ala Gln Asn Gly Asp Trp Glu Thr Ile Val Ala Gly Gln
385                 390                 395                 400

Arg Val Gln Val Ile Lys Pro Ala Gly Phe Pro Lys Phe Gly Ser Leu
                405                 410                 415

Glu Phe Gly Thr Thr Leu Ile Asn Asn Ser Glu Gly Thr Ile Ala Gly
            420                 425                 430

Leu Leu Gly Ala Ser Pro Gly Ala Ser Ile Ala Pro Ser Ala Met Ile
            435                 440                 445

Glu Leu Leu Glu Arg Cys Phe Gly Asp Arg Met Ile Glu Trp Gly Asp
        450                 455                 460

Lys Leu Lys Asp Met Ile Pro Ser Tyr Gly Lys Lys Leu Ala Ser Glu
465                 470                 475                 480

Pro Ala Leu Phe Glu Gln Gln Trp Ala Arg Thr Gln Lys Thr Leu Lys
                485                 490                 495

Leu Glu Glu Ala
            500

<210> SEQ ID NO 11
<211> LENGTH: 20
<212> TYPE: DNA
<213> ORGANISM: artificial sequence
<220> FEATURE:
<223> OTHER INFORMATION: primer mqo-start

<400> SEQUENCE: 11
cagagaactc gcggagataa                                              20

<210> SEQ ID NO 12
<211> LENGTH: 20
<212> TYPE: DNA
<213> ORGANISM: artificial sequence
<220> FEATURE:
<223> OTHER INFORMATION: primer mqo-stop

<400> SEQUENCE: 12
aacctcaaca gacatgtgcg                                              20

<210> SEQ ID NO 13
<211> LENGTH: 20
<212> TYPE: DNA
<213> ORGANISM: artificial sequence
<220> FEATURE:
<223> OTHER INFORMATION: primer mqo-A1

<400> SEQUENCE: 13
ggtgaaactt ccgcgatact                                              20

<210> SEQ ID NO 14
<211> LENGTH: 20
<212> TYPE: DNA
<213> ORGANISM: artificial sequence
<220> FEATURE:
<223> OTHER INFORMATION: primer mqo-E1

<400> SEQUENCE: 14
```

-continued

```
gtgtcgccta aatcacactg                                              20
```

<210> SEQ ID NO 15
<211> LENGTH: 99
<212> TYPE: DNA
<213> ORGANISM: Corynebacterium glutamicum
<220> FEATURE:
<221> NAME/KEY: CDS
<222> LOCATION: (1)..(99)
<223> OTHER INFORMATION: reading frame
<220> FEATURE:
<221> NAME/KEY: mutation
<222> LOCATION: (49)..(51)
<223> OTHER INFORMATION: position 49 to 51 corresponds to position 331
      to 333 in SEQ ID
      NO:1, SEQ ID NO:5, SEQ ID NO:7 or SEQ ID NO:9
<220> FEATURE:
<221> NAME/KEY: misc_feature
<222> LOCATION: (49)..(51)
<223> OTHER INFORMATION: n is a, c, g, or t

<400> SEQUENCE: 15

```
cag gtt tcc cgt cag ttc tgg tct cac ctc gtt gaa gag gga gtg ctg    48
Gln Val Ser Arg Gln Phe Trp Ser His Leu Val Glu Glu Gly Val Leu
1               5                   10                  15 nnn gat cct aag gaa ttc atc aac cct gtt cct cac gta tct ttc ggc    96
Xaa Asp Pro Lys Glu Phe Ile Asn Pro Val Pro His Val Ser Phe Gly
            20                  25                  30 cag                                                                99
Gln
```

<210> SEQ ID NO 16
<211> LENGTH: 33
<212> TYPE: PRT
<213> ORGANISM: Corynebacterium glutamicum
<220> FEATURE:
<221> NAME/KEY: misc_feature
<222> LOCATION: (17)..(17)
<223> OTHER INFORMATION: The 'Xaa' at location 17 stands for Lys, Asn,
      Arg, Thr, Ile,
      Met, Glu, Asp, Gly, Ala, Val, Gln, His, Pro, Leu, Tyr, Trp, Cys,
      or Phe.

<400> SEQUENCE: 16

```
Gln Val Ser Arg Gln Phe Trp Ser His Leu Val Glu Glu Gly Val Leu
1               5                   10                  15

Xaa Asp Pro Lys Glu Phe Ile Asn Pro Val Pro His Val Ser Phe Gly
            20                  25                  30

Gln
```

<210> SEQ ID NO 17
<211> LENGTH: 99
<212> TYPE: DNA
<213> ORGANISM: Corynebacterium glutamicum
<220> FEATURE:
<221> NAME/KEY: CDS
<222> LOCATION: (1)..(99)
<223> OTHER INFORMATION: reading frame
<220> FEATURE:
<221> NAME/KEY: mutation
<222> LOCATION: (49)..(51)
<223> OTHER INFORMATION: position 49 to 51 corresponds to position 331
      to 333 in SEQ ID NO:5

<400> SEQUENCE: 17

```
cag gtt tcc cgt cag ttc tgg tct cac ctc gtt gaa gag gga gtg ctg    48
Gln Val Ser Arg Gln Phe Trp Ser His Leu Val Glu Glu Gly Val Leu
1               5                   10                  15
```

```
ttt gat cct aag gaa ttc atc aac cct gtt cct cac gta tct ttc ggc      96
Phe Asp Pro Lys Glu Phe Ile Asn Pro Val Pro His Val Ser Phe Gly
        20                  25                  30 cag                                                                   99
Gln

<210> SEQ ID NO 18
<211> LENGTH: 33
<212> TYPE: PRT
<213> ORGANISM: Corynebacterium glutamicum

<400> SEQUENCE: 18

Gln Val Ser Arg Gln Phe Trp Ser His Leu Val Glu Glu Gly Val Leu
1               5                   10                  15

Phe Asp Pro Lys Glu Phe Ile Asn Pro Val Pro His Val Ser Phe Gly
        20                  25                  30

Gln

<210> SEQ ID NO 19
<211> LENGTH: 99
<212> TYPE: DNA
<213> ORGANISM: Corynebacterium glutamicum
<220> FEATURE:
<221> NAME/KEY: CDS
<222> LOCATION: (1)..(99)
<223> OTHER INFORMATION: reading frame
<220> FEATURE:
<221> NAME/KEY: mutation
<222> LOCATION: (49)..(51)
<223> OTHER INFORMATION: position 49 to 51 corresponds to position 331
      to 333 von SEQ ID NO:7 or SEQ ID NO:9

<400> SEQUENCE: 19 cag gtt tcc cgt cag ttc tgg tct cac ctc gtt gaa gag gga gtg ctg      48
Gln Val Ser Arg Gln Phe Trp Ser His Leu Val Glu Glu Gly Val Leu
1               5                   10                  15 gct gat cct aag gaa ttc atc aac cct gtt cct cac gta tct ttc ggc      96
Ala Asp Pro Lys Glu Phe Ile Asn Pro Val Pro His Val Ser Phe Gly
        20                  25                  30 cag                                                                   99
Gln

<210> SEQ ID NO 20
<211> LENGTH: 33
<212> TYPE: PRT
<213> ORGANISM: Corynebacterium glutamicum

<400> SEQUENCE: 20

Gln Val Ser Arg Gln Phe Trp Ser His Leu Val Glu Glu Gly Val Leu
1               5                   10                  15

Ala Asp Pro Lys Glu Phe Ile Asn Pro Val Pro His Val Ser Phe Gly
        20                  25                  30

Gln

<210> SEQ ID NO 21
<211> LENGTH: 1263
<212> TYPE: DNA
<213> ORGANISM: Corynebacterium glutamicum
<220> FEATURE:
<221> NAME/KEY: CDS
<222> LOCATION: (1)..(1263)
<223> OTHER INFORMATION: lysC wild-type gene

<400> SEQUENCE: 21
```

-continued

| | |
|---|---|
| gtg gcc ctg gtc gta cag aaa tat ggc ggt tcc tcg ctt gag agt gcg<br>Met Ala Leu Val Val Gln Lys Tyr Gly Gly Ser Ser Leu Glu Ser Ala<br>1               5                   10                  15 | 48 |
| gaa cgc att aga aac gtc gct gaa cgg atc gtt gcc acc aag aag gct<br>Glu Arg Ile Arg Asn Val Ala Glu Arg Ile Val Ala Thr Lys Lys Ala<br>            20                  25                  30 | 96 |
| gga aat gat gtc gtg gtt gtc tgc tcc gca atg gga gac acc acg gat<br>Gly Asn Asp Val Val Val Val Cys Ser Ala Met Gly Asp Thr Thr Asp<br>        35                  40                  45 | 144 |
| gaa ctt cta gaa ctt gca gcg gca gtg aat ccc gtt ccg cca gct cgt<br>Glu Leu Leu Glu Leu Ala Ala Ala Val Asn Pro Val Pro Pro Ala Arg<br>50                  55                  60 | 192 |
| gaa atg gat atg ctc ctg act gct ggt gag cgt att tct aac gct ctc<br>Glu Met Asp Met Leu Leu Thr Ala Gly Glu Arg Ile Ser Asn Ala Leu<br>65                  70                  75                  80 | 240 |
| gtc gcc atg gct att gag tcc ctt ggc gca gaa gcc caa tct ttc acg<br>Val Ala Met Ala Ile Glu Ser Leu Gly Ala Glu Ala Gln Ser Phe Thr<br>            85                  90                  95 | 288 |
| ggc tct cag gct ggt gtg ctc acc acc gag cgc cac gga aac gca cgc<br>Gly Ser Gln Ala Gly Val Leu Thr Thr Glu Arg His Gly Asn Ala Arg<br>        100                 105                 110 | 336 |
| att gtt gat gtc act cca ggt cgt gtg cgt gaa gca ctc gat gag ggc<br>Ile Val Asp Val Thr Pro Gly Arg Val Arg Glu Ala Leu Asp Glu Gly<br>    115                 120                 125 | 384 |
| aag atc tgc att gtt gct ggt ttc cag ggt gtt aat aaa gaa acc cgc<br>Lys Ile Cys Ile Val Ala Gly Phe Gln Gly Val Asn Lys Glu Thr Arg<br>130                 135                 140 | 432 |
| gat gtc acc acg ttg ggt cgt ggt ggt tct gac acc act gca gtt gcg<br>Asp Val Thr Thr Leu Gly Arg Gly Gly Ser Asp Thr Thr Ala Val Ala<br>145                 150                 155                 160 | 480 |
| ttg gca gct gct ttg aac gct gat gtg tgt gag att tac tcg gac gtt<br>Leu Ala Ala Ala Leu Asn Ala Asp Val Cys Glu Ile Tyr Ser Asp Val<br>            165                 170                 175 | 528 |
| gac ggt gtg tat acc gct gac ccg cgc atc gtt cct aat gca cag aag<br>Asp Gly Val Tyr Thr Ala Asp Pro Arg Ile Val Pro Asn Ala Gln Lys<br>        180                 185                 190 | 576 |
| ctg gaa aag ctc agc ttc gaa gaa atg ctg gaa ctt gct gct gtt ggc<br>Leu Glu Lys Leu Ser Phe Glu Glu Met Leu Glu Leu Ala Ala Val Gly<br>    195                 200                 205 | 624 |
| tcc aag att ttg gtg ctg cgc agt gtt gaa tac gct cgt gca ttc aat<br>Ser Lys Ile Leu Val Leu Arg Ser Val Glu Tyr Ala Arg Ala Phe Asn<br>210                 215                 220 | 672 |
| gtg cca ctt cgc gta cgc tcg tct tat agt aat gat ccc ggc act ttg<br>Val Pro Leu Arg Val Arg Ser Ser Tyr Ser Asn Asp Pro Gly Thr Leu<br>225                 230                 235                 240 | 720 |
| att gcc ggc tct atg gag gat att cct gtg gaa gaa gca gtc ctt acc<br>Ile Ala Gly Ser Met Glu Asp Ile Pro Val Glu Glu Ala Val Leu Thr<br>            245                 250                 255 | 768 |
| ggt gtc gca acc gac aag tcc gaa gcc aaa gta acc gtt ctg ggt att<br>Gly Val Ala Thr Asp Lys Ser Glu Ala Lys Val Thr Val Leu Gly Ile<br>        260                 265                 270 | 816 |
| tcc gat aag cca ggc gag gct gcg aag gtt ttc cgt gcg ttg gct gat<br>Ser Asp Lys Pro Gly Glu Ala Ala Lys Val Phe Arg Ala Leu Ala Asp<br>    275                 280                 285 | 864 |
| gca gaa atc aac att gac atg gtt ctg cag aac gtc tct tct gta gaa<br>Ala Glu Ile Asn Ile Asp Met Val Leu Gln Asn Val Ser Ser Val Glu<br>290                 295                 300 | 912 |
| gac ggc acc acc gac atc acc ttc acc tgc cct cgt tcc gac ggc cgc<br>Asp Gly Thr Thr Asp Ile Thr Phe Thr Cys Pro Arg Ser Asp Gly Arg<br>305                 310                 315                 320 | 960 |

-continued

```
cgc gcg atg gag atc ttg aag aag ctt cag gtt cag ggc aac tgg acc      1008
Arg Ala Met Glu Ile Leu Lys Lys Leu Gln Val Gln Gly Asn Trp Thr
            325                 330                 335 aat gtg ctt tac gac gac cag gtc ggc aaa gtc tcc ctc gtg ggt gct      1056
Asn Val Leu Tyr Asp Asp Gln Val Gly Lys Val Ser Leu Val Gly Ala
        340                 345                 350 ggc atg aag tct cac cca ggt gtt acc gca gag ttc atg gaa gct ctg      1104
Gly Met Lys Ser His Pro Gly Val Thr Ala Glu Phe Met Glu Ala Leu
    355                 360                 365 cgc gat gtc aac gtg aac atc gaa ttg att tcc acc tct gag att cgt      1152
Arg Asp Val Asn Val Asn Ile Glu Leu Ile Ser Thr Ser Glu Ile Arg
370                 375                 380 att tcc gtg ctg atc cgt gaa gat gat ctg gat gct gct gca cgt gca      1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat      1248
Leu His Glu Gln Phe Gln Leu Gly Gly Glu Asp Glu Ala Val Val Tyr
                405                 410                 415 gca ggc acc gga cgc                                                  1263
Ala Gly Thr Gly Arg
            420

<210> SEQ ID NO 22
<211> LENGTH: 421
<212> TYPE: PRT
<213> ORGANISM: Corynebacterium glutamicum

<400> SEQUENCE: 22

Met Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220
```

-continued

```
Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Ala Val Leu Thr
            245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
        290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
        370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420
```

```
<210> SEQ ID NO 23
<211> LENGTH: 1503
<212> TYPE: DNA
<213> ORGANISM: Corynebacterium glutamicum
<220> FEATURE:
<221> NAME/KEY: CDS
<222> LOCATION: (1)..(1500)
<223> OTHER INFORMATION: mqo allele
<220> FEATURE:
<221> NAME/KEY: mutation
<222> LOCATION: (1168)..(1170)
<220> FEATURE:
<221> NAME/KEY: misc_feature
<222> LOCATION: (1168)..(1170)
<223> OTHER INFORMATION: n is a, c, g, or t

<400> SEQUENCE: 23 atg tca gat tcc ccg aag aac gca ccg agg att acc gat gag gca gat    48
Met Ser Asp Ser Pro Lys Asn Ala Pro Arg Ile Thr Asp Glu Ala Asp
1               5                   10                  15 gta gtt ctc att ggt gcc ggt atc atg agc tcc acg ctg ggt gca atg    96
Val Val Leu Ile Gly Ala Gly Ile Met Ser Ser Thr Leu Gly Ala Met
                20                  25                  30 ctg cgt cag ctg gag cca agc tgg act cag atc gtc ttc gag cgt ttg   144
Leu Arg Gln Leu Glu Pro Ser Trp Thr Gln Ile Val Phe Glu Arg Leu
            35                  40                  45 gat gga ccg gca caa gag tcg tcc tcc ccg tgg aac aat gca gga acc   192
Asp Gly Pro Ala Gln Glu Ser Ser Ser Pro Trp Asn Asn Ala Gly Thr
        50                  55                  60 ggc cac tct gct cta tgc gag ctg aac tac acc cca gag gtt aag ggc   240
Gly His Ser Ala Leu Cys Glu Leu Asn Tyr Thr Pro Glu Val Lys Gly
65                  70                  75                  80 aag gtt gaa att gcc aag gct gta gga atc aac gag aag ttc cag gtt   288
```

```
Lys Val Glu Ile Ala Lys Ala Val Gly Ile Asn Glu Lys Phe Gln Val
                85                  90                  95 tcc cgt cag ttc tgg tct cac ctc gtt gaa gag gga gtg ctg tct gat      336
Ser Arg Gln Phe Trp Ser His Leu Val Glu Glu Gly Val Leu Ser Asp
            100                 105                 110 cct aag gaa ttc atc aac cct gtt cct cac gta tct ttc ggc cag ggc      384
Pro Lys Glu Phe Ile Asn Pro Val Pro His Val Ser Phe Gly Gln Gly
            115                 120                 125 gca gat cag gtt gca tac atc aag gct cgc tac gaa gct ttg aag gat      432
Ala Asp Gln Val Ala Tyr Ile Lys Ala Arg Tyr Glu Ala Leu Lys Asp
        130                 135                 140 cac cca ctc ttc cag ggc atg acc tac gct gac gat gaa gct acc ttc      480
His Pro Leu Phe Gln Gly Met Thr Tyr Ala Asp Asp Glu Ala Thr Phe
145                 150                 155                 160 acc gag aag ctg cct ttg atg gca aag ggc cgt gac ttc tct gat cca      528
Thr Glu Lys Leu Pro Leu Met Ala Lys Gly Arg Asp Phe Ser Asp Pro
                165                 170                 175 gta gca atc tct tgg atc gat gaa ggc acc gac atc aac tac ggt gct      576
Val Ala Ile Ser Trp Ile Asp Glu Gly Thr Asp Ile Asn Tyr Gly Ala
            180                 185                 190 cag acc aag cag tac ctg gat gca gct gaa gtt gaa ggc act gaa atc      624
Gln Thr Lys Gln Tyr Leu Asp Ala Ala Glu Val Glu Gly Thr Glu Ile
            195                 200                 205 cgc tat ggc cac gaa gtc aag agc atc aag gct gat ggc gca aag tgg      672
Arg Tyr Gly His Glu Val Lys Ser Ile Lys Ala Asp Gly Ala Lys Trp
        210                 215                 220 atc gtg acc gtc aag aac gta cac act ggc gac acc aag acc atc aag      720
Ile Val Thr Val Lys Asn Val His Thr Gly Asp Thr Lys Thr Ile Lys
225                 230                 235                 240 gca aac ttc gtg ttc gtc ggc gca ggc gga tac gca ctg gat ctg ctt      768
Ala Asn Phe Val Phe Val Gly Ala Gly Gly Tyr Ala Leu Asp Leu Leu
                245                 250                 255 cgc agc gca ggc atc cca cag gtc aag ggc ttc gct gga ttc cca gta      816
Arg Ser Ala Gly Ile Pro Gln Val Lys Gly Phe Ala Gly Phe Pro Val
            260                 265                 270 tcc ggc ctg tgg ctt cgt tgc acc aac gag gaa ctg atc gag cag cac      864
Ser Gly Leu Trp Leu Arg Cys Thr Asn Glu Glu Leu Ile Glu Gln His
        275                 280                 285 gca gcc aag gta tat ggc aag gca tct gtt ggc gct cct cca atg tct      912
Ala Ala Lys Val Tyr Gly Lys Ala Ser Val Gly Ala Pro Pro Met Ser
        290                 295                 300 gtt cct cac ctt gac acc cgc gtt atc gag ggt gaa aag ggt ctg ctc      960
Val Pro His Leu Asp Thr Arg Val Ile Glu Gly Glu Lys Gly Leu Leu
305                 310                 315                 320 ttt gga cct tac ggt ggc tgg acc cct aag ttc ttg aag gaa ggc tcc     1008
Phe Gly Pro Tyr Gly Gly Trp Thr Pro Lys Phe Leu Lys Glu Gly Ser
                325                 330                 335 tac ctg gac ctg ttc aag tcc atc cgc cca gac aac att cct tcc tac     1056
Tyr Leu Asp Leu Phe Lys Ser Ile Arg Pro Asp Asn Ile Pro Ser Tyr
            340                 345                 350 ctt ggc gtt gct gct cag gaa ttt gat ctg acc aag tac ctt gtc act     1104
Leu Gly Val Ala Ala Gln Glu Phe Asp Leu Thr Lys Tyr Leu Val Thr
        355                 360                 365 gaa gtt ctc aag gac cag gac aag cgt atg gat gct ctt cgc gag tac     1152
Glu Val Leu Lys Asp Gln Asp Lys Arg Met Asp Ala Leu Arg Glu Tyr
370                 375                 380 atg cca gag gca caa nnn ggc gat tgg gag acc atc gtt gcc gga cag     1200
Met Pro Glu Ala Gln Xaa Gly Asp Trp Glu Thr Ile Val Ala Gly Gln
                385                 390                 395                 400
```

-continued

```
cgt gtt cag gtt att aag cct gca gga ttc cct aag ttc ggt tcc ctg    1248
Arg Val Gln Val Ile Lys Pro Ala Gly Phe Pro Lys Phe Gly Ser Leu
            405                 410                 415 gaa ttc ggc acc acc ttg atc aac aac tcc gaa ggc acc atc gcc gga    1296
Glu Phe Gly Thr Thr Leu Ile Asn Asn Ser Glu Gly Thr Ile Ala Gly
        420                 425                 430 ttg ctc ggt gct tcc cct gga gca tcc atc gca cct tcc gca atg atc    1344
Leu Leu Gly Ala Ser Pro Gly Ala Ser Ile Ala Pro Ser Ala Met Ile
    435                 440                 445 gag ctg ctt gag cgt tgc ttc ggt gac cgc atg atc gag tgg ggc gac    1392
Glu Leu Leu Glu Arg Cys Phe Gly Asp Arg Met Ile Glu Trp Gly Asp
450                 455                 460 aag ctg aag gac atg atc cct tcc tac ggc aag aag ctt gct tcc gag    1440
Lys Leu Lys Asp Met Ile Pro Ser Tyr Gly Lys Lys Leu Ala Ser Glu
465                 470                 475                 480 cca gca ctg ttt gag cag cag tgg gca cgc acc cag aag acc ctg aag    1488
Pro Ala Leu Phe Glu Gln Gln Trp Ala Arg Thr Gln Lys Thr Leu Lys
                485                 490                 495 ctt gag gaa gcc taa                                                1503
Leu Glu Glu Ala
        500
```

<210> SEQ ID NO 24
<211> LENGTH: 500
<212> TYPE: PRT
<213> ORGANISM: Corynebacterium glutamicum
<220> FEATURE:
<221> NAME/KEY: misc_feature
<222> LOCATION: (390)..(390)
<223> OTHER INFORMATION: The 'Xaa' at location 390 stands for Lys, Arg, Ser, Thr,
      Ile, Met, Glu, Asp, Gly, Ala, Val, Gln, His, Pro, Leu, Tyr, Trp,
      Cys, or Phe.

<400> SEQUENCE: 24

```
Met Ser Asp Ser Pro Lys Asn Ala Pro Arg Ile Thr Asp Glu Ala Asp
1               5                   10                  15

Val Val Leu Ile Gly Ala Gly Ile Met Ser Ser Thr Leu Gly Ala Met
            20                  25                  30

Leu Arg Gln Leu Glu Pro Ser Trp Thr Gln Ile Val Phe Glu Arg Leu
        35                  40                  45

Asp Gly Pro Ala Gln Glu Ser Ser Pro Trp Asn Asn Ala Gly Thr
    50                  55                  60

Gly His Ser Ala Leu Cys Glu Leu Asn Tyr Thr Pro Glu Val Lys Gly
65                  70                  75                  80

Lys Val Glu Ile Ala Lys Ala Val Gly Ile Asn Glu Lys Phe Gln Val
                85                  90                  95

Ser Arg Gln Phe Trp Ser His Leu Val Glu Glu Gly Val Leu Ser Asp
            100                 105                 110

Pro Lys Glu Phe Ile Asn Pro Val Pro His Val Ser Phe Gly Gln Gly
        115                 120                 125

Ala Asp Gln Val Ala Tyr Ile Lys Ala Arg Tyr Glu Ala Leu Lys Asp
    130                 135                 140

His Pro Leu Phe Gln Gly Met Thr Tyr Ala Asp Asp Glu Ala Thr Phe
145                 150                 155                 160

Thr Glu Lys Leu Pro Leu Met Ala Lys Gly Arg Asp Phe Ser Asp Pro
                165                 170                 175

Val Ala Ile Ser Trp Ile Asp Glu Gly Thr Asp Ile Asn Tyr Gly Ala
            180                 185                 190
```

-continued

```
Gln Thr Lys Gln Tyr Leu Asp Ala Ala Glu Val Glu Gly Thr Glu Ile
            195                 200                 205
Arg Tyr Gly His Glu Val Lys Ser Ile Lys Ala Asp Gly Ala Lys Trp
        210                 215                 220
Ile Val Thr Val Lys Asn Val His Thr Gly Asp Thr Lys Thr Ile Lys
225                 230                 235                 240
Ala Asn Phe Val Phe Val Gly Ala Gly Tyr Ala Leu Asp Leu Leu
            245                 250                 255
Arg Ser Ala Gly Ile Pro Gln Val Lys Gly Phe Ala Gly Phe Pro Val
            260                 265                 270
Ser Gly Leu Trp Leu Arg Cys Thr Asn Glu Glu Leu Ile Glu Gln His
        275                 280                 285
Ala Ala Lys Val Tyr Gly Lys Ala Ser Val Gly Ala Pro Pro Met Ser
    290                 295                 300
Val Pro His Leu Asp Thr Arg Val Ile Glu Gly Lys Gly Leu Leu
305                 310                 315                 320
Phe Gly Pro Tyr Gly Gly Trp Thr Pro Lys Phe Leu Lys Glu Gly Ser
            325                 330                 335
Tyr Leu Asp Leu Phe Lys Ser Ile Arg Pro Asp Asn Ile Pro Ser Tyr
            340                 345                 350
Leu Gly Val Ala Ala Gln Glu Phe Asp Leu Thr Lys Tyr Leu Val Thr
        355                 360                 365
Glu Val Leu Lys Asp Gln Asp Lys Arg Met Asp Ala Leu Arg Glu Tyr
    370                 375                 380
Met Pro Glu Ala Gln Xaa Gly Asp Trp Glu Thr Ile Val Ala Gly Gln
385                 390                 395                 400
Arg Val Gln Val Ile Lys Pro Ala Gly Phe Pro Lys Phe Gly Ser Leu
            405                 410                 415
Glu Phe Gly Thr Thr Leu Ile Asn Asn Ser Glu Gly Thr Ile Ala Gly
        420                 425                 430
Leu Leu Gly Ala Ser Pro Gly Ala Ser Ile Ala Pro Ser Ala Met Ile
    435                 440                 445
Glu Leu Leu Glu Arg Cys Phe Gly Asp Arg Met Ile Glu Trp Gly Asp
        450                 455                 460
Lys Leu Lys Asp Met Ile Pro Ser Tyr Gly Lys Lys Leu Ala Ser Glu
465                 470                 475                 480
Pro Ala Leu Phe Glu Gln Gln Trp Ala Arg Thr Gln Lys Thr Leu Lys
            485                 490                 495
Leu Glu Glu Ala
        500
```

<210> SEQ ID NO 25
<211> LENGTH: 1503
<212> TYPE: DNA
<213> ORGANISM: Corynebacterium glutamicum
<220> FEATURE:
<221> NAME/KEY: CDS
<222> LOCATION: (1)..(1500)
<223> OTHER INFORMATION: mqo allele
<220> FEATURE:
<221> NAME/KEY: mutation
<222> LOCATION: (1168)..(1170)

<400> SEQUENCE: 25

```
atg tca gat tcc ccg aag aac gca ccg agg att acc gat gag gca gat     48
Met Ser Asp Ser Pro Lys Asn Ala Pro Arg Ile Thr Asp Glu Ala Asp
1               5                   10                  15
```

```
gta gtt ctc att ggt gcc ggt atc atg agc tcc acg ctg ggt gca atg     96
Val Val Leu Ile Gly Ala Gly Ile Met Ser Ser Thr Leu Gly Ala Met
         20                  25                  30 ctg cgt cag ctg gag cca agc tgg act cag atc gtc ttc gag cgt ttg    144
Leu Arg Gln Leu Glu Pro Ser Trp Thr Gln Ile Val Phe Glu Arg Leu
     35                  40                  45 gat gga ccg gca caa gag tcg tcc tcc ccg tgg aac aat gca gga acc    192
Asp Gly Pro Ala Gln Glu Ser Ser Ser Pro Trp Asn Asn Ala Gly Thr
 50                  55                  60 ggc cac tct gct cta tgc gag ctg aac tac acc cca gag gtt aag ggc    240
Gly His Ser Ala Leu Cys Glu Leu Asn Tyr Thr Pro Glu Val Lys Gly
 65                  70                  75                  80 aag gtt gaa att gcc aag gct gta gga atc aac gag aag ttc cag gtt    288
Lys Val Glu Ile Ala Lys Ala Val Gly Ile Asn Glu Lys Phe Gln Val
                 85                  90                  95 tcc cgt cag ttc tgg tct cac ctc gtt gaa gag gga gtg ctg tct gat    336
Ser Arg Gln Phe Trp Ser His Leu Val Glu Glu Gly Val Leu Ser Asp
             100                 105                 110 cct aag gaa ttc atc aac cct gtt cct cac gta tct ttc ggc cag ggc    384
Pro Lys Glu Phe Ile Asn Pro Val Pro His Val Ser Phe Gly Gln Gly
         115                 120                 125 gca gat cag gtt gca tac atc aag gct cgc tac gaa gct ttg aag gat    432
Ala Asp Gln Val Ala Tyr Ile Lys Ala Arg Tyr Glu Ala Leu Lys Asp
130                 135                 140 cac ccc ctc ttc cag ggc atg acc tac gct gac gat gaa gct acc ttc    480
His Pro Leu Phe Gln Gly Met Thr Tyr Ala Asp Asp Glu Ala Thr Phe
145                 150                 155                 160 acc gag aag ctg cct ttg atg gca aag ggc cgt gac ttc tct gat cca    528
Thr Glu Lys Leu Pro Leu Met Ala Lys Gly Arg Asp Phe Ser Asp Pro
                 165                 170                 175 gta gca atc tct tgg atc gat gaa ggc acc gac atc aac tac ggt gct    576
Val Ala Ile Ser Trp Ile Asp Glu Gly Thr Asp Ile Asn Tyr Gly Ala
             180                 185                 190 cag acc aag cag tac ctg gat gca gct gaa gtt gaa ggc act gaa atc    624
Gln Thr Lys Gln Tyr Leu Asp Ala Ala Glu Val Glu Gly Thr Glu Ile
         195                 200                 205 cgc tat ggc cac gaa gtc aag agc atc aag gct gat ggc gca aag tgg    672
Arg Tyr Gly His Glu Val Lys Ser Ile Lys Ala Asp Gly Ala Lys Trp
210                 215                 220 atc gtg acc gtc aag aac gta cac act ggc gac acc aag acc atc aag    720
Ile Val Thr Val Lys Asn Val His Thr Gly Asp Thr Lys Thr Ile Lys
225                 230                 235                 240 gca aac ttc gtg ttc gtc ggc gca ggc gga tac gca ctg gat ctg ctt    768
Ala Asn Phe Val Phe Val Gly Ala Gly Gly Tyr Ala Leu Asp Leu Leu
                 245                 250                 255 cgc agc gca ggc atc cca cag gtc aag ggc ttc gct gga ttc cca gta    816
Arg Ser Ala Gly Ile Pro Gln Val Lys Gly Phe Ala Gly Phe Pro Val
             260                 265                 270 tcc ggc ctg tgg ctt cgt tgc acc aac gag gaa ctg atc gag cag cac    864
Ser Gly Leu Trp Leu Arg Cys Thr Asn Glu Glu Leu Ile Glu Gln His
         275                 280                 285 gca gcc aag gta tat ggc aag gca tct gtt ggc gct cct cca atg tct    912
Ala Ala Lys Val Tyr Gly Lys Ala Ser Val Gly Ala Pro Pro Met Ser
290                 295                 300 gtt cct cac ctt gac acc cgc gtt atc gag ggt gaa aag ggt ctg ctc    960
Val Pro His Leu Asp Thr Arg Val Ile Glu Gly Glu Lys Gly Leu Leu
305                 310                 315                 320 ttt gga cct tac ggt ggc tgg acc cct aag ttc ttg aag gaa ggc tcc   1008
Phe Gly Pro Tyr Gly Gly Trp Thr Pro Lys Phe Leu Lys Glu Gly Ser
                 325                 330                 335
```

-continued

```
tac ctg gac ctg ttc aag tcc atc cgc cca gac aac att cct tcc tac      1056
Tyr Leu Asp Leu Phe Lys Ser Ile Arg Pro Asp Asn Ile Pro Ser Tyr
        340                 345                 350 ctt ggc gtt gct gct cag gaa ttt gat ctg acc aag tac ctt gtc act      1104
Leu Gly Val Ala Ala Gln Glu Phe Asp Leu Thr Lys Tyr Leu Val Thr
            355                 360                 365 gaa gtt ctc aag gac cag gac aag cgt atg gat gct ctt cgc gag tac      1152
Glu Val Leu Lys Asp Gln Asp Lys Arg Met Asp Ala Leu Arg Glu Tyr
370                 375                 380 atg cca gag gca caa tac ggc gat tgg gag acc atc gtt gcc gga cag      1200
Met Pro Glu Ala Gln Tyr Gly Asp Trp Glu Thr Ile Val Ala Gly Gln
385                 390                 395                 400 cgt gtt cag gtt att aag cct gca gga ttc cct aag ttc ggt tcc ctg      1248
Arg Val Gln Val Ile Lys Pro Ala Gly Phe Pro Lys Phe Gly Ser Leu
                405                 410                 415 gaa ttc ggc acc acc ttg atc aac aac tcc gaa ggc acc atc gcc gga      1296
Glu Phe Gly Thr Thr Leu Ile Asn Asn Ser Glu Gly Thr Ile Ala Gly
            420                 425                 430 ttg ctc ggt gct tcc cct gga gca tcc atc gca cct tcc gca atg atc      1344
Leu Leu Gly Ala Ser Pro Gly Ala Ser Ile Ala Pro Ser Ala Met Ile
        435                 440                 445 gag ctg ctt gag cgt tgc ttc ggt gac cgc atg atc gag tgg ggc gac      1392
Glu Leu Leu Glu Arg Cys Phe Gly Asp Arg Met Ile Glu Trp Gly Asp
    450                 455                 460 aag ctg aag gac atg atc cct tcc tac ggc aag aag ctt gct tcc gag      1440
Lys Leu Lys Asp Met Ile Pro Ser Tyr Gly Lys Lys Leu Ala Ser Glu
465                 470                 475                 480 cca gca ctg ttt gag cag cag tgg gca cgc acc cag aag acc ctg aag      1488
Pro Ala Leu Phe Glu Gln Gln Trp Ala Arg Thr Gln Lys Thr Leu Lys
                485                 490                 495 ctt gag gaa gcc taa                                                  1503
Leu Glu Glu Ala
            500
```

<210> SEQ ID NO 26
<211> LENGTH: 500
<212> TYPE: PRT
<213> ORGANISM: Corynebacterium glutamicum

<400> SEQUENCE: 26

```
Met Ser Asp Ser Pro Lys Asn Ala Pro Arg Ile Thr Asp Glu Ala Asp
1               5                   10                  15

Val Val Leu Ile Gly Ala Gly Ile Met Ser Ser Thr Leu Gly Ala Met
            20                  25                  30

Leu Arg Gln Leu Glu Pro Ser Trp Thr Gln Ile Val Phe Glu Arg Leu
        35                  40                  45

Asp Gly Pro Ala Gln Glu Ser Ser Pro Trp Asn Asn Ala Gly Thr
    50                  55                  60

Gly His Ser Ala Leu Cys Glu Leu Asn Tyr Thr Pro Glu Val Lys Gly
65                  70                  75                  80

Lys Val Glu Ile Ala Lys Ala Val Gly Ile Asn Glu Lys Phe Gln Val
            85                  90                  95

Ser Arg Gln Phe Trp Ser His Leu Val Glu Glu Gly Val Leu Ser Asp
        100                 105                 110

Pro Lys Glu Phe Ile Asn Pro Val Pro His Val Ser Phe Gly Gln Gly
    115                 120                 125

Ala Asp Gln Val Ala Tyr Ile Lys Ala Arg Tyr Glu Ala Leu Lys Asp
130                 135                 140
```

```
His Pro Leu Phe Gln Gly Met Thr Tyr Ala Asp Asp Glu Ala Thr Phe
145                 150                 155                 160

Thr Glu Lys Leu Pro Leu Met Ala Lys Gly Arg Asp Phe Ser Asp Pro
                165                 170                 175

Val Ala Ile Ser Trp Ile Asp Glu Gly Thr Asp Ile Asn Tyr Gly Ala
            180                 185                 190

Gln Thr Lys Gln Tyr Leu Asp Ala Ala Glu Val Glu Gly Thr Glu Ile
        195                 200                 205

Arg Tyr Gly His Glu Val Lys Ser Ile Lys Ala Asp Gly Ala Lys Trp
    210                 215                 220

Ile Val Thr Val Lys Asn Val His Thr Gly Asp Thr Lys Thr Ile Lys
225                 230                 235                 240

Ala Asn Phe Val Phe Gly Ala Gly Tyr Ala Leu Asp Leu Leu
                245                 250                 255

Arg Ser Ala Gly Ile Pro Gln Val Lys Gly Phe Ala Gly Phe Pro Val
                260                 265                 270

Ser Gly Leu Trp Leu Arg Cys Thr Asn Glu Glu Leu Ile Glu Gln His
            275                 280                 285

Ala Ala Lys Val Tyr Gly Lys Ala Ser Val Gly Ala Pro Pro Met Ser
        290                 295                 300

Val Pro His Leu Asp Thr Arg Val Ile Glu Gly Lys Gly Leu Leu
305                 310                 315                 320

Phe Gly Pro Tyr Gly Gly Trp Thr Pro Lys Phe Leu Lys Glu Gly Ser
                325                 330                 335

Tyr Leu Asp Leu Phe Lys Ser Ile Arg Pro Asp Asn Ile Pro Ser Tyr
            340                 345                 350

Leu Gly Val Ala Ala Gln Glu Phe Asp Leu Thr Lys Tyr Leu Val Thr
        355                 360                 365

Glu Val Leu Lys Asp Gln Asp Lys Arg Met Asp Ala Leu Arg Glu Tyr
370                 375                 380

Met Pro Glu Ala Gln Tyr Gly Asp Trp Glu Thr Ile Val Ala Gly Gln
385                 390                 395                 400

Arg Val Gln Val Ile Lys Pro Ala Gly Phe Pro Lys Phe Gly Ser Leu
                405                 410                 415

Glu Phe Gly Thr Thr Leu Ile Asn Asn Ser Glu Gly Thr Ile Ala Gly
            420                 425                 430

Leu Leu Gly Ala Ser Pro Gly Ala Ser Ile Ala Pro Ser Ala Met Ile
        435                 440                 445

Glu Leu Leu Glu Arg Cys Phe Gly Asp Arg Met Ile Glu Trp Gly Asp
450                 455                 460

Lys Leu Lys Asp Met Ile Pro Ser Tyr Gly Lys Lys Leu Ala Ser Glu
465                 470                 475                 480

Pro Ala Leu Phe Glu Gln Gln Trp Ala Arg Thr Gln Lys Thr Leu Lys
                485                 490                 495

Leu Glu Glu Ala

<210> SEQ ID NO 27
<211> LENGTH: 30
<212> TYPE: DNA
<213> ORGANISM: Artificial Sequence
<220> FEATURE:
<223> OTHER INFORMATION: Primer mqo-int1-bam

<400> SEQUENCE: 27
```

```
ctagggatcc ccgaagaacg caccgaggat                                              30

<210> SEQ ID NO 28
<211> LENGTH: 30
<212> TYPE: DNA
<213> ORGANISM: Artificial Sequence
<220> FEATURE:
<223> OTHER INFORMATION: Primer mqo-int2-bam

<400> SEQUENCE: 28
ctagggatcc ggcggatgga cttgaacagg                                              30
```